United States Patent [19]

Heath, Jr. et al.

[11] Patent Number: 5,843,935
[45] Date of Patent: Dec. 1, 1998

[54] PROTEIN KINASE C INHIBITORS

[75] Inventors: William F. Heath, Jr., Fishers; Michael R. Jirousek, Indianapolis; John H. McDonald, III, Carmel; Christopher J. Rito, Mooresville, all of Ind.

[73] Assignee: Eli Lilly and Company, Indianapolis, Ind.

[21] Appl. No.: 903,236

[22] Filed: Jul. 12, 1997

Related U.S. Application Data

[63] Continuation of Ser. No. 643,707, May 6, 1996, abandoned, which is a continuation of Ser. No. 413,735, Mar. 30, 1995, Pat. No. 5,624,949, which is a continuation-in-part of Ser. No. 316,973, Oct. 3, 1994, abandoned, which is a continuation-in-part of Ser. No. 163,060, Dec. 7, 1993, abandoned.

[51] Int. Cl.$^6$ .......................... A61K 31/55; A61K 31/395
[52] U.S. Cl. .......................................... 514/183; 514/410
[58] Field of Search .................................. 540/472, 474; 514/183

[56] References Cited

U.S. PATENT DOCUMENTS

| | | | |
|---|---|---|---|
| 4,785,085 | 11/1988 | Kaneko et al. | 536/23 |
| 4,808,613 | 2/1989 | Kaneko et al. | 514/42 |
| 4,923,986 | 5/1990 | Murakata et al. | 540/545 |
| 5,043,335 | 8/1991 | Kleinschroth et al. | 514/211 |
| 5,057,614 | 10/1991 | Davis et al. | 548/466 |
| 5,292,747 | 3/1994 | Davis et al. | 514/285 |
| 5,380,746 | 1/1995 | Barth et al. | 514/414 |
| 5,438,050 | 8/1995 | Kleinschroth et al. | 514/183 |
| 5,624,949 | 4/1997 | Heath, Jr. et al. | 514/410 |

FOREIGN PATENT DOCUMENTS

| | | | |
|---|---|---|---|
| 3914764 A1 | 11/1990 | Denmark | 403/14 |
| 0 434 057 A2 | 12/1990 | Denmark | 487/14 |
| 0 269 025 A2 | 11/1987 | European Pat. Off. | 19/44 |
| 0 470 490 A1 | 7/1991 | European Pat. Off. | 471/4 |
| WO 91/13071 | 9/1991 | European Pat. Off. | 403/14 |
| 0 508 792 A1 | 4/1992 | European Pat. Off. | C07D 498/22 |
| 0 540 956 A1 | 10/1992 | European Pat. Off. | 471/14 |
| 0 624 586 A1 | 11/1994 | European Pat. Off. | C07D 471/04 |
| 0 328 000 A2 | 2/1989 | Germany | 487/14 |
| 0 384 349 A1 | 2/1990 | Germany | 403/4 |
| 0 397 060 A2 | 5/1990 | Germany | 403/14 |
| WO 91/13070 | 9/1991 | Germany | 403/4 |
| WO 94/14798 | 7/1994 | Germany | C07D 403/14 |
| WO 94/02488 | 2/1994 | WIPO | C07D 498/22 |
| WO 94/07895 | 4/1994 | WIPO | C07D 487/22 |

OTHER PUBLICATIONS

Derwent Abstract 90–132947/18; 21.10.88–DE–835842.
Derwent Abstract 92–274042/33;90.11.20 90JP–314628.
Meier, et al., *Tetrahedron Letters*, 34:33, 5277–5280 (1993).
Wilkinson, et al., *Bichem. J.*, 294, 335–337 (1993).
Bit, et al., *J. Med. Chem.*, 36, 21–29 (1993).
Martiny–Baron, et al., *The Journal of Biological Chemistry*, 268:13, 9194–9197 (1993).
Krakowiak, et al, *SYNLETT*, 611–620, (Sep. 1993).
Mulqueen, et al., *Agents Actions*, 37, 85–89 (1992).
Davis, et al., *J. Med. Chem.*, 35, 177–184 (1992).
Davis, et al., *J. Med. Chem.*, 35, 994–1001 (1992).
Toullec, et al., *The Journal of Biological Chemistry*, 266:24, 15771–15781 (1991).
Nixon, et al., *Drugs Exptl. Clin. Res.*, 17:8, 389–393 (1991).
Davis, et al., *Tetrahedron Letters*, 31:36, 5201–5204 (1990).
Brenner, et al., *Tetrahedron Letters*, 44:10, 2887–2892 (1988).
Joyce, et al., *The Journal of Organic Chemistry*, 52:7, 1177–1186 (1987).
Buchdunger, et al., *Proc. Natl. Acad. Sci. USA*, 91, 2334–2338 (Mar. 1994).
Kobayashi, et al., *The American Physiological Society*, H1214–H1220 (1994).
Felsenstein, et al., *Neuroscience Letters*, 174 173–176 (1994).
Demaerschalck, et al., *Biochimica et Biophysica Acta*, 11881 214–218 (1993).
Shimohama, et al., *Neurology*, 43 1407–1413 (1993).
Fieser and Fieser, *Reagents for Organic Synthesis*, XII, John Wiley & Sons, p. 108 (1986).

*Primary Examiner*—Richard L. Raymond
*Assistant Examiner*—Pavanaram K. Sripada
*Attorney, Agent, or Firm*—David E. Boone

[57] ABSTRACT

This invention provides novel bis-indolemaleimide macrocycle derivatives of the formula:

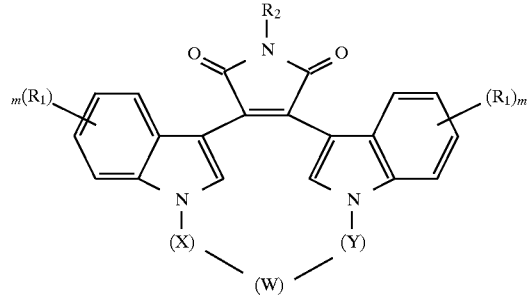

The invention further provides the preparation, pharmaceutical formulations and the methods of use for inhibiting Protein Kinase C in mammals.

7 Claims, No Drawings

PROTEIN KINASE C INHIBITORS

This application is a continuation of application Ser. No. 08/643,707, filed May 6, 1996 now abandoned; which is a continuation of application Ser. No. 08/413,735, filed Mar. 30, 1995 (issued) now U.S. Pat. No. 5,624,949 which is a C.I.P. of 08/316,973 filed Oct. 3, 1994 now abandoned; which is a C.I.P. of 08/163,060 filed Dec. 7, 1993 now abandoned.

BACKGROUND OF THE INVENTION

Protein kinase C (PKC) consists of a family of closely related enzymes that function as serine/threonine kinases. Protein kinase C plays an important role in cell-cell signaling, gene expression, and in the control of cell differentiation and growth. At present, there are currently at least ten known isozymes of PKC that differ in their tissue distribution, enzymatic specificity, and regulation. Nishizuka Y. *Annu. Rev. Biochem.* 58: 31–44 (1989); Nishizuka Y. *Science* 258: 607–614 (1992).

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40–80% homology at the amino acid level among the group. However, the homology of a single isozyme between different species is generally greater than 97%.

Protein kinase C is a membrane-associated enzyme that is allosterically regulated by a number of factors, including membrane phospholipids, calcium, and certain membrane lipids such as diacylglycerols that are liberated in response to the activities of phospholipases. Bell, R. M. and Burns, D. J., *J. Biol. Chem.* 266: 4661–4664 (1991); Nishizuka, Y. *Science* 258: 607–614 (1992). The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

Only one or two of the protein kinase C isozymes may be involved in a given disease state. For example, the elevated blood glucose levels found in diabetes lead to an isozyme-specific elevation of the beta-2 isozyme in vascular tissues. Inoguchi et al., *Proc. Natl. Acad. Sci. USA* 89: 11059–11065 (1992). A diabetes-linked elevation of the beta isozyme in human platelets has been correlated with their altered response to agonists. Bastyr III, E. J. and Lu, J. *Diabetes* 42: (Suppl. 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88: 9315–9319 (1991); Hsieh et al., *J. Biol. Chem.* 268: 15118–15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847–15853 (1993).

The ubiquitous nature of the protein kinase C isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds should demonstrate greater efficacy and lower toxicity by virtue of their specificity.

The microbial indolocarbazole, staurosporine, is a potent inhibitor of protein kinase C that interacts with the catalytic domain of the enzyme. Tamaoki et al., Biochem. *Biophys. Res. Commun.* 135: 397–402 (1986); Gross et al., *Biochem. Pharmacol.* 40: 343–350 (1990). However, the therapeutic usefulness of this molecule and closely related compounds is limited by the lack of specificity for protein kinase C over other protein kinases. Ruegg, U. T. and Burgess, G. M., *Trends Pharmacol. Sci.* 10: 218–220 (1989). This lack of selectivity results in unacceptable toxicity in this class of molecules.

An additional class of compounds related to staurosporine, the bisindolemaleimides, has been the focus of recent work. Davis et al., *FEBS Lett.* 259: 61–63 (1989); Twoemy et al., *Biochem. Biophys. Res. Commun.* 171: 1087–1092 (1990); Toullec et al., *J. Biol. Chem.* 266: 15771–15781 (1991); Davis et al., *J. Med. Chem.* 35: 994–1001 (1992); Bit et al., *J. Med. Chem.* 36: 21–29 (1993). Some of these compounds have demonstrated selectivity for protein kinase C over other protein kinases.

Although compounds that demonstrate specificity to protein kinase C have been discovered, very little is known regarding isozyme selectivity. For example, analysis of the isozyme selectivity of staurosporine, shows little isozyme selectivity with the exception of poor inhibition of the zeta isozyme relative to the other isozymes. McGlynn et al., *J. Cell. Biochem.* 49: 239–250 (1992); Ward, N. E., and O'Brian, C. A., *Molec. Pharmacol.* 41: 387–392 (1992). Studies of the PKC-selective compound, 3-[1-(3-dimethylaminopropyl)-indol-3-yl]-4-(1H-indol-3-yl)-1H-pyrrole-2,5-dione, suggest a slight selectivity for the calcium dependent isozymes. Toullec et al., *J. Biol. Chem.* 266: 15771–15781 (1991). Subsequent studies of this compound observed no difference, or possibly slight selectivity, for alpha over beta-1 and beta-2 isozymes. Martiny-Baron et al., *J. Biol. Chem.* 268: 9194–9197 (1993); Wilkinson, et al., *Biochem. J.* 294: 335–337 (1993). Therefore, despite years of research and the identification of classes of compounds that inhibit protein kinase C versus other protein kinases, there remains a need for therapeutically effective isozyme-selective inhibitors.

The present invention provides novel, potent protein kinase C inhibitors. The compounds of the present invention are selective to protein kinase C over other kinases and are, quite surprisingly, highly isozyme-selective. As selective inhibitors the compounds are useful in treating conditions associated with diabetes mellitus and its complications, ischemia, inflammation, central nervous system disorders, cardiovascular disease, dermatological disease and cancer.

SUMMARY OF THE INVENTION

This invention provides compounds of Formula I:

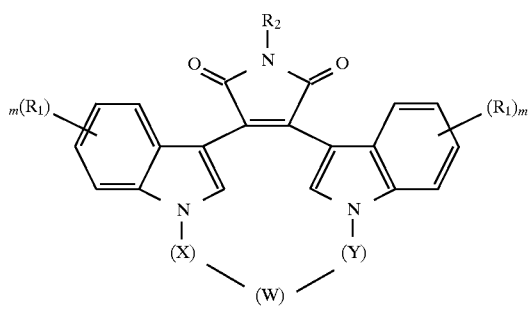

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR3—, —NOR$_3$—, —CONH—, or —NHCO—;

X and Y are independently C$_1$-C$_4$ alkylene, substituted alkylene, or together X, Y, and W combine to form —(CH$_2$)$_n$—AA—;

R$_1$ is independently hydrogen, halo, C$_1$-C$_4$ alkyl, hydroxy, C$_1$-C$_4$ alkoxy, haloalkyl, nitro, NR$_4$R$_5$, or —NHCO(C$_1$-C$_4$ alkyl);

R$_2$ is hydrogen, CH$_3$CO—, NH$_2$, or hydroxy;

R$_3$ is hydrogen, (CH$_2$)$_m$aryl, C$_1$-C$_4$ alkyl, —COO(C$_1$-C$_4$ alkyl), —CONR$_4$R$_5$, —(C=NH)NH$_2$, —SO(C$_1$-C$_4$ alkyl), —SO$_2$(NR$_4$R$_5$), or —SO$_2$(C$_1$-C$_4$ alkyl);

R$_4$ and R$_5$ are independently hydrogen, C$_1$-C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5.

Also provided are novel intermediates of the above compounds. These intermediates are compounds of the Formula II.

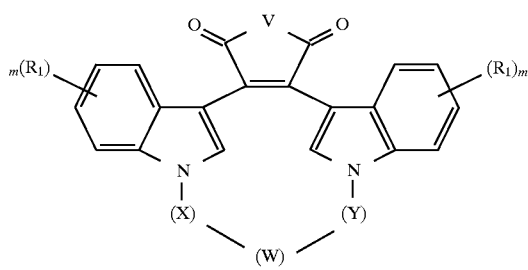

wherein:

V is —O— or N—CH$_3$;

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$_3$—, —NOR$_3$—, —CONH—, or —NHCO—;

X and Y are independently C$_1$-C$_4$ alkylene, substituted alkylene, or together X, Y, and W combine to form —(CH$_2$)$_n$—AA—;

R$_1$ is independently hydrogen, halo, C$_1$-C$_4$ alkyl, hydroxy, C$_1$-C$_4$ alkoxy, haloalkyl, nitro, NR$_4$R$_5$, or —NHCO(C$_1$-C$_4$ alkyl);

R$_3$ is hydrogen, (CH$_2$)$_m$aryl, C$_1$-C$_4$ alkyl, —COO(C$_1$-C$_4$ alkyl), —CONR$_4$R$_5$, —(C=NH)NH$_2$, —SO(C$_1$-C$_4$ alkyl), —SO$_2$(NR$_4$R$_5$), or —SO$_2$(C$_1$-C$_4$ alkyl);

R$_4$ and R$_5$ are independently hydrogen, C$_1$-C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5.

An additional aspect of this invention is a process of preparing the compounds of Formula II, which comprises:

Combining a mixture of a compound at a concentration of about 1.5 molar to about 0.001 molar of the formula:

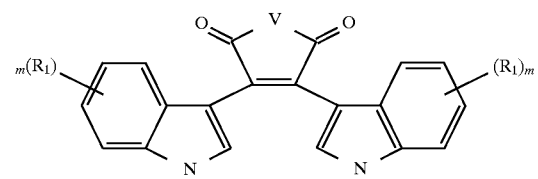

wherein:

V is O, or N—CH3;

R$_1$ is independently hydrogen, halo, C$_1$-C$_4$ alkyl, hydroxy, C$_1$-C$_4$ alkoxy, haloalkyl, nitro, NR$_4$R$_5$, or —NHCO(C$_1$-C$_4$ alkyl);

m is independently 0, 1, 2, or 3;

and an alkylating agent at a concentration of about 1.5 molar to about 0.001 molar of the formula:

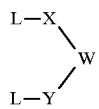

wherein

L is a leaving group;

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)mO—, -heterocycle-, -heterocycle-(CH$_2$)mO—, -fused bicyclic-, -fused bicyclic-(CH$_2$)mO—, —NR$_3$—, —NOR$_3$—, —CONH—, or —NHCO—;

X and Y are independently C$_1$-C$_4$ alkylene or substituted alkylene;

R$_3$ is hydrogen, (CH$_2$)$_m$aryl, C$_1$-C$_4$ alkyl, —COO(C$_1$-C$_4$ alkyl), —CONR$_4$R$_5$, —(C=NH)NH2, —SO(C$_1$-C$_4$ alkyl), —SO$_2$(NR$_4$R$_5$), or —SO$_2$(C$_1$-C$_4$ alkyl);

R$_4$ and R$_5$ are independently hydrogen, C$_1$-C$_4$ alkyl, phenyl, benzyl, or combine to the nitrogen to which they are bonded to form a saturated or unsaturated 5 or 6 member ring;

m is independently 0, 1, 2, or 3;

with about 0.5 to about 10 equivalents of Cs$_2$CO$_3$ at a rate from about 0.1 mL/hour to about 2.0 mL/hour in a polar aprotic solvent.

Yet another process of preparing the compounds of Formula II, comprises: Combining a compound at a concentration of about 3 molar to about 0.001 molar of the formula:

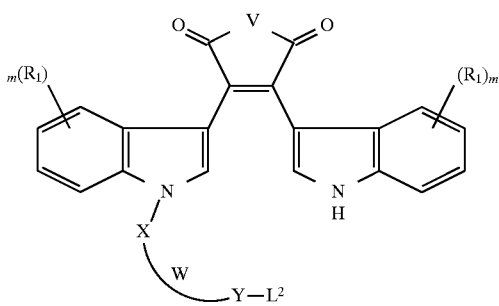

wherein:
$L^2$ is independently a leaving group;
V i s —O— or N—CH$_3$;
W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—-heterocycle-, -heterocycle-(CH$_2$)$_m$O—, -fused bicyclic-, -fused bicyclic-(CH$_2$)$_m$O—, —NR$_3$—, —NOR$_3$—, —CONH—, or —NHCO—;

X and Y are independently C$_1$-C$_4$ alkylene or substituted alkylene;

R$_1$ is independently hydrogen, halo, C$_1$-C$_4$ alkyl, hydroxy, C$_1$-C$_4$ alkoxy, haloalkyl, nitro, NR$_4$R$_5$, or —NHCO(C$_1$-C$_4$ alkyl);

R$_3$ is hydrogen, (CH$_2$)$_m$aryl, C$_1$-C$_4$ alkyl, —COO(C$_1$-C$_4$ alkyl), —CONR$_4$R$_5$, —(C=NH)NH$_2$, —SO(C$_1$-C$_4$ alkyl), —SO$_2$(NR$_4$R$_5$), or —SO$_2$(C$_1$-C$_4$ alkyl);

R$_4$ and R$_5$ are independently hydrogen, C$_1$-C$_4$ alkyl, phenyl, benzyl, or combine to the nitrogen to which they are bonded to form a saturated or unsaturated 5 or 6 member ring;

m is independently 0, 1, 2, or 3;

with about 0.5 to about 10 equivalents of Cs$_2$CO$_3$ at a rate from about 0.1 mL/hour to about 2.0 mL/hour in a polar aprotic solvent.

One further aspect of the invention is a method of inhibiting Protein Kinase C, which comprises administering to a mammal in need of such treatment a pharmaceutically effective amount of a compound of the Formula I. Also included is a method of selectively inhibiting the beta-1 and beta-2 protein kinase C isozymes, which comprises administering to a mammal in need of such treatment a pharmaceutically effective amount of a compound of the Formula I.

The invention further provides methods for treating conditions that protein kinase C has demonstrated a role in the pathology, such as ischemia, inflammation, central nervous system disorders, cardiovascular disease, dermatological disease, and cancer, which comprise administering to a mammal in need of treatment a pharmaceutically effective amount of a compound of the Formula I.

This invention is particularly useful in treating diabetic complications. Therefore, this invention further provides a method for treating diabetes mellitus, which comprises administering to a mammal in need of such treatment a pharmaceutically effective amount of a compound of the Formula I.

A final aspect of the invention are pharmaceutical formulations comprising a compound of Formula I together with one or more pharmaceutically acceptable excipients, carriers, or diluents.

DETAILED DESCRIPTION AND PREFERRED EMBODIMENTS

As noted above, the invention provides compounds of the Formula I which selectively inhibit protein kinase C. The preferred compounds of this invention are those of Formula I wherein the moieties -X-W-Y- contain 4 to 8 atoms, which may be substituted or unsubstituted. Most preferably, the moieties -X-W-Y- contain 6 atoms.

Other preferred compounds of this invention are those compounds of Formula I wherein R$_1$ and R2 are hydrogen; and W is a substituted alkylene, —O—, —S—, —CONH—, —NHCO— or —NR$_3$-. Particularly preferred compounds are compounds of the Formula Ia:

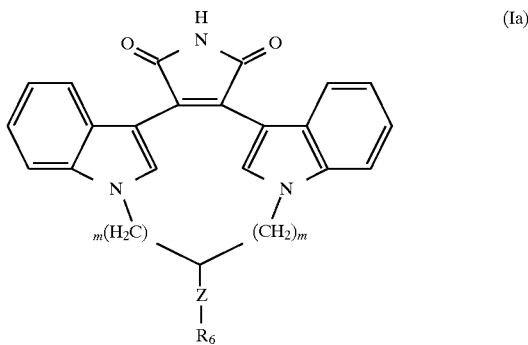

wherein Z is —(CH$_2$)p- or —(CH$_2$)p—O—(CH$_2$)p-; R$_6$ is hydroxy, —SH, C$_1$-C$_4$ alkyl, (CH$_2$)$_m$aryl, —NH(aryl), N(CH$_3$)(CF$_3$), NH(CF$_3$), or —NR$_4$R$_5$; R$_4$ is hydrogen or C$_1$-C$_4$ alkyl; R$_5$ is hydrogen, C$_1$-C$_4$ alkyl or benzyl; p is 0, 1, or 2; and m is independently 2 or 3. Most preferred compounds of the Formula Ia are those wherein Z is CH$_2$; R$_6$ is —NH$_2$, —NH(CF$_3$), or N(CH$_3$)$_2$.

Other preferred compounds are compounds wherein W is —O—, Y is substituted alkylene, and X is alkylene. These compounds are represented by Formula Ib:

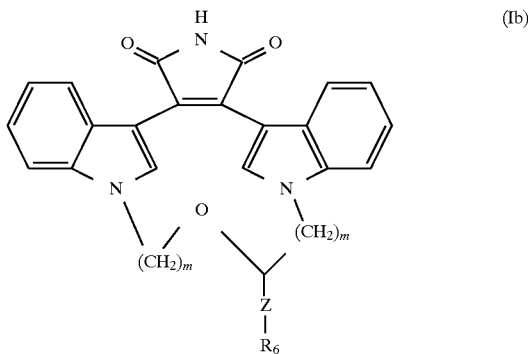

wherein Z is —(CH$_2$)p-; R$_6$ is NR$_4$R$_5$, NH(CF$_3$), or N(CH$_3$)(CF$_3$); R$_4$ and R$_5$ are independently H or C$_1$-C$_4$ alkyl; p is 0, 1, or 2; and m is independently 2 or 3. Most preferred compounds of the Formula Ib are those wherein p is 1; and R$_4$ and R$_5$ are methyl.

The term "halo" represents fluorine, chlorine, bromine, or iodine.

The term "C$_1$-C$_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A haloalkyl is one such alkyl substituted with one or more halo atoms, preferably one to three halo atoms. An example of a haloalkyl is trifluoromethyl. A C1-C4 alkoxy is a C$_1$-C$_4$ alkyl group covalently bonded by an —O— linkage.

The term "C$_1$-C$_4$ alkylene" represents a one to four carbon, straight alkylene moiety of the formula—(CH$_2$)$_r$— wherein r is one to four. Examples of C$_1$-C$_4$ alkylene include methylene, ethylene, trimethylene, methylethylene, tetramethylene, and the like. Similarly, a "$C_2$-$C_6$ alkylene" represents a two to six carbon, straight alkylene moiety. Preferably, $C_2$-$C_6$ alkylene is a two to four carbon alkylene.

The term "$C_2$-$C_6$ alkenylene" represents a two to six carbon, straight or branched hydrocarbon containing one or more double bonds, preferably one or two double bonds. Examples of a $C_2$-$C_6$ alkenylene include ethenylene, propenylene, 1,3 butadieneyl, and 1,3,5-hexatrienyl.

The term "aryl" represents a substituted or unsubstituted phenyl or naphthyl. Aryl may be optionally substituted with one or two groups independently selected from hydroxy, carboxy, $C_1$-$C_4$ alkoxy, $C_1$-$C_4$ alkyl, haloalkyl, nitro, —$NR_4R_5$, —$NHCO(C_1$-$C_4$ alkyl), —NHCO(benzyl), —NHCO(phenyl), SH, S($C_1$-$C_4$ alkyl), —OCO($C_1$-$C_4$ alkyl), —$S_2(NR_4R_5)$, —$SO_2(C_1$-$C_4$ alkyl), —$SO_2$(phenyl), or halo. The term $(CH_2)_m$ aryl is preferably benzyl or phenyl.

The term "substituted alkylene" represents a moiety of the formula:

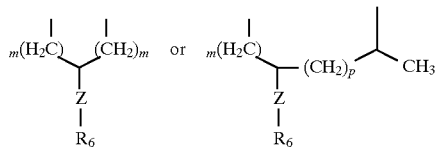

wherein Z is —(CH2)p-or —$(CH_2)$p—O—$(CH_2)$p-; $R_6$ is $C_1$-$C_4$ alkyl, $C_1$-$C_4$ alkoxy, $(CH_2)_m$aryl, $(CH_2)_m$aryloxy, hydroxy, carboxy, —COO($C_1$-$C_4$ alkyl)), —COO(($CH_2)_m$ aryl), —CO($C_1$—$C_4$ alkyl), —$NR_4R_5$, $NH(CF_3)$ —$N(CF_3)$ $(CH_3)$, —$N(R_4R_5)(OR_5)$, —$NH(CH_2)_m$aryl, —$NH(CH_2)_m$ pyridyl, —CONH(($CH_2)_m$aryl), —CONH($C_1$-$C_4$ alkyl), —NHCO($C_1$-$C_4$ alkyl), —NHCO($CH_2)_m$aryl, —OCONH ($C_1$-$C_4$ alkyl), —OCONH($CH_2)_m$aryl, —NHCOO(alkyl), —NHCOO(benzyl), —$NHSO_2(C_1$-$C_4$ alkyl), —NHSO2 $(CH_2)_m$aryl, —CN, —SH, —S($C_1$-$C_4$ alkyl), —S(aryl), —$SO_2(NR_4R_5)$, —$SO_2(C_1$-$C_4$ alkyl), —SO($C_1$-$C_4$ alkyl), glycosyl, or heterocycle; $R_4$ and $R_5$ are independently hydrogen, $C_1$-$C_4$ alkyl, phenyl, benzyl, or combine to the nitrogen to which they are bonded to form a saturated or unsaturated 5 or 6 member ring; p is independently 0, 1 or 2; and m is independently 0, 1, 2, or 3. Preferably Z is —$CH_2$—; and $R_6$ is $C_1$-$C_4$ alkyl, aryl, or —$NR_4R_5$.

The term "heterocycle" represents a stable, substituted or unsubstituted, saturated or unsaturated 5 or 6 membered ring, said ring having from one to four heteroatoms that are the same or different and that are selected from the group consisting of sulfur, oxygen, and nitrogen; and when heterocycle contains two adjacent carbon atoms, the adjacent carbon atoms may be structured to form a group of the formula —CH=CH—; provided that (1) when the heterocyclic ring contains 5 members, the heteroatoms comprise not more than two sulfur or two oxygen atoms but not both; and (2) when the heterocyclic ring contains 6 members and is aromatic, sulfur and oxygen are not present. The heterocycle may be attached at any carbon or nitrogen which affords a stable structure. The heterocycle may be substituted with one or two groups independently selected from $C_1$-$C_4$ alkyl, $C_1$-$C_4$ alkoxy, hydroxy, acetyl, carboxy, haloalkyl, nitro, —$NR_4R_5$, —NHCO($C_1$-$C_4$ alkyl), —NHCO(benzyl), —NHCO(phenyl), SH, S($C_1$-$C_4$ alkyl), —OCO($C_1$-$C_4$ alkyl), —$SO_2(NR_4R_5)$, —$SO_2(C_1$-$C_4$ alkyl), —$SO_2$(phenyl), or halo. Examples of an heterocycle include pyrazole, pyrazoline, imidazole, acetylimidazole, isoxazole, triazole, tetrazole, oxazole, 1,3-dioxolone, thiazole, oxadiazole, thiadiazole, pyridine, dipyridyl, pyrimidine, piperizine, morpholine, pyrazine, pyrrolidine, piperidine, piperazine, oxazolidinone, imidozolidinone, and aminopyridine.

The term "glycosyl" represents a 5 or 6 carbon sugars, preferably selected from allosyl, altrosyl, glucosyl, mannosyl, gulosyl, idosyl, galactosyl, talosyl, arabinosyl, xylosyl, lyxosyl, rhamnosyl, ribosyl, deoxyfuranosyl, deoxypyranosyl, and deoxyribosyl. The glycose may be azide substituted, O-acetylated, O-methylated, amino, mono, and di-alkylamino substituted, or acylamino substituted.

The term "fused bicyclic" represents a stable fused bicyclic ring system of the formula:

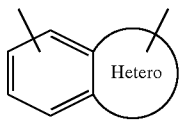

wherein Hetero represents a substituted or unsubstituted, saturated or unsaturated 5 or 6 membered ring, said ring having from one to three heteroatoms that are the same or different and that are selected from the group consisting of sulfur, oxygen, and nitrogen; and when Hetero contains two adjacent carbon atoms, the adjacent carbon atoms may be structured to form a group of the formula —CH=CH—; provided that (1) when the Hetero ring contains 5 members, the heteroatoms comprise not more than two sulfur or two oxygen atoms but not both; and (2) when the Hetero ring contains 6 members and is aromatic, sulfur and oxygen are not present. The fused bicyclic may be attached at any carbon or nitrogen atom which affords a stable structure. The fused bicyclic may be substituted with one or two groups independently selected from $C_1$-$C_4$ alkyl, $C_1$-$C_4$ alkoxy, hydroxy, carboxy, haloalkyl, nitro, —$NR_4R_5$, —NHCO ($C_1$-$C_4$ alkyl), —NHCO(benzyl), —NHCO(phenyl), SH, S($C_1$-$C_4$ alkyl), —OCO($C_1$-$C_4$ alkyl), —$SO_2(NR_4R_5)$, —$SO_2(C_1$-$C_4$ alkyl), —$SO_2$(phenyl), or halo. Examples of a fused bicyclic include indole, imidazo(1,2-a)pyridine, benzotriazole, benzimidazole, benzotriazole, benzoxazole, benzoxathiazole, quinoline, isoquinoline, phthalazine, quinazoline, quinazolinone, quinoxaline, and aminoisoquinoline.

The term "amino acid residue" refers to moiety of the formula

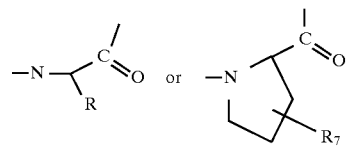

wherein R represents the variable side chain of an amino acid and $R_7$ is hydrogen or hydroxy. The variable side chain of an amino acid represents the atom or group bonded to an α-carbon atom also having bonded thereto a carboxyl and an amino group. For example, the variable region of the naturally occurring amino acids are of the formulas:

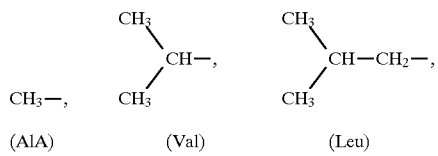

(AlA)    (Val)    (Leu)

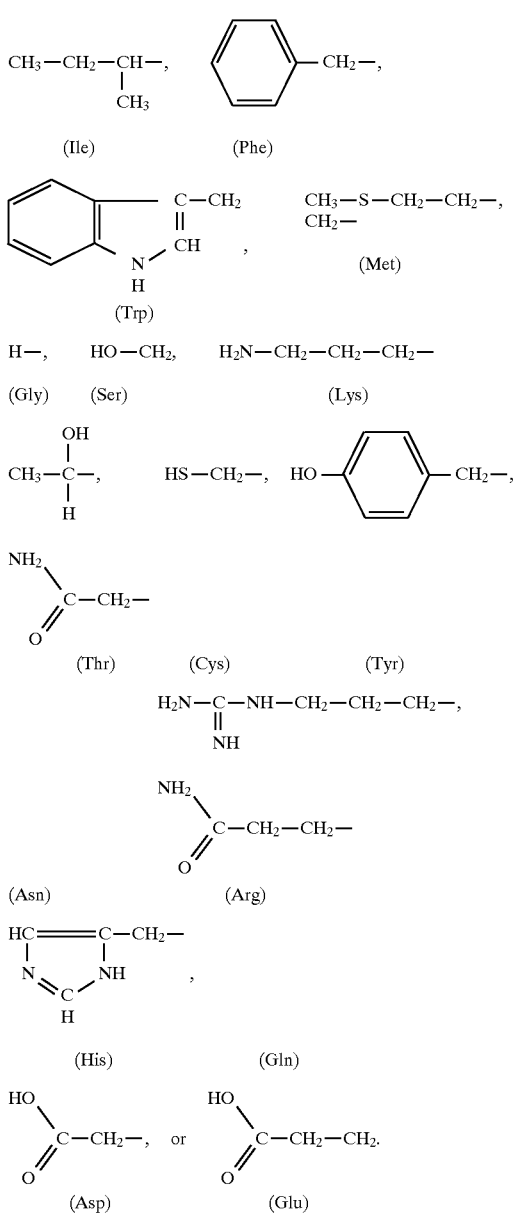

In addition to the naturally occurring amino acids, the term amino acid residue includes positional isomers and variants. Examples of positional isomers and variants represented by amino acid residue include: 2-Aminoadipic acid (Aad), 3-aminoadipic acid (bAad), β-alanine (bAla), 2-aminobutyric acid (Abu), 4-aminobutyric acid (4Abu), 6-aminocaproic acid (Acp), 2-aminoheptanoic acid (Ahe), 2-aminoisobutyric acid (Aib), 3-aminoisobutyric acid (bAib), 2-aminopimelic acid (Apm), 2,4-diaminobutyric acid (Dbu), desmosine (Des), 2,2'-diaminopimelic acid (Dpm), 2,3-diaminopropionic acid (Dpr), N-ethylglycine (EtGly), N-ethylasparagine (EtAsn), hydroxylysine (Hyl), allohydroxylysine (aHyl), 3-hydroxyproline (3Hyp), 4-hydroxyproline (4Hyp), isodesmosine (Ide), allo-isoleucine (alle), naphthylglycine, N-methylglycine (MeGly), N-methylisoleucine (MeIle), N-methyllysine (MeLys), norvaline (Nva), norleucine (Nle), ornithine (Orn), phenylglycine, cyanoalanine (CA), γ-carboxyglutamate, O-phosphoserine, α-naphthylalanine (NA), β-naphthylalanine (bNA), S-galactosyl cysteine, glycinamide, N-formylmethionine, tyrosine-O-sulfate and the like. These amino acid residues may be in either the D or L configuration. Unless otherwise specified, a reference to an amino acid will refer to the L configuration.

The term "leaving group" as used in the specification is understood by those skilled in the art. Generally, a leaving group is any group or atom that enhances the electrophilicity of the atom to which it is attached for displacement. Preferred leaving groups are triflate, mesylate, tosylate, imidate, chloride, bromide, and iodide. If the alkylating agent contains an amino acid residue (i.e., X, W, and Y combine to form —(CH$_2$)$_n$—AA—) the leaving group attached to the carboxy is preferably pentaflourophenyl ester or para-nitrophenyl ester.

The term "carboxy protecting group" as used in the specification refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the condition of subsequent reaction(s) and can be removed at the appropriate point without disrupting the remainder of the molecule. T. W. Greene and P. Wuts, *Protective Groups in Organic Synthesis*, John Wiley and Sons, New York, N.Y., 1991, Chapter 5, provide a list of commonly employed protecting groups. See also E. Haslam, *Protective Groups in Organic Chemistry*, J. G. W. McOmie, Ed., Plenum Press, New York, N.Y., 1973. A related term is "protected carboxy," which refers to a carboxy-protecting group.

The term "hydroxy protecting group" as used in the specification refers to one of the ether or ester derivatives of the hydroxy group commonly employed to block or protect the hydroxy group while reactions are carried out on other functional groups on the compound. The species of hydroxy protecting group employed is not critical so long as the derivatized hydroxy group is stable to the condition of subsequent reaction(s) and can be removed at the appropriate point without disrupting the remainder of the molecule. T. W. Greene and P. Wuts, *Protective Groups in Organic Synthesis*, John Wiley and Sons, New York, N.Y., 1991, provide a list of commonly employed protecting groups. Preferred hydroxy protecting groups are tert-butyldiphenylsilyloxy (TBDPS), tert-butyldimethylsilyloxy (TBDMS), triphenylmethyl (trityl), methoxytrityl, or an alkyl or aryl ester. A related term is "protected hydroxy," which refers to a hydroxy protecting group.

The term "amino protecting group" as used in the specification refers to substituents of the amino group commonly employed to block or protect the amino functionality while reacting other functional groups on the compound. The species of amino-protecting group employed is not critical so long as the derivatized amino group is stable to the condition of subsequent reaction(s) and can be removed at the appropriate point without disrupting the remainder of the molecule. T. W. Greene and P. Wuts, *Protective Groups in Organic Synthesis*, Chapter 7, provide a list of commonly employed protecting groups. See also J. W. Barton, *Protective Groups in Organic Chemistry*, Chapter 2. Preferred amino-protecting groups are t-butoxycarbonyl, pthalimide, a cyclic alkyl, and benzyloxycarbonyl. The related term "protected amino" defines an amino group substituted with an amino protecting group as defined.

The term "—NH protective groups" as used in the specification refers to sub-class of amino protecting groups that are commonly employed to block or protect the —NH functionality while reacting other functional groups on the compound. The species of protecting group employed is not critical so long as the derivatized amino group is stable to the condition of subsequent reaction(s) and can be removed at the appropriate point without disrupting the remainder of the molecule. T. W. Greene and P. Wuts, *Protective Groups in Organic Synthesis*, Chapter 7, page 362–385, provide a list of commonly employed protecting groups. Preferred —NH protecting groups are carbamate, amide, alkyl or aryl sulfonamide. The related term "protected —NH" defines a group substituted with an —NH protecting group as defined.

The term "pharmaceutically effective amount", as used herein, represents an amount of a compound of the invention that is capable of inhibiting PKC activity in mammals. The particular dose of the compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.05 to about 10 mg/kg, ideally about 0.1 to about 5 mg/kg. However, for topical administration a typical dosage is about 1 to about 500 $\mu$g compound per cm$^2$ of an affected tissue. Preferably, the applied amount of compound will range from about 30 to about 300 $\mu$g/cm$^2$, more preferably, from about 50 to about 200 $\mu$g/cm$^2$, and, most preferably, from about 60 to about 100 $\mu$g/cm$^2$.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isozyme selective" means the preferential inhibition of protein kinase C beta-1 or beta-2 isozyme over protein kinase C isozymes, alpha, gamma, delta, epsilon, zeta, and eta. In general, the compounds demonstrate a minimum of a eight fold differential (preferably a ten fold differential) in the dosage required to inhibit PKC beta-1 or beta-2 isozyme and the dosage required for equal inhibition of the alpha protein kinase C isozyme as measured in the PKC assay. The compounds demonstrate this differential across the range of inhibition and are exemplified at the IC50, i.e., a 50% inhibition. Thus, isozyme-selective compounds inhibit the beta-1 and beta-2 isozymes of protein kinase C at much lower concentrations with lower toxicity by virtue of their minimal inhibition of the other PKC isozymes.

By virtue of their acidic moieties, the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of the basic moiety, the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para- bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, $\beta$-hydroxybutyrate, glycollate, maleate, tartrate, methanesulfonate, propanesulfonate, naphthalene-1-sulfonate, naphthalene-2-sulfonate, mandelate and the like salts.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of Formula I can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

It is recognized that various stereoisomeric forms of the compounds of Formula I may exist; for example, W may contain a chiral carbon atom in the substituted alkylene moiety. The compounds are normally prepared as racemates and can conveniently be used as such, but individual enantiomers can be isolated or synthesized by conventional techniques if so desired. Such racemates and individual enantiomers and mixtures thereof form part of the present invention.

The invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, *Design of Prodrugs*, (1985).

The synthesis of certain bis-indole-N-maleimide derivatives is described in Davis et al. U.S. Pat. No. 5,057,614, herein incorporated by reference. Generally, the compounds of the present invention may be prepared as follows:

Scheme 1

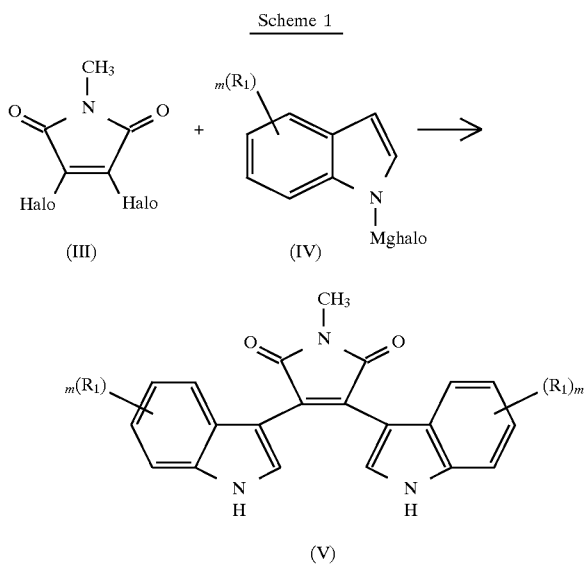

R₁, m, and halo are the same as previously defined. Halo is preferably chloro, bromo, or iodo. Compound III is preferably 2,3-dichloro N-methylmaleimide.

The reaction between Compound III and the indole, Compound IV, is commonly known as a Grignard reaction. The reaction is carried out in an inert organic solvent, such as toluene, at a temperature between room temperature and the reflux temperature of the reaction mixture. Most significantly, the reaction depicted in Scheme 1 is dependent on solvent conditions. When carried out in a Toluene:THF:ether solvent system, the reaction provides Compound V in greater than 80 percent yield and greater than 95 percent purity. The product is precipitated from the reaction mixture with ammonium chloride, $NH_4Cl$. The resulting intermediate, Compound V, may be isolated by standard techniques.

Bis-3,4(3'-indolyl)-1N-methyl-pyrrole-2,5-dione, Compound V, may then be converted by alkaline hydrolysis to the corresponding anhydride of the Formula VI by techniques known in the art and described in Brenner et al., *Tetrahedron* 44: 2887–2892 (1988). Preferably, Compound V is reacted with 5N KOH in ethanol at a temperature ranging from 25° C. to reflux.

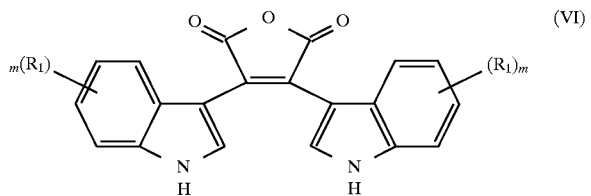

Compounds of the Formula V are generally more stable than the compounds of the Formula VI. Therefore, it is preferred that Compounds V are reacted in accordance with Scheme 2 to produce the compounds of Formula I. However, one skilled in the art would recognize that the compounds of the Formula VI, may also be reacted according to Scheme 2.

Scheme 2

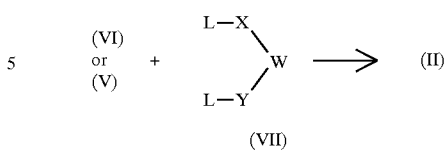

X, Y, and W are the same as previously defined. L is a good leaving group such as chloro, bromo, iodo, mesyl, tosyl, and the like. L may also be a hydroxy or other precursor that may be readily converted to a good leaving group by techniques known in the art. For example, the hydroxy may be readily converted to a sulfonic ester such as mesyl by reacting the hydroxy with methanesulfonyl chloride to produce the mesylate leaving group.

The reaction represented by Scheme 2 is accomplished by any of the known methods of preparing N-substituted indoles. This reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of iodide salt, such as potassium iodide may be added to speed the reaction. Reaction conditions include the following: Potassium hexamethyldisilazide in dimethylformamide or tetrahydrofuran, sodium hydride in dimethylformamide.

Preferably, the reaction is carried out under slow reverse addition with cesium carbonate in either acetonitrile, dimethylformamide (DMF), or tetrahydrofuran (THF). The temperature of the reaction is preferably from about ambient temperature to about the reflux temperature of the reaction mixture.

One skilled in the art would recognize that the reaction described in Scheme 2 may be employed with compounds of the Formula VIIa:

X' and Y' are a protected carboxy, protected hydroxy, or a protected amine. After the alkylation of Scheme 2, X' and Y' may be converted to moieties capable of coupling to form W. This method is the preferred method of preparing the compounds of Formula I wherein W is —S—, —O—, or NR₃. The coupling of X' and Y' to form the various ether, thioether or aminoether derivatives is known in the art and described in, for example, Ito, et al., *Chem. Pharm. Bull.* 41(6): 1066–1073 (1993); Kato, et al., *J. Chem. Pharm. Bull.* 34: 486 (1986); Goodrow, et al. *Synthesis* 1981: 457; Harpp, et al., *J. Am. Chem. Soc.* 93: 2437 (1971); and Evans, et al., *J. Org. Chem.* 50: 1830 (1985).

One skilled in the art would also recognize that the compounds of Formula V may be converted to the compounds of Formula II in a two step synthesis as described in Scheme 3.

Scheme 3

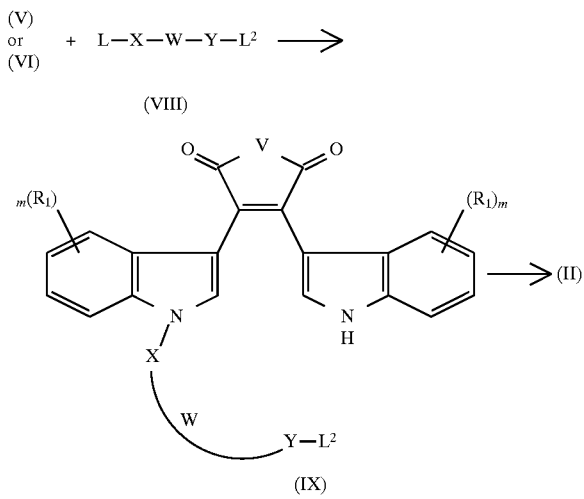

$R_1$, X, W, Y, V and L are the same as previously defined. $L^2$ is a protected hydroxy or other group that may be readily converted to a good leaving group by techniques known in the art. The coupling between Compound V or VI and Compound VIII is an alkylation as previously discussed. The monoalkylated intermediate, IX, is deprotected, and $L^2$ is converted to a leaving group. For example, if the hydroxy is protected with t-butyldimethylsilyl (TBDMS), TBDMS is selectively removed using acidic methanol. The resulting free hydroxy is then converted to a leaving group, such as an alkyl halide, preferably an alkyl iodide or bromide ($CBr_4$ in triphenylphosphine) or sulfonate (mesyl chloride in triethylamine). The macrolide is then formed by alkylating under slow reverse addition to a solution of base, such as potassium hexamethyldisilazide, or sodium hydride but preferably $Cs_2CO_3$ in a polar aprotic solvent such as acetonitrile, DMF, THF at temperatures ranging from ambient to reflux.

Schemes 2 and 3 exemplify the process of the present invention. Most unexpectedly, the compounds of the Formula II may be prepared in substantially higher yield when the alkylation is carried out under slow reverse addition to $Cs_2CO_3$ in a polar aprotic solvent. Slow reverse addition involves combining a mixture of compound and alkylating agent (Scheme 2) or the compound (Scheme 3) with the base at a rate from about 0.1 mL/hour to about 2.0 mL/hour. The concentration of each reagent in the mixture is about 1.5 molar to about 0.001 molar. When carried out with the monoalkylated compound (Scheme 3) the concentration is from about 3 molar to about 0.001 molar. The slow addition results in a concentration of reagents in the reaction vessel of about 0.01 μmolar to 1.5 molar. One skilled in the art would recognize that at a higher rate of addition a lower concentration of reagents could be used in the reaction. Likewise, at a slower rate of addition, a higher concentration of reagents could be used in the reaction. Preferably, the compound is added at about 0.14 mL/hour with the compound and the alkylating agent at 0.37 molar. It is preferred that the $Cs_2CO_3$ be added in excess—most preferably a 4:1 ratio $Cs_2CO_3$ to alkylating agent. Preferred polar aprotic solvents are acetonitrile, dimethylformamide (DMF), acetone, dimethylsulfoxide (DMSO), dioxane, diethylene glycol methyl ether (diglyme), tetrahydrofuran (THF), or other polar aprotic solvents in which the reagents are soluble. The reaction is carried out at temperatures ranging from about 0° C. to reflux. One skilled in the art would recognize that the ratio of the mixture of the compound and alkylating agent is not critical. However, it is preferred that the reagents are mixed in a ratio of 0.5 to 3 equivalents of each other. Most preferably, the reagents are mixed 1:1.

When V is N—$CH_3$, Compound II is converted to the corresponding anhydride (V is O) by alkaline hydrolysis. Alkaline hydrolysis involves reacting the compound with a base, such as sodium hydroxide or potassium hydroxide, in $C_1$–$C_4$ alcohol (preferably ethanol), DMSO/water, dioxane/water, or acetonitrile/water at a temperature ranging from about 25° C. to preferably about reflux. The concentration of the reactants is not critical.

The anhydride (V is O) is converted to the maleimide of Formula I by ammonolysis. Ammonolysis involves reacting the anhydride with an excess of hexamethyldisilazane or an ammonium salt (ammonium acetate, bromide, or chloride) and $C_1$–$C_4$ alcohol (preferably methanol) in an polar aprotic solvent such as DMF at room temperature. Preferably, the hexamethyldisilazane or an ammonium salt is reacted at a ratio greater than about 5:1 equivalents of anhydride.

Yet another method of preparing the compounds of Formula I is outlined in Scheme 4. This method is 5 particularly useful when W is —NH and X or Y is a substituted alkylene.

Scheme 4

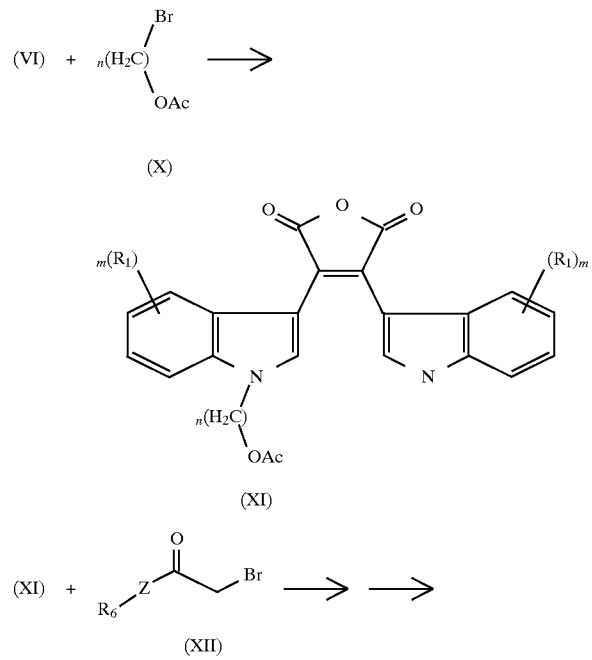

-continued
Scheme 4

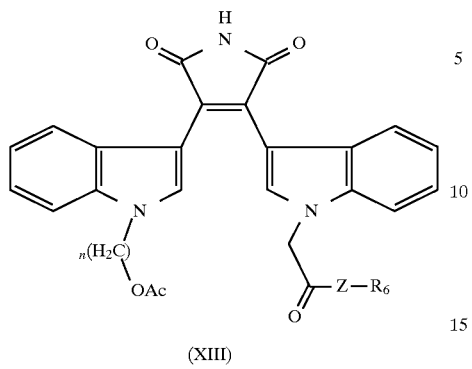

(XIII)

(XIII) →

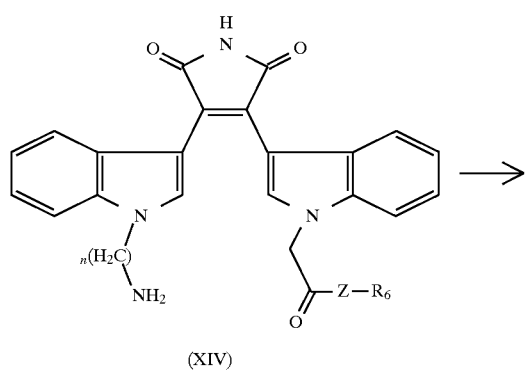

(XIV)

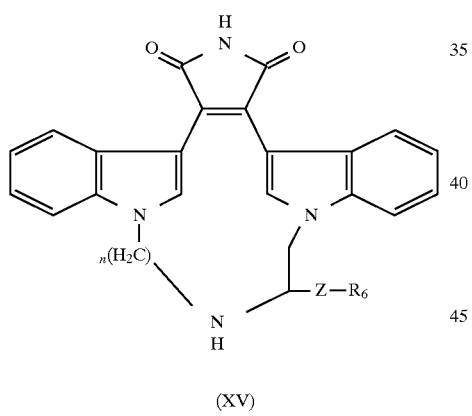

(XV)

Ac is acetyl. $R_1$, $R_6$, z, n, and m are the same as previously defined. The alkylation of Compound VI with X occurs under conditions previously described and known in the art. Likewise, alkylation of Compound XI with the α-halo ketone, Compound XII, occurs under conditions previously discussed. The conversion of the anhydride to the maleimide, Compound XV, occurs as previously described. For example, the anhydride may be converted to the bis-indole maleimide by reacting the anhydride with hexamethyldisilazane and methanol in an inert organic solvent such as DMF at room temperature.

The protected hydroxy, represented by OAc, is readily hydrolyzed to form an alcohol (for example, $K_2CO_3$ in aqueous methanol and THF). The resulting alcohol is converted to a leaving group by methods appreciated in the art such as reacting the alcohol with mesyl chloride in triethylamine at 0° C. The leaving group is substituted with an azide, such as $NaN_3$ in DMF at 50° C. The resulting azide is reduced to form the amine by employing Lindlar's catalyst in the presence of $H_2$. The macrocycle is allowed to close via an intramolecular Schiff base. The Schiff base is reduced under standard conditions, such as $NaCNBH_3$ or other reducing agents, to form the macrocycles of Formula I.

Yet another method of preparing the compounds of Formula I is outlined in Scheme 5. This method is particularly useful when X, W, and Y are taken together to form —$(CH_2)_n$—AA—.

Scheme 5

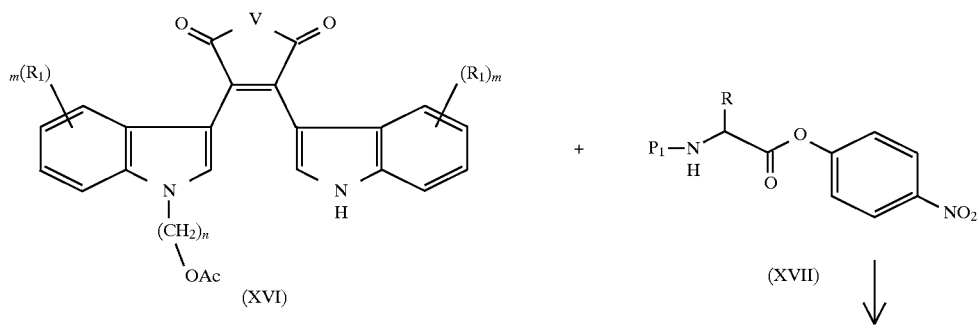

Scheme 5

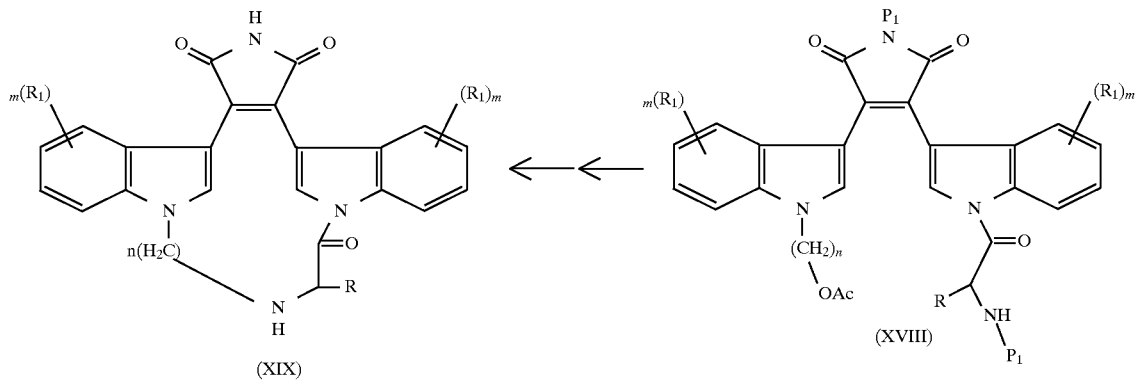

$R_1$, Ac, V, m, and n are the same as previously defined. $P_1$ represents an amino protecting group. R represents the variable side chain of an amino acid. The acylation of Compound XVI with an activated amino acid (such as the para-nitrophenyl ester, illustrated) is carried out using 18-crown-6 and KF in THF, DMF, or dimethoxyethane at room temperature as described in Klausner, et al., *J. Chem. Soc.* PERKIN I 607–631 (1977); and Nakagawa, et al., *J. Am. Chem. Soc.* 105: 3709–3710 (1983). Closure of the macrocycle to form Compound XIX is carried out via formation of the intramolecular Schiff base as described in Scheme 4.

An additional method of preparing the compounds of Formula I and a preferred method when W is —CONH— or —NHCO—, is described in Scheme 6.

$R_1$, Ac, V, $P_1$, m, and n are the same as previously defined. The reaction between Compound XX and Compound XXI occurs in the presence of ethyl diisopropylamine in methylene chloride at 0° C. The macrocycle is formed via an intramolecular alkylation of the free indole nitrogen and the α-halo carbonyl terminus under alkylating conditions previously described. The protected maleimide is deprotected as previously discussed to produce the Compound XXIII.

An alternative method of preparing the intermediates, Compounds XI and XX is described in Scheme 7.

Scheme 6

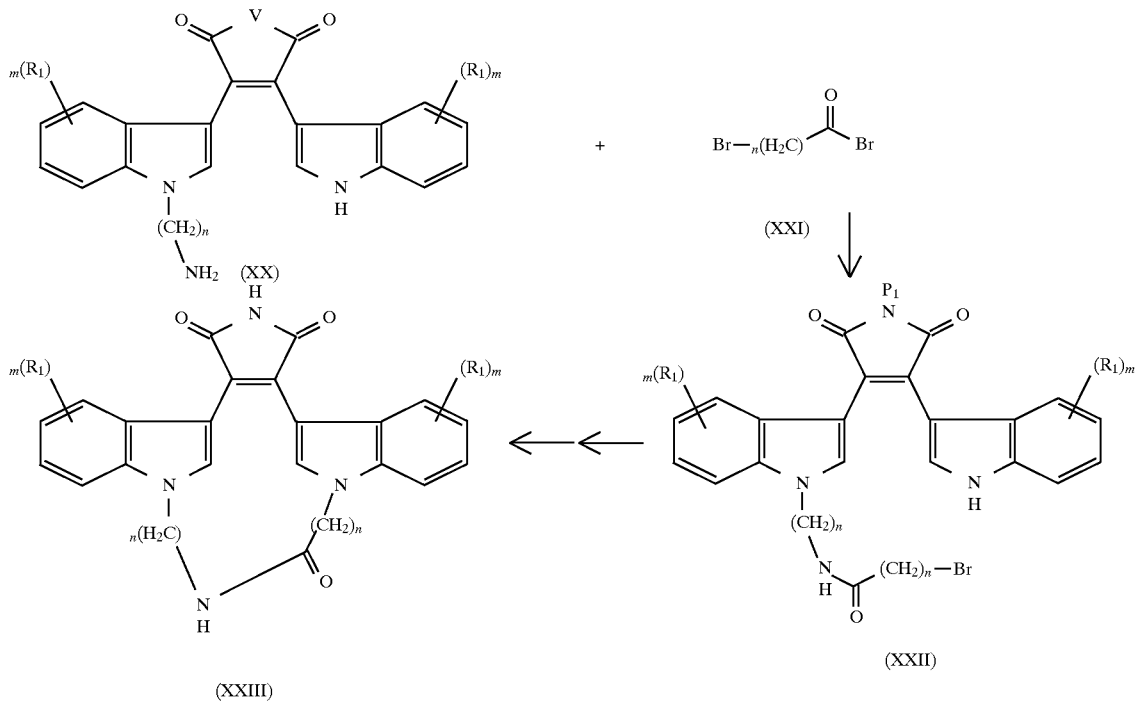

Scheme 7

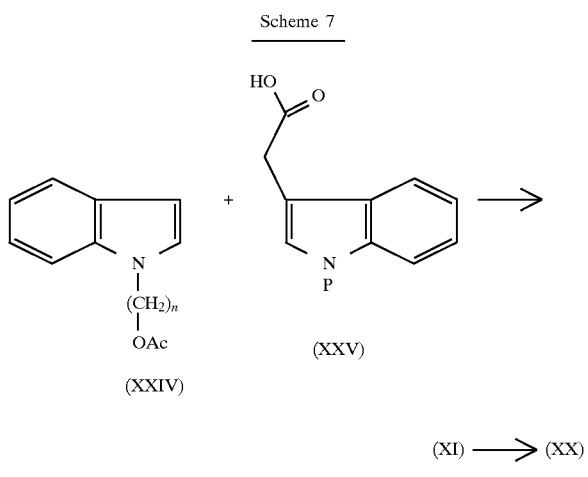

Ac is the same as previously defined; P is an indole protecting group such as t-butoxycarbonyl or other indole protecting group known in the art. T. W. Greene and P. Wuts, *Protecting Groups in Organic Synthesis*, Chapter 7, page 385. The reaction described in Scheme 7 is known as a Perkin Condensation. The reaction is described in Hill et al., *J. Med. Chem.* 36: 21–29 (1993). Generally, oxalyl chloride is added at between −78° C. and the reflux temperature of the mixture (preferably at 0° C.) to an anhydrous solution of Compound XXIV in inert organic solvent such as a halogenated aliphatic hydrocarbon like methylene chloride. After about one to three hours, the volatiles are removed. The resulting solids are dissolved in a dry halogenated aliphatic hydrocarbon solvent, e.g. methylene chloride; and added to Compound XXV in the presence of an acid binding agent, preferably a tertiary amine such as triethylamine, at room temperature.

The resulting anhydride, Compound XI is reacted in accordance with Schemes 4 or 5 or converted to the maleimide or a protected maleimide as previously discussed.

The protected hydroxy (preferably OAc, illustrated) of Compound XI may be converted to an alcohol by techniques known in the art. For example, Compound XI is reacted with $NH_4OH$ or aqueous ammonia in DMF at elevated temperatures, e.g. 140° C. The resulting alcohol is converted to the amine, Compound XX, by methods known in the art. For example, the alcohol in dichloromethane and collidine under a nitrogen atmosphere is reacted with triflic anhydride in dichloromethane. After approximately two hours, the mixture is treated with aqueous ammonia. The resulting amine, Compound XX is then reacted in accordance with Scheme 6.

An intermediate of the present invention is prepared in accordance with Scheme 8. This scheme is particularly useful in preparing compounds wherein W is —O—, Y is substituted alkylene, and X is alkylene.

Scheme 8

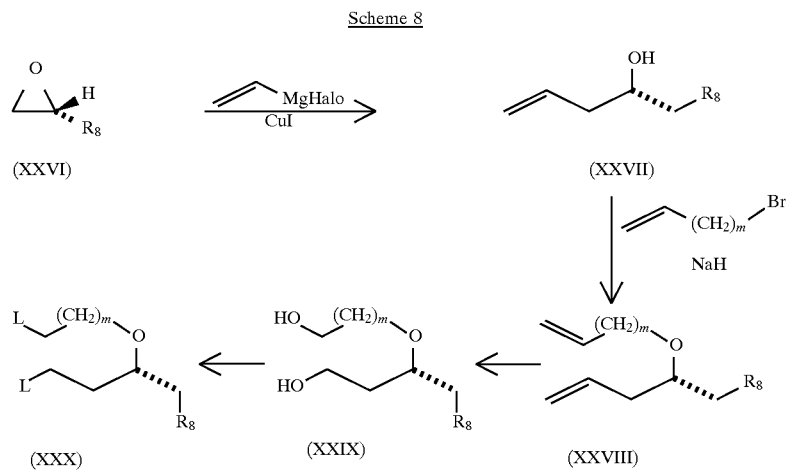

$R_8$ is $N_3$, NH-protecting group, amine protecting group, or hydroxy protecting group; m is independently 0, 1, 2, or 3; and L is a good leaving group such as chloro, bromo, iodo, mesyl, tosyl and the like. L is preferably mesyl. $R_8$ is preferably a protected hydroxy, most preferably —Otrityl. Scheme 8 presents a stereoselective synthesis of the linker portion (—X—W—Y—) of the macrocycle. The S-enantiomer is illustrated above; however, one skilled in the art would recognize that the complimentary enantiomer or mixture of enantiomers could be prepared in an analogous manner. Furthermore, one skilled in the art would recognize that an analogous reaction with a methyl substituted epoxide or Grignard reagent could be used to prepare the various linkers (—X—W—Y—) containing a methyl substituted alkylene.

In the above reaction, the epoxide, Compound (XXVI), is opened using a Grignard reagent. The reaction is carried out in the presence of copper complexing agent; however other alkylating conditions are operative. The reaction is carried out in an inert solvent at a temperature between −30° C. and reflux temperature of the reaction mixture. The reaction produces Compound (XXVII) which may be further reacted without purification. Compound (XXVII) is allylated under general conditions known in the art for preparing ethers. The reaction illustrated in Scheme 8 is a Williamson synthesis. The formation of sodium alkoxide using NaH, NaOH, or KOH followed by allylation with allyl bromide produces the diene, Compound (XXVIII). Compound (XXVIII) is converted to the alcohol, Compound (XXIX), under standard techniques. For example, Compound (XXVIII) can be converted to an ozonide by treating with ozone at low temperatures. The ozonide is then reduced with $NaBH_4$, $LiAlH_4$, $BH_3$ or catalytic hydrogenation with excess $H_2$ to produce the alcohol, Compound (XXIX). The hydroxy moieties of Compound (XXIX) are converted to leaving group, L, by standard techniques such as reacting the alcohol with mesyl chloride in triethylamine.

In all of the above schemes, it is preferred that the reactions be carried out with appropriate protecting groups. In particular, it is preferred that $R_1$ is protected during the alkylations and/or acylations and subsequently deprotected. Likewise, if $R_6$ is to be a —$NR_4R_5$, the reactions are best carried out with an amino protecting group. However, one skilled in the art recognizes that many of these reactions can be performed without protecting groups if the appropriate reaction conditions, blocking reagents, or the like are used. It is preferred that when W contains a hydroxy moiety, it is protected as tert-butyldiphenylsilyloxy (TBDPS) or triphenylmethyl (trityl) during the alkylation or acylation of the indole. The resulting compounds of Formula I may be isolated and purified by standard techniques.

Compounds III, IV, V, VII, VIIa, VIII, X, XII, XVII, XXI, XXIV, XXV, XXVI and any other reagents required for the above reactions, are either commercially available, known in the art, or can be prepared by methods known in the art. For example, Compound III may be prepared by techniques described in Edge et al., *Chem. and Ind.* 130 (1991); Compound IV is preferably prepared in situ by reacting an appropriately substituted indole with an alkylmagnesium halide such as ethylmagnesium bromide in a known manner.

The following examples and preparations are provided merely to further illustrate the invention. The scope of the invention is not construed as merely consisting of the following examples. To aid one skilled in the art, the following structure is provided to illustrate with a representative compound the nomenclature adopted herein:

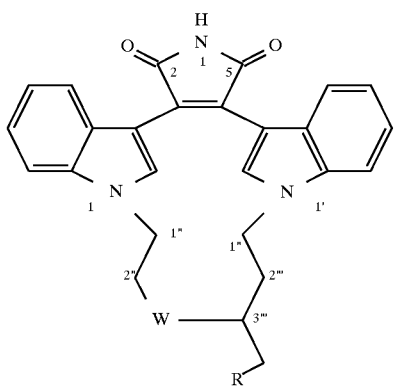

In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc respectively. The terms "NMR" and "MS" indicate that the spectrum was consistent with the desired structure.

PREPARATION 1

2,3-bis-(3'-indolyl)-furan-1,4-dione

Sodium ethoxide (3.56 g, 50 mmol) was added to a solution containing 2,3-dichloromaleic anhydride (5.56 g, 33.3 mmol) and methylamine hydrochloride (3.50 g, 55.0 mmol) in 40 mL of acetic acid. The mixture was stirred under a $CaCl_2$ drying tube at 25° C. for 16 hours and then refluxed for 4 hours. The cooled mixture was poured into water (350 mL) and extracted with EtOAc (3×75 mL). The combined organic extracts were washed with 100 mL portions of saturated aqueous $NaHCO_3$, water and brine and dried ($MgSO_4$). The solvent was evaporated under reduced pressure. The residue was recrystallized from ethanol to give 3.82 g (64%) of 2,3-dichloro N-methylmaleimide as white crystals. Concentration of the mother liquor and chromatography of the residue by radial preparative layer chromatography (Chromatotron, Harrison Research), gave an additional 0.81 g of 2,3-dichloro N-methylmaleimide, raising the yield to 77%.

A solution of indole (10.5 g, 90 mmol) in 175 mL of dry toluene was treated dropwise over 1 hour under $N_2$ with a solution of ethylmagnesium bromide (1.0M in THF, 90 mL, 90 mmol). After the addition was complete, the light-green solution was heated at 40° C. for 30 minutes and then cooled to 25° C. A solution of 2,3-dichloro N-methylmaleimide (3.8 g, 21 mmol) in 50 mL of toluene was added over a 30-minute period. The reaction mixture was heated at 100° C. for 3 hours, then cooled to 25° C., and quenched with 100 mL of 20 percent aqueous citric acid. The layers were separated. The aqueous phase was extracted with EtOAc (50 mL). The combined organic layers were dried over anhydrous $MgSO_4$. The solvent was evaporated under reduced pressure. The residue was taken up in 30 mL of acetone and allowed to stand at 5° C. for 40 hours. The solids were collected and washed with ice-cold ether to give 5.25 g (73 percent) of 3,4-bis-(3'-indolyl)-1-methyl-pyrrole-2,5-dione as a red solid, M.Pt. 276°–278° C.

To a solution of 3,4-bis-(3'-indolyl)-1-methyl-pyrrole-2, 5-dione in 150 mL of ethanol was added 5N KOH (50 mL). The mixture was stirred 4 hours at 25° C. and diluted with 150 mL of water. Most of the ethanol was evaporated under reduced pressure. The mixture was then acidified to pH 1. The precipitated product was filtered and washed with water. The crude product was dissolved in a minimum of $CH_2Cl_2$ and slowly filtered through a two-inch column of silica gel eluting with 50 percent EtOAc in hexane to give the titled compound (3.10 g 79 percent) as a red solid. M. Pt. 225°–2280° C.

PREPARATION 2

Bis-2,6-dibromomethyl pyridine

To a mixture containing 2,6-pyridinedimethanol (735 mg, 5.28 mmol) and triphenylphosphine (3.20 g, 12.2 mmol) in 35 mL of dry $CH_2Cl_2$ at 0° C. under $N_2$ was added N-bromosuccinimide (2.16 g, 12.2 mmol) in portions over 10 minutes. The mixture was stirred 1 hour at 0° C. and then allowed to stand at 5° C. for 16 hours. Most of the solvent was removed under reduced pressure. Ether (100 mL) was added to the residue. The ether layer was decanted and concentrated to 20 mL then diluted with 3:1 hexane/EtOAc (50 mL). The cloudy solution was placed in the refrigerator overnight. After evaporation of the solvents in vacuo, the crude product was recrystallized from hexane to afford 766 mg (55 percent) of bis-2,6-dibromomethyl pyridine as a white crystalline solid. MS.

PREPARATION 3

(±)-3-(Benzyloxy)methylene-1,6-dibromohexane

A solution of potassium t-butoxide (1.0M in THF, 8.27 mL, 8.27 mmol) was added dropwise to a solution of (±)-3 cyclohexene-1-methanol (853 mg, 7.60 mmol) in THF (35 mL) at 25° C. under $N_2$. The resultant mixture was stirred at 25° C. for 30 minutes. Benzyl bromide (1.0 mL, 8.37 mmol) was added dropwise. The reaction mixture was allowed to stir at room temperature for 16 hours and then treated with saturated aqueous $NH_4Cl$ (5 mL) and concentrated. The residue was dissolved in ether (50 mL), washed with water (20 mL) and brine (20 mL), and dried over $MgSO_4$. The solvent was evaporated under reduced pressure. The residue was subjected to radial chromatography on silica gel eluting with 5 percent EtOAc in hexane to give (±)-3-(benzyloxy) methyl-1-cyclohexene (1.42 g, 92 percent) as a colorless oil. NMR Ozone was bubbled through a solution of (±)-3-benzyloxymethylene-1-cyclohexene (1.35 g, 6.70 mmol) in $CH_2Cl_2$ (65 ml) at −78° C. until the blue color of unreacted ozone persisted. The reaction mixture was allowed to warm to room temperature, while dry nitrogen was bubbled through the reaction. Borane-dimethyl sulfide complex (10.0M in THF, 2.7 mL, 27.8 mmol) was added via syringe over several minutes, and the reaction mixture was allowed to stand at room temperature for 24 hours. The reaction mixture was treated with 5 percent aqueous HCl (1 mL) and stirred vigorously for one hour. Solid $NaHCO_3$ was added until the mixture tested basic to litmus paper. The mixture was dried over anhydrous $MgSO_4$. The reaction mixture was filtered and concentrated to afford the crude (±)-3-(benzyloxy)methyl-1,6 hexanediol (1.49 g, ca. 100 percent)

as an oil. This material, which showed essentially a single spot on TLC analysis, Rf=0.25, 25 percent EtOAc in hexane, was used directly in the next step without further purification.

N-Bromosuccinimide (2.49 g, 14.0 mmol) was added to a stirred mixture of (±)-3-(benzyloxy)methyl-1,6 hexanediol (1.45 g, 6.10 mmol) and triphenylphosphine (3.67 g, 14.0 mmol) in dry $CH_2Cl_2$ (50 mL) at 0° C. under $N_2$. After 12 hours, the reaction was concentrated and ether (100 mL) was added to the residue. The mixture was stirred 15 minutes; and the ether layer was decanted from the solids. This was repeated with 50 mL of ether. The combined ether extracts were concentrated to 50 mL then diluted with hexane (100 mL) After standing at 5° C. overnight, the solution was decanted from the precipitated solids and concentrated to afford dibromide (±)-3-(benzyloxy)methyl-1,6-dibromohexane (1.09 g, 49 percent) as a light yellow oil which was essentially homogeneous by TLC, Rf=0.75 (10 percent EtOAc in hexane). NMR

PREPARATION 4

1-(tert-butyldimethylsilyloxy)-4-(tert-buttldiphenylsilyloxy) -butan-3-ol

To an anhydrous $CH_2Cl_2$ (110 mL) solution of 3-buten-1-ol (15 g, 0.21 mol) was added imidazole (28.6 g, 0.42 mol, 2 eq), followed by tert-butyldimethylsilyl chloride (32 g, 0.22 mol). After 90 minutes, the reaction was complete as indicated by TLC (10% EtOAc/hexane). The $CH_2Cl_2$ solution was transferred to a separatory funnel, diluted with $CH_2C_{12}$ (110 mL), washed with water (200 mL), and brine (200 mL). The organic layer was collected, dried over $MgSO_4$, filtered, and the solvent removed to yield an oil (1-(O-TBDMS)-3-butene) which was taken on to the next reaction. MS The above oil was dissolved in a mixture of acetone (400 mL) and water (50 mL). N-Methylmorpholine-N-oxide (85.2 g, 0.63 mol, 3 eq) was then added. The resulting slurry was cooled to 0° C., and after 10 minutes a catalytic amount of $OsO_4$ (0.3 g) was added. The resulting slurry was allowed to stir overnight, gradually warming to room temperature. TLC (25% EtOAc/hexane) indicated the reaction was complete. The reaction mixture was quenched with sodium bisulfite, diluted with ether (1 L), washed with water (400 mL), and brine (400 mL). The organic layer was collected. The aqueous layer extracted with ether (2×500 mL). The combined organic layers were dried, filtered, and concentrated to yield 4-(O-TBDMS)-1,2-butanediol as an oil, which was taken on to the next reaction.

The above oil was dissolved in anhydrous $CH_2Cl_2$ (250 mL). Imidazole (30 g, 0.44 mol, 2.5 eq) was added to the solution as a solid with stirring. The resulting solution was cooled to 0° C. After cooling 15 minutes, a $CH_2Cl_2$ (50 mL) solution of tert-butyldiphenylsilyl chloride (50 g, 0.18 mol, 1 eq) was added dropwise over 45 minutes. After the addition was complete, stirring was continued at 0° C. for 2.5 hours. The solution was transferred to a separatory funnel, diluted with $CH_2Cl_2$ (250 mL), washed with water, brine, dried over $MgSO_4$, and filtered. The solvent removed under reduced pressure to give the crude product as an oil. The crude product was purified by eluting (10% EtOAc/hexane) it through a short column of silica gel. The eluting solvent was removed in vacuo to leave a viscous oil of the titled intermediate. (78.1 g, 93% overall yield). MS

PREPARATION 5

1-(tert-butyldimethylsilyloxy)-3-(3-iodoproploxy)-4-(tert-butyldiphenylsilyloxy)-butane To a inethylene chloride (20 mL)/cyclohexane (100 ML) solution of the alcohol of Preparation 4 was added allyl trichloroacetimidate (17.82 g, 88 mmols, 2.2 eq) under an $N_2$ balloon followed by trifluoromethanesulfonic acid (50 µL/g of starting material, 0.92 mL). After 20 hours, the solution was filtered, and the filtrate was washed with saturated aqueous $NaHCO_3$, water, and then brine. The organic layer was collected and dried over $MgSO_4$. The solvent was removed to give an oil, which was purified by flash chromatography on silica gel eluting with hexanes and increasing the polarity of the mobile phase to 5% ethyl acetate in hexanes over several liters to yield 19.27 g of the allylic ether, 1-(tert-butyldimethylsilyloxy)-3-(propeneoxy) -4-(tert-butyldiphenylsilyloxy)-butane as a light brown oil (97% yield). MS.

To a THF (60 mL) solution of the above allyl ether (14.16 g, 28.38 mmols, 1 eq) was added 9-BBN (9-borabicyclo [3.3.1]nonane, 0.5M solution in THF, 60 mL, 30 mmols, 1.1 eq) dropwise under nitrogen. After 3 hours, TLC (10% EtOAc in hexanes) of the reaction showed that the starting material had been consumed. To this solution was added 3M aqueous NaOH (10.41 mL, 31.22 mmols, 1.1 eq) followed by slow (1.5 hr) dropwise addition of 30% hydrogen peroxide (10.3 mL, 90.82 mmols, 3.2 eq). The reaction temperature during the peroxide quench was kept below 50° C.(ice bath).

After 30 minutes, sodium chloride was added until the solution was saturated. The organic layer was removed; the aqueous layer was extracted with ether; the combined organic layers were dried and filtered; and the filtrate concentrated to give an oil. The crude oil was purified by flash chromatography on silica gel eluting with 10% EtOAc/ hexanes and increasing the polarity to 20% EtOAc/hexanes after about 1.5 liters of solvent to yield 9.53 g of a light yellow oil (65% yield). MS.

To an anhydrous 0° C. ether (150 mL) solution of the above alcohol was added triethylamine (2.93 g, 28.91 mmols, 1.5 eq.) followed by dropwise addition of mesyl chloride (3.31 g, 28.91 mmols, 1.5 eq.) with vigorous stirring. After 3 hours at 0° C., TLC (10% EtOAc in hexanes) indicated the starting material was consumed. The reaction was diluted with ether, washed with water, brine, dried over $MgSO_4$, and the solvent removed. The resulting oil was passed through a pad of silica eluting with 25% EtOAc/hexanes, and the eluant was concentrated. To an acetone (200 mL) solution of the resulting oil was added $NaHCO_3$ (0.17 g, 1.93 mmols, 0.1 eq.), and NaI (28.88 g, 192.7 mmols, 10 eq.). After stirring 30 minutes at room temperature under a nitrogen atmosphere, the reaction was heated to 50° C. with a water bath. After 2.5 hours, TLC (10% EtOAc in hexanes) indicated that the mesylate was consumed. The reaction mixture was diluted with ether (500 mL), washed with cold saturated aqueous $Na_2SO_3$, water, brine, dried ($MgSO_4$), and the solvent removed. The resulting oil was passed through a pad of silica eluting with 5% EtOAc in hexanes to give the purified title compound 10.3 g as a colorless oil (85% yield).

PREPARATION 6

3-bromopropyl acetate 3-bromopropan-1-ol (0.54 moles, 75 g) in $CH_2C_{12}$ (500 mL) at 0° C. under $N_2$ was treated with acetyl chloride (0.5 moles, 40.2 mL). To this solution was added triethylamine (0.54 moles, 75 mL) in portions (5 mL) slowly by syringe. The reaction mixture was allowed to gradually (12 hours) come to room temperature. The precipitate was filtered off, and the filter was washed with $CH_2C_{12}$. The filtrate washed with water (2×), brine (2×) and dried over $Na_2SO_4$, and filtered. The filtrate was concentrated to give the titled acetate 91 g (93% yield) as an oil. MS

PREPARATION 7

N-(3-acetoxypropyl)-indole

To a stirred 0° C. DMF (400 mL) suspension of NaH (60% in mineral oil, 0.705 moles, 28.2 g, 1.5 eq.) in a three-neck flask fitted with a reflux condenser and an addition funnel was added a DMF (150 mL) solution of indole (55 g, 0.47 moles) dropwise. After 30–60 minutes, a DMF (50 mL) solution of the alkyl halide, 3-bromopropyl acetate (170 g, 0.94 moles) was added. The reaction was heated at 50° C. for 6 hours and then allowed to stir at room temperature for 5–15 hours.

The solvent was removed in vacuo. The residue was partitioned between $CH_2C_{12}$ and water. The organic layer was washed with 1N HCl (3×), water, brine, dried over $Na_2SO_4$, and filtered. The filtrate was concentrated to give the titled alkyl indole 102 g as an oil which slowly crystallized. MS

PREPARATION 8

N-(tert-butoxycarbonyl)-indol-3-yl-acetic acid

To a stirred acetone (800 mL) solution of indole-3-acetic acid (26.25 g, 0.15 moles) was added cesium carbonate (48.9 g, 0.15 moles) followed by allyl bromide (15 mL, 0.17 moles, 1.16 eq.). After 12 hours the solvent was removed. The residue was partitioned between water and $CHCl_3$. The organic layer was washed with brine, dried over $Na_2SO_4$, and filtered. The filtrate was concentrated to give the allyl ester 27.9 g (74% yield) as an oil.

To an acetonitrile (500 mL) solution of the allyl ester (27.9 g) was added di-tert-butyl dicarbonate (29.1 g, 0.133 moles, 1.2 eq.) and 4-dimethylaminopyridine (1.36 g, 0.011 moles, 0.1 eq.). After 15 minutes, the reaction mixture was diluted with EtOAc (1.2 L) and washed with 0.1N HCl, water (2×), and brine (2×). The organic layer was dried over $Na_2SO_4$, filtered, and concentrated to give the BOC protected ester (32.9 g, 94%) as an oil which slowly crystallized.

To a $CH_2Cl_2$/EtOAc 10:3 (325 mL) solution of the BOC protected ester was added sodium 2-ethylhexanoate (17.3 g, 0.104 moles), triphenylphosphine (4.93 g, 18.8 mmol, 0.18 eq.) and $Pd(PPh_3)_4$ (4.56 g, 3.95 mmol, 0.04 eq.). After 1 hour, the solvent was removed. The residue was partitioned between EtOAc and water. The basic aqueous layer was back extracted with EtOAc, then ether, and then carefully acidified with 0.10N HCl. The acidic aqueous layer was then extracted with EtOAc. The organic layer was washed with water, brine, dried over $Na_2SO_4$, and filtered. The filtrate was concentrated to give the BOC protected acid (21.8 g, 77% yield) as an oil which slowly crystallized. The yield of the titled compound was 53% over three steps. MS

PREPARATION 9

(±)3,4-[(N,N'-1,1'-(3"-3-tert-butyldiphenlsilyloxymethylene)hexane)-bis-(3,3'-indolyl)]-1(methyl)-pyrrole-2,5-dione A DMF (50 mL) solution of bis-(3,3'-indolyl)]-1-(methyl) -pyrrole-2,5-dione (3.41 g, 10.0 mmol) containing the dibromide 3-tert-butyldiphenylsilyloxymethylene-1,6-dibromohexane (5.64 g, 11 mmol, prepared in a manner analogous to the benzoyl derivative in Preparation 2) was added using a syringe pump over a 15 hour period to a DMF (350 mL) slurry of $Cs_2CO_3$ (11.2 g, 34.3 mmol) at 60 °C. After 4 hours from completion of the addition, the reaction was cooled to room temperature, poured into water (1.5 L), and extracted with $CH_2Cl_2$ (3×300 mL). The organic phase was washed with water, dried, filtered and concentrated. The concentrate was purified by flash chromatography eluting with 10% to 25% ethyl acetate/hexane to give the macrocycle 3,4-[(N,N'-1,1'-(3"-3-tert-butyldiphenylsilyloxymethylene)hexane)-bis-(3,3'-indolyl)]-1(methyl)-pyrrole-2,5-dione 2.95 g (43% yield) as a red oil. MS

PREPARATION 10

(S)-methyl 4-tert-butyldiphenylsilyloxy-3-(allyloxy) butyrate

To a cyclohexane (400 mL) solution of (S)-methyl 4-tert-butyldiphenylsilyloxy-3-(hydroxy)butyrate (20.0 g, 53.7 mmol) was added allyl trichloroacetimidate (21.74 g, 107.4 mmol), followed by trifluoromethanesulfonic acid (1 mL, 50 mL/g alcohol) in five portions over 30 minutes, with stirring under a nitrogen atmosphere. After 70 hours, the solids that formed were filtered, and the filter cake was washed with cyclohexane, and the volatiles were removed in vacuo. The resultant oil was placed on a plug of silica and washed with hexane, and product eluted with 10% ethyl acetate/hexane. NMR indicated the presence of residual imidate (ca. 10%); however the material was carried on without further purification. The residue yields 24.76 g of material, of which approx. 22.2 g was desired product (100%). MS.

PREPARATION 11

(S)-4-tert-butyldiphenylsilyloxy-3-(2-iodoethoxy)-1-iodobutane

DIBAL-H (231 mL, 1.0M in toluene, 231 mmol) was added dropwise over 40 minutes to a solution of (S)-methyl 4-tert-butyldiphenylsilyloxy-3-(allyloxy)-butyrate (23.8g, 57 mmol) dissolved in anhydrous THF (1.0 L) at –75° C. under $N_2$. After stirring 1.5 hours, the mixture was allowed to warm to –10° C. and quenched with 5% water in methanol and a large amount of Celite. The quenched reaction mixture was filtered through a pad of Celite; the filtrate was concentrated and partitioned between ether and 20% citric acid. The ether layer was dried and concentrated in vacuo. The residual oil was passed through a pad of silica eluting with chloroform to yield 20.6 g (93%) of (S) 4-tert-butyldiphenylsilyloxy-3-allyloxy-butan-1-ol.

To a methanol (500 mL) solution of (S) 4-tert-butyldiphenylsilyloxy-3-allyloxybutan-1-ol (20.6 g, 53.6 mmol) was added ozone at –78° C. for approximately 12 minutes. The reaction mixture developed a faint blue color, $NaBH_4$ (12.2 g, 321 mmol, 6 eq.) was added to the reaction vessel. The reaction was allowed to come to room temperature. The volatiles were removed in vacuo. The residue was passed through a plug of silica eluting with ethyl acetate to yield 16.4 g (79%) of (S) 4-tert-butyldiphenylsilyloxy-3-(2-hydroxy-ethoxy)-butan-1-ol as a colorless oil.

To an ether (600 mL) solution of (S) 4-tert-butyldiphenylsilyloxy-3-(2-hydroxy-ethoxy)-butan-1-ol (15.7 g, 40.4 mmol) at 0° C. under nitrogen was added triethylamine (16.8 mL, 121 mmol) followed by mesyl chloride (9.38 mL, 121 mmol). After 3 hours, the solution was filtered; the filtrate was washed with water (2×), brine (2×), dried over $Na_2SO_4$ and concentrated in vacuo. The residue gave 21.9 g (>99%) of the bismesylate as a yellow oil which was carried on directly. The bismesylate was dissolved in acetone (1.4 l), which had been distilled from potassium carbonate. To this solution was added NaI (90.4 g, 603 mmol) and 0.05 eq. $NaHCO_3$ (170 mg, 2mmol). The reaction mixture was kept at 56° C. for 24 hours and filtered; and the filtrate was concentrated in vacuo. The residue was partitioned between ether and 10% $Na_2SO_3$, the ether layer was washed with brine, dried over $Na_2SO_4$, and concentrated to give 17.9 g (73.2%) of (S)-4-tert-butyldiphenylsilyloxy-3-(2-iodoethoxy)-1-iodobutane as a colorless oil. The overall yield was 54%. MS: MW=608.39; observed: 559 (M-tertbutyl; FD, $CHCl_3$).

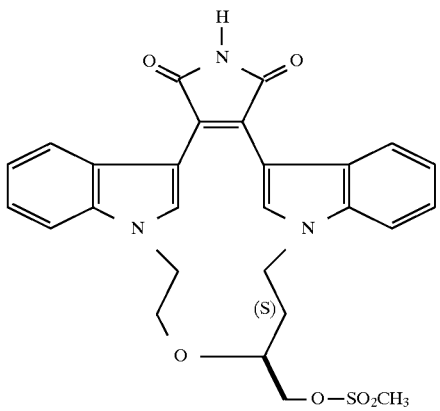

PREPARATION 12

(S)-3,4-[(N,N'-1,1')-((2'''-ethoxy)-3'''-(O)-4''-(methanesulfonyloxy)-butane)-(bis)-(3-indolyl)]-1H-pyrrole-2,5-dione 3,4-(bis)-(3-indolyl)-1H-pyrrol-2,5-dione (10.04 g, 29.4 mmol) and (S)-4-(tert-butyldiphenylsilyloxy)-3-(2-iodoethoxy)-1-(iodo)butane (17.9g, 29.4 mmol) were combined and dissolved in anhydrous DMF (80 mL). The solution was added via syringe pump addition over 72 hours to a suspension of cesium carbonate (38.3 g, 118 mmol) in anhydrous DMF (1.7 L) at 50° C. under $N_2$. The DMF was removed in vacuo. The residue was partitioned between $CHCl_3$/1N HCl. The acidic layer was back-extracted with chloroform and ethyl acetate. The combined organic layers were washed with 1N HCl (1×), water (2×), brine (2×), dried over $Na_2SO_4$, and reduced to give a magenta solid. The crude reaction mixture was used without further purification.

The crude reaction mixture was suspended in ethanol (700 mL) and treated with 5N KOH (800 mL). The reaction temperature was raised to 80° C. After 72 hours the ethanol was removed in vacuo; the aqueous suspension was cooled to 0° C., and acidified with 5N HCl. The violet precipitate was collected and passed through a silica plug eluting with ethyl acetate. The eluant was concentrated to yield 8.7 g of the partially silylated maleimide as a magenta solid that was carried on to the next reaction without further purification.

To a DMF (1 L) solution of the above anhydride (8.7 g, 19.7 mmol) was added 1,1,1,3,3,3-hexamethyldisilazane (41.6 mL, 197 mmol) and methanol (4 mL, 98.5 mmol) under nitrogen at ambient temperature. After 40 hours, the reaction was concentrated in vacuo , a 2:1 (v/v) MeCN/1N HCl solution (100 mL) was added. The residue was stirred for one hour. The organic solvent was removed; and the aqueous suspension was extracted with ethyl acetate. The solvents were removed to yield 8.9 g of maleimide that was used without further purification.

To a $CH_2Cl_2$ (800 mL) suspension of the above maleimide (8.9 g, 20 mmol) under nitrogen at ambient temperature was added pyridine (4.85 mL, 60 mmol) and a slight excess of methanesulfonic anhydride (4.21 g, 24 mmol). After 16 hours the reaction mixture was washed with 0.1N HCl, brine, and the organic layer was concentrated. The residue was passed through a plug of silica eluting with a slow gradient of 0–10% MeCN in $CH_2Cl_2$. The eluant fraction containing the desired mesylate was concentrated to yield 2.8 g of the title compound as a magenta solid. Overall yield from the diiodide is 18%. MS: MW=520; observed 520 (FD, $CHCl_3$).

PREPARATION 13

3-(tert-butyldiphenylsilyloxvmethylene)-1-cyclohexene

To a mixture of 3-cyclohexene-1-methanol (Aldrich, 13.0 mL, 0.11 mol), N,N-diisopropylethylamine (43 mL, 0.244 mol) and 4-dimethylaminopyridine (2.70 g., 0.022 mol) in 375 mL of dry $CH_2Cl_2$ under $N_2$ at 250° C. was added tert-butyldiphenylchlorosilane (32 mL, 0.123 mol). The mixture was stirred at 250° C. for 48 hours. The reaction mixture was washed sequentially with 150 mL portions of 1N HCl, water, brine and dried over anhydrous $MgSO_4$. The solvent was evaporated. The residue was loaded onto a 4"×4" column of silica and slowly eluted using hexanes as eluant. 3-(tert-butyldiphenylsilyloxymethylene)-1-cyclohexene, 33.6 g (86%), was obtained as a colorless oil which was homogenous by TLC (Rf=0.4, hexanes).

Analytical calculated for $C_{23}H_{30}OSi(0.3\ H_2O)$:
C, 77.6; H 8.67.
Found: C, 77.38; H, 8.72.

PREPARATION 14

3-(tert-butyldiphenylsilyloxymethylene)-1,6-hexanediol

Ozone was bubbled through a well-stirred solution of 3-(tert-butyldiphenylsilyloxymethylene)-1-cyclohexene, (18.0 g, 51.3 mmol) in $CH_2Cl_2$ (550 mL) at −78° C. until the blue color of unreacted ozone persisted. The reaction mixture was allowed to warm to 25° C. Dry $N_2$ was bubbled through the solution for 30 minutes. Borane-dimethylsulfide complex (10.0M, 23 mL, 0.23 mol) was added dropwise over 10 minutes. The mixture was slowly stirred under $N_2$ at 25° C. for 24 hours. 5% HCl (15 mL) was added, and the reaction mixture was stirred for 1 hour. Solid $NaHCO_3$ was added until the mixture tested basic to pH paper (external damp). After filtration, the filtrate was washed with 200 mL portions of 5% $NaHCO_3$ and water and dried over anhydrous $MgSO_4$. After evaporation of the solvent under reduced pressure, the crude product was purified by chromatography through a 4"×4" pad of silica gel eluting with EtOAc. 3-(tert-(butyldiphenylsilyloxy)methylene)-1,6-hexanediol 17.8 g (90%) was obtained as a colorless viscous oil which was homogeneous by TLC ($R_f$ 0.5, ether).

Analytical calculated for $C_{23}H_{34}O_3Si(0.2\ H_2O)$
C, 70.80; H, 8.88.
Found: C, 70.72; H, 8.86.

PREPARATION 15

3-tert-butyldiphenylsilyloxvmethylene-1,6-dibromohexane

N-bromosuccinimide (19.3 g, 109 mmol) was added in portions over five minutes to a stirred solution containing 3-(tert-butyldiphenylsilyloxymethylene)-1,6-hexanediol (17.5 g, 45.2 mmol) and triphenylphosphine (28.6 g, 109 mmol) in dry $CH_2Cl_2$ (550 mL) at 0° C. under $N_2$. The reaction mixture was stirred 5 hours at 0° C. then placed in the refrigerator at 5° C. for 16 hours. After removal of most of the solvent, dry ether (300 mL) was slowly added to the residue. The ether layer was decanted from the precipitated solids. The solids were washed with an additional 200 mL of fresh ether. The combined ether layer was concentrated (100 mL), triturated with 300 mL of hexanes, and decanted from the precipitated solids. The solids were washed with 25% ether in hexanes and the combined organic layers were dried over anhydrous $MgSO_4$ and concentrated. The crude product was placed onto a 4"×4" column of silica gel and eluted with 25% ether in hexanes to give 3-tert-butyldiphenylsilyloxymethylene-1,6-dibromohexane 20.1 g, (86%) as a colorless oil which was homogeneous by TLC (Rf=0.75, 10% EtOAc in hexanes). 1H NMR (300 MHz, $CDCl_3$) 1.06 (s,9H), 1.35–2.10 (m, 7H), 3.55 (m,4H), 3.56 (app d, 2H, J=4Hz), 7.40 and 7.64 (m, 10H).

$^{13}C$ NMR (75 MHz, $CDCl_3$) 19.2, 26.9, 29.3, 30.0, 31.9, 33.8, 34.7, 38.5, 65.0, 127.7, 129.7, 133.4, 135.5.

PREPARATION 16

(S)-(-)-3-Cyclohexene-1-methanol

A solution of $LiAlH_4$ (1.0M in THF, 75.8 mL, 75.8 mmol) was added dropwise over 15 minutes to a cooled solution of the known ester (Ireland et al J. Org. Chem. 1992, 57(19), 5071–5073 and references therein), (S)-(-)-3-Cyclohexene-1-methyleneoxy-(S)-N-methyl-2-hydroxysuccinimide, (8.20 g, 34.5 mmol) in THF (90 mL). The reaction mixture was allowed to warm to room temperature and stirred at 250° C. for 2 hours, cooled and quenched with water and 1N NaOH. The mixture was filtered through Celite. The solids were washed with THF (100 mL). After evaporation of the filtrate, under reduced pressure, the residue was dissolved into 150 mL of ether and washed with water (2×50 mL) and brine (50 mL) and dried over anhydrous $MgSO_4$. Evaporation of the solvent gave (S)-(-)-3-Cyclohexene-1-methanol 3.24 g (83%) as a clear oil $[a]D=-90:3\ (C=1, CH_3OH)$. Both the TLC properties and $^1H$ NMR spectrum of this material was identical in all respects with that of the racemic material (Aldrich).

$^1H$ NMR (300 MHZ, $CDCl_3$), 1.21–1.42 (m, 2H), 1.68–1.88 (m, 3H), 2.04–2.21 (m, 3H), 3.54 (brs, 2H), 5.69 (s, 2H).

PREPARATION 17

(S)-(-)-3-tertbutyldiphenylsilyloxymethvlene)-1-cyclohexene (S)-(-)-3-Cyclohexene-1-methanol 3.17 g, 28.3 mmol) was treated with tert-butyldiphenylchlorosilane (8.15 mL, 31.1 mmol), N,N- diisopropylethylamine (10.9 mL, 62.3 mmol) and dimethylaminopyridine (1.03 g, 8.5 mmol) in $CH_2Cl_2$ (100 mL) to afford, after workup and chromatography, silyl ether (S)-(-)-3-tertbutyldiphenylsilyloxymethylene)-1-cyclohexene 8.73 g (88%) as a clear oil. Both the TLC properties and $^1H$ NMR spectra of this material were identical in all respects with racemic silyl ether 3-tertbutyldiphenylsilyloxymethylene)-1-cyclohexene. $^1H$ NMR (300 MHz, $CDCl_3$) 1.05 (s,9H), 1.29 (m,1H), 1.71–2.18 (m,4H) 3.54 (d, 2H, J=6Hz), 5.66 (br s, 2H), 7.38 and 7.66 (m, 10 H).

PREPARATION 18

(S)-(-)- 3-(tert-butyldiphenylsilyloxymethylene)-1,6-hexanediol

Following the same procedure described for the preparation of the racemic diol 3-(tertbutyldiphenylsilyloxymethylene)-1,6-hexanediol, silyl ether (S)-(-)- 3-tert-butyldiphenylsilyloxymethylene)-1-cyclohexene (8.35 g, 23.9 mmol) was ozonized, then reductively worked-up ($BH_3$-$Me_2S$) to afford (S)-(-)-3-(tert-butyldiphenylsilyloxymethylene)-1,6-hexanediol~5.01 g (55%) as a colorless viscous oil, which was homogenous by TLC ($R_f$=0.4 EtOAc).

$^1$H NMR (300 MHz, $CDCl_3$) 1.05 (s, 9H), 1.21–1.81 (m,7H), 2.32 (br s, 2H), 3.50–3.75 (m, 6H), 7.32 and 7.70 (m,10H)

PREPARATION 19

(S)-3-(tert-butyldiphenylsilyloxymethylene)-1 6-dibromohexane

Following the same procedure described for the preparation of racemic dibromide, 3-(tert-butyldiphenylsilyloxymethyl)-1,6-dibromohexane, (S)-(-)-3-(tertbutyldiphenylsilyloxymethyl)-1,6-hexanediol (4.85 g, 12.53 mmol) was reacted with N-bromosuccinimide (5.35 g, 30.1 mmol) and triphenylphosphine (7.87 g, 30.1 mmol) $CH_2C_{12}$ (150 mL) at 0° C. to afford compound (S)-(-)-3-(tert-butyldiphenylsilyloxymethyl)-1,6-dibromohexane 4.81 (75%) as a clear, colorless oil which was homogenous by TLC ($R_f$=0.8, 10% EtOAc in hexanes. Both the TLC properties and $^1$H spectra of this compound were identical in all respects with racemic isomer. MS.

$^1$H NMR (300 MHz, $CDCl_3$) 1.06 (s,9H), 1.35–2.10 (m, 7H), 3.55 (m,4H), 3.56 (app d, 2H, J=4Hz), 7.40 and 7.64 (m, 10H).

PREPARATION 20

(R)- 3-(tert-butyldiphenylsilyloxvmethylene)-1,6-dibromohexane

Following the same procedure described for the preparation of (S)-(-)-3-(tert-butyl-diphenylsilyloxymethylene)-1, 6-dibromohexane, (S)-(-)-3-(tert-butyldiphenylsilyloxymethylene)-1,6-hexanediol (5.05 g, 13.04 mmol) was reacted with N-bromosuccinimide (5.57g, 31.32 mmol) and triphenylphosphine (8.21 g, 31.32 mmol) in $CH_2C_{12}$ (160 mL) at 0° C. to afford chiral dibromide (R)-3-(tert-butyldiphenylsilyloxymethylene)-1,6-dibromohexane, 5.85g, (87%) as a clear, colorless oil which was homogenous by TLC ($R_f$=0.8, 10% EtOAc in hexanes. MS.

$^1$H NMR (300 MHz, $CDCl_3$) 1.06 (s,9H), 1.35–2.10 (m, 7H), 3.55 (m,4H), 3.56 (app d, 2H, J=4 Hz), 7.40 and 7.64 (m, 10H).

PREPARATION 21

2-allyl-4-pentenoic acid

To a stirred suspension of sodium methoxide (59.4 g, 1.1 mol) in dry methanol (1 L) at 0° C. was added dimethylmalonate (57 mL, 0.5 mol) dropwise under N2. After 30 minutes, allyl bromide (95 mL, 1.1 mol) was added in one portion. After 14 hours, at ambient temperature the reaction was concentrated in vacuo. The residue dissolved in methanol (0.5 L) and treated with 5N NaOH (500 mL). After stirring for 24 hours, the methanol was removed in vacuo, and the basic aqueous layer washed with ethyl acetate (2×). The aqueous layer was acidified with 5N HCl (0.5 L) and extracted with ethyl acetate. The organic extract was washed with water (2×), brine, dried over $Na_2SO_4$, and concentrated in vacuo to a white solid. Trituration of the resulting solid with pentane and atmospheric drying gave 51.4 g (57% yield) of the diacid. The diacid (50 g, 274 mmol) was heated (150° C.) until $CO_2$ evolution ceased (about 2 hours). The residual brown oil was eluted with ethyl acetate through a small silica plug to yield the title compound 32.8 g (85%) as a golden oil. The overall yield for the three steps is 48%.

$^1$H NMR: ($CD_3CN$)δ2.4 (m, 4H); 2.5 (m, 1H); 5.05 (dd, 2H); 5.15 (dd, 2H); 5.9 (m, 2H); 12.8 (br, 1H). MS.

PREPARATION 22

3-(tertbutyldiphenylsilyloxymethylene)-pentane-1,5-diol

To a 0° C. stirred suspension of LAH (4.33 g, 114 mmol) in anhydrous ether (125 mL) was added 2-allyl-4-pentenoic acid (16.0 g, 114 mmol) dropwise under N2. The reaction mixture was allowed to come to room temperature over. After 16 hours, the reaction was quenched with ethanol (25 mL) followed by 4N HCl (40 mL), extracted, extracted with ether (2×), dried, and concentrated in vacuo to give a the alcohol, 2-allyl-4-penten-1-ol, as a colorless oil 11.7 g (82%) that was used without further purification.

To a dry $CH_2Cl_2$ (0.5 mL) solution of 2-allyl-4-penten-1-ol (11.7 g, 93 mmol), was added imidazole (12.6 g, 185 mmol) followed by chloro tertbutyldiphenylsilane (25.48 g, 93 mmol), and stirred for 16 hours. The reaction was filtered, the filtrate was washed with water, brine, dried and concentrated in vacuo to give the silylether, 3-(tert-butyldiphenylsilyloxymethylene)-pent-1,4-ene, 32.5g (96%) as an oil that was used without further purification.

Ozone was bubbled through a −78° C. dry methanol (500 mL) solution of 3-(tert-butyldiphenylsilyloxymethylene)-1, 5-pentanediol (17 g, 47 mmol) until a blue tint persisted (30 minutes). The reaction was purged with nitrogen (20 min.) and $NaBH_4$ (17.6g, 47 mmol) was added. The cold bath was removed and the reaction brought to room temperature. The reaction was concentrated in vacuo and the residue partitioned between ether and brine. The ether layer was concentrated and the residue eluted over a silica plug with 0–50% ethyl acetate/hexanes. The minor component was pooled and concentrated to yield the diol, 3-(tertbutyldiphenylsilyloxymethylene)-pentane-1,5-diol, 3.8g (22%) of the desired diol as a colorless oil. Overall the yield for the three steps is 17%. MS.

$^1$H NMR: δ 1.17 (s, 9H); 1.6 (dt, 4H); 1.83 (m, 1H); 2.14 (s, 2H); 3.6 (m, 6H); 7.41 (t, 4H); 7.45 (t, 2H); 7.66 (d, 4H).

PREPARATION 23

1,5-diiodo-3-(tert-butyldiphenylsilyloxymethylene)-pentane

To a 0° C. ether (300 mL) solution of 3-(tertbutyldiphenylsilyloxymethylene)-pentane-1,5-diol (6.9 g, 19 mmol) was added methanesulfonyl chloride (4.3 mL, 56 mmol) followed by $Et_3N$ (7.7 mL, 56 mmol). After 3–16 hours, gradually warming to ambient temperature, the reaction was washed with water, brine, dried over $MgSO_4$, and concentrated to give the 1,5-bis(methanesulfonyloxy)-3-(tert-butyldiphenylsilyoxymethylene)-pentane 8.5g (90%) as a colorless oil that was used without further purification.

To a freshly distilled acetone (500 mL) solution of the bis-mesylate, 1,5-bis(methanesulfonyloxy)-3-(tert-butyldiphenylsilyloxymethylene)-pentane, (8.5g, 16 mmol) was added excess NaI (36.1 g, 241 mmol) and NaHCO3 (67 mg, 0.8 mmol). The reaction was refluxed (57° C.) for 72 hours, cooled to room temperature and filtered. The filtrate was concentrated in vacuo. The residue was diluted with ether, washed with 10% $Na_2SO_3$, dried, and concentrated to give the title compound 7.4 g (78% yield) as a colorless oil. The overall yield for two steps is 70%. MS.

$^1$H NMR: (DMSO-d6) δ 1.06 (s, 9H); 1.78 (m, 1H); 1.8–2.06 (m, 4H); 3.13 (m, 4H); 3.57 (d, 2H); 7.38–7.46 (m, 3H); 7.64 (d, 2H).

PREPARATION 24

2-(2'-Bromoethoxy)-benzylbromide

Ozone was bubbled through a -78° C. dry methanol solution of 2-(allyloxy)benzyl alcohol (LaChapelle et al *Tetrahedron*, 44(16), 5033–5044 (1988)) (7.0 g, 43 mmol) for 13 minutes, checking the reaction TLC profile every 2 minutes for complete disappearance of the starting olefin (Rf=0.8, 75%EtOAc/hexane). The reaction mixture was purged with nitrogen, $NaBH_4$ (9.7 g, 0.25 mol) was added and the reaction temperature brought to 0° C. After 30 minutes, the reaction was warmed to room temperature, concentrated, diluted with ether, washed with water, brine, dried and concentrated to a residue. The residue was eluted through a pad of silica with EtOAc/hexanes (gradient elution 25%–75% EtOAC). Evaporation of the eluting solvent gave the diol, 2-(2'-hydroxyethoxy)-benzyl alcohol, (4.8 g, 67%) as an oil. MS: MW=168; observed 168, FD, $CHCl_{13}$).

To a 0° C. dry $CH_2C_{12}$ (250 mL) solution of the diol, 2-(2'-hydroxyethoxy)-benzyl alcohol, (4.38 g, 26 mmol) was added triphenylphosphine (15.8 g, 60 mmol) and N-bromosuccinamide (10.7 g, 60 mmol). After 2 hours at 0° C., the reaction was complete by TLC (20% EtOAc/$CH_2Cl_2$) analysis, and the reaction was concentrated in vacuo. The concentrate was eluted (hexane—15% EtOAc/hexane gradient) through a pad of silica gel. Concentration of eluting fractions gave the dibromide, 2-(2'-Bromoethoxy)-benzylbromide, (6.91 g, 90% yield) as a colorless solid. MS.

$^{13}$C-NMR ($CHCl_3$, 75.4 MHz)δ 28.7, 29.1, 68.2, 112.3, 121.6, 126.8, 130.2, 131.1, 156.0.

1H-NMR ($CHCl_3$, 200 MHz)δ 3.72 (2H, t, J=5 Hz), 4.34 (2H, t, J=5 Hz), 4.59 (2H,s), 6.84 (H, d, J=7 Hz), 6.95 (H, t, J=7 Hz), 7.25–7.38 (2H).

PREPARATION 25

1-(tert-butyldimethylsilyloxy)-3-(2-iodoethoxy)-4-(tert-butyldiphenyl)-butane

The allyl ether, 1-(tert-butyldimethylsilyloxy)-3-(allyloxy)-4-(tert-butyldiphenyl)-butane, (21.6 g, 43.4 mmol) was dissolved in methanol (500 mL) and cooled to -78° C. under nitrogen. Ozone was bubbled into the reaction and after 11 minutes it was judged complete by TLC(9 hexane/1 ethyl acetate). Sodium borohydride (9.9 g, 6 eq) was added and after 5 minutes the reaction was allowed to warm to room temperature. The methanol was removed in vacuo. The residue was suspended in ether (800 mL). The ether was washed with water, and the aqueous backwashed with ether. The combined organics were washed with brine, dried (Na2SO$_4$), filtered and concentrated in vacuo to give an oil. The material was passed through a silica pad with 5% ethyl acetate/hexane followed by elution of the product with 25% ethyl acetate/hexane to provide 11.0 g (50% yield) of the alcohol, 1-(tert-butyldimethylsilyloxy)-3-(2-(hydroxy) ethoxy)-4-(tert-butyldiphenyl)-butane as a light yellow oil. MS. NMR.

To an anhydrous ether (200 mL) solution of the alcohol, 1-(tert-butyldimethylsilyloxy)-3-(2-(hydroxy)ethoxy)-4-(tert-butyldiphenyl)-butane, (11.0 g, 21.9 mmol) under nitrogen at 5° C. was added triethylamine (4.6 mL, 1.5 eq) and methanesulfonyl chloride (2.5 mL, 1.5 eq). After 1.5 hours the reaction was complete by TLC (5% ethyl acetate/ dichloromethane). The reaction was diluted with ether (250 mL), washed with water (2×), brine (2×), dried ($Na_2SO_4$), filtered and concentrated in vacuo to give an oil. The material was passed through a silica pad eluting with 5% ethyl acetate/hexane followed by 25% ethyl acetate/hexane to provide 11.6 g (91% yield) of the mesylate, 1-(tert-butyldimethylsilyloxy)-3-(2-(methanesulfonyloxy)ethoxy)-4-(tert-butyldiphenyl)-butane as an oil. MS. NMR.

To an acetone (300 mL) solution of the mesylate, 1-(tert-butyldimethylsilyloxy)-3-(2-(methanesulfonyloxy)ethoxy)-4-(tert-butyldiphenyl)-butane, (11.6 g, 20 mmol) under nitrogen was added sodium iodide (44 g, 15 eq) and sodium bicarbonate (170 mg, 0.1 eq). The mixture was refluxed for 18 hours followed by removal of the acetone in vacuo. The resulting residue was suspended in ether, washed with water (2×), and the aqueous backwashed with ether. The combined ether portions were washed with 10% sodium sulfite solution, brine (2×), dried ($MgSO_4$), filtered and concentrated in vacuo to provide 10.7 g (87% yield) of the title iodide as an oil which was used without further purification. MS. NMR.

PREPARATION 26

1-(2-(methylsulfonyloxy)-ethoxy)-2-((methylsulfonyloxy)ethyl)-3-(tert-butyldiphenylsilyloxy)-propane To a stirred solution of dimethyl allyl malonate (34 g, 0.2 mol) in t-butyl alcohol (0.5 L) was added solid sodium borohydride (19 g, 0.5 mol). The reaction was heated (70 ° C.) and methanol (162 mL) was added dropwise over a period of 1 hour. The mixture was stirred overnight at room temperature. Water (20 mL) was added to destroy the excess borohydride. The resulting mixture was filtered through celite. The filterate was concentrated (100 mL), and extracted with ethyl acetate (20 mL×4). The combined extracts were dried over $MgSO_4$ and concentrated under reduced pressure to afford relatively clean diol, 2-allylpropan-1,3-diol, (19 g, 83% yield) that was carried over to next reaction without any further purification.

To a stirred solution of diol, 2-(2-propen-1-yl)propan-1, 3-diol, (23.2 g, 0.19 mol) in toluene (1 L) was added anisaldehyde (27.3 g, 0.20 mol) and PPTS acid (4 g, 10 mol%). The flask was equipped with a Dean Stark trap, and the reaction mixture was refluxed. After 5 hours, the reaction mixture was cooled to room temperature, diluted with ether (1 L), washed with sat. $NaHCO_3$ (50 mL×3), water (50 mL×3), and brine (50 mL). The organic layer was dried over $MgSO_4$, and concentrated under reduced pressure to give a residue. The residue was eluted through a short silica gel column with 10% ethyl acetate in hexane and evaporation of the eluting solvent gave the anisylidene, 1,3-O-anisylidene-2-(2-propen-1-yl)propane (40 g, 89%). ($R_f$=0.62 (25% ethyl acetate in hexane))

To a stirred mixture of anisylidene, 1,3-O-anisylidene-2-(2-propene-1-yl)propane (20.0 g, 85.3 mmol) in $CH_2Cl_2$ (500 mL) and pH 7.0 buffer (25 mL) at 0° C. was added DDQ (38.7 g, 170.7 mmol). The reaction mixture was stirred vigorously and allowed to warm up to room temperature. After 12 hours, the reaction was diluted with ether (1L), washed with sat. aq. $NaHCO_3$ (200 mL×2), and 10% aq. $Na_2SO_3$ (200 mL ×3), dried, and concentrated under reduced pressure to a residue. The residue was eluted through a silica gel column with ethyl acetate/hexane (10%–25% ethyl acetate gradient) and evaporation of the eluting solvent gave the anizoate containing alcohol, 3-O-(4-methoxybenzoate)-2-(2-propen-1-yl)-propan-1-ol (12.7 g, 61%). ($R_f$=0.14 (25% ethyl acetate in hexane). NMR.

To a stirred solution of alcohol, 3-O-(4-methoxybenzoate)-2-(2-propene-1-yl)-propan-1-ol, (16.58 g, 66.32 mmol) in $CH_2Cl_2$ (250 mL) was added trichloroallyl imidate (24.80 g, 132.64 mmol) in cyclohexane (500 mL). To this mixture was added trifluoroacetic acid (1 mL) under a $N_2$ atmosphere. After 12 hours a white precipitate had formed. The reaction was filtered. The filterate was diluted with ether (500 mL), washed with water (100 mL×3), and brine (100 mL), dried, and concentration under reduced pressure to a residue. The residue was eluted through a silica gel column with ethyl acetate/hexane (0%–25% ethyl acetate gradient). The diene, 1-(2-propene-1-oxy)-2-(2-propen-1-yl)-3-O-(4-methoxybenzoate)-propane (24 g) containing some acetamide was taken to next step without any further purification. ($R_f$=0.38 (25% ethyl acetate in hexane)

The ester, 1-(2-propene-1-oxy)-2-(2-propene-1-yl)-3-O-(4-methoxybenzoate)-propane, (24 g) was dissolved in THF (60 mL) and methanol (100 mL) and 1N aqueous NaOH (40 mL) was added. The resulting mixture was stirred overnight followed by removal of methanol and THF under reduced pressure. The concentrated reaction mixture was diluted with ether (250 mL), extracted with ether (100 mL×3), dried, and concentrated under reduced pressure to give a residue. The residue was eluted through a silica gel column with 10% ethyl acetate/hexane and evaporation of the eluting solvent gave the alcohol, 1-(2-propene-1-oxy)-2-(2-propene-1-yl)-propan-3-ol (4.10 g, 30% for 2 steps). NMR. $R_f$=0.23 (25% ethyl acetate in hexane)

To a stirred $CH_2Cl_2$ (150 mL) solution of alcohol, 1-(2-propene-1-oxy)-2-(2-propene-1-yl)-propan-3-ol (4.10 g, 26.2 mmol) was added imidazole (2.70 g, 39.7 mmol) under a $N_2$ atmosphere. After the imidazole had dissolved tert-butylchlorodiphenylsilane (8.24 g, 29.97 mmol) in $CH_2Cl_2$ (50 mL) was added over 10 minutes. After stirring 12 hours, the reaction was diluted with ether (100 mL) quenched with water (100 mL), and extracted with ether (100 mL×3). The combined organic phase was washed with brine (100 mL), dried, and concentrated under reduced pressure to give a residue. The residue was eluted through a short silica gel column with ethyl acetate/hexane (0% to 25% ethyl acetate gradient) and evaporation of the eluting solvent gave the silyl ether, 1-(2-propene-l-oxy)-2-(2-propene-l-yl)-3-(tert-butyldiphenylsilyloxy)-propane (7.41 g, 72% yield). $R_f$=0.76 (25% ethyl acetate in hexane).

Ozone was bubbled through a −78 °C. methanol (500 mL) solution of diene, 1-(2-propene-1-oxy)-2-(2-propene-1-yl)-3-(tert-butyldiphenylsilyloxy)-propane, (7.41 g, 18.80 mmol). After the disappearance of the starting material (TLC, 25% ethyl acetate/hexane), the reaction mixture was purged with $N_2$ and sodium borohydride (2.13 g, 56.30 mmol) was added. The reaction was warmed to room temperature. After 12 hours, the reaction was concentrated. The white residue was quenched with water, and extracted with ethyl acetate (100 mL×3). The combined organic phase was washed with brine, dried, and concentrated under reduced pressure to give a residue. The residue was eluted through a short silica gel column with ethyl acetate/hexane (10% to 50% ethyl acetate gradient) and evaporation of the eluting solvent gave the 1,7-diol, 1-(2-hydroxyethoxy)-2-(2-hydroxyethyl)-3-(tert-butyldiphenylsilyloxy)-propane (5.48 g, 72% yield). $R_f$=0.21 (50% ethyl acetate in hexane). NMR.

To a stirred $CH_2Cl_2$ (400 mL) solution of diol, 1-(2-hydroxyethoxy)-2-(2-hydroxyethyl)-3-(tert-butyldiphenylsilyloxy)-propane (5.48 g, 13.6 mmol) under $N_2$ atmosphere was added TEA (11.2 mL, 78 mmol), followed by dropwise addition of methane sulfonyl chloride (3 mL, 39.00 mmol) in $CH_2Cl_2$ (100 mL) over a period of 30 minutes. After 12 hours, the reaction was diluted with ether (500 mL), washed with water (100 mL×3), brine (100 mL), dried, and concentrated under reduced pressure to a residue. The residue was eluted through a short silica gel column with ethyl acetate/hexane (10% to 50% ethyl acetate gradient) and evaporation of the eluting solvent gave the bismesylate, 1-(2-(methylsulfonyloxy)-ethoxy)-2-((methylsulfonyloxy)ethyl)-3-(tert-butyldiphenylsilyloxy)-propane (7.40 g, 97%). $R_f$=0.55 (50% ethyl acetate in hexane). NMR.

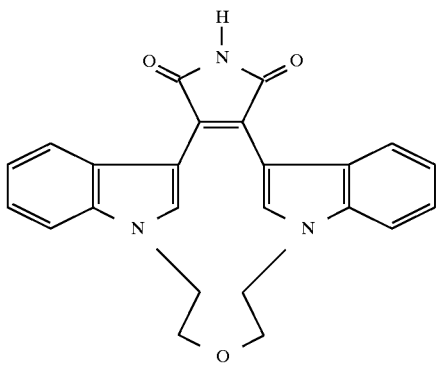

EXAMPLE 1

3,4-[(N,N'-1,1'-pethoxyethyl)-bis-(3,3'-indolyl)]-1H-pyrrole-2,5-dione.

Sodium hydride (60 percent dispersion in mineral oil, 113 mg, 2.82 mmol) was added in portions over 15 minutes to a solution of 3,4-bis(3'-indolyl)furan-2,5-dione (337 mg, 1.02 mmol) in 5 mL of dry DMF under $N_2$. The mixture was stirred 1.5 hours and then diluted with 5 mL of DMF. Bis 2,2'-dibromo-ethyl ether (0.14 mL, 1.13 mmol) was added dropwise to the green solution. The reaction mixture was stirred for 30 minutes at 25° C. and then heated at 50° C. overnight. The cooled mixture was poured into dilute aqueous citric acid (75 mL) and extracted with EtOAc (2×40 mL). The combined organic extracts were washed with water (3×20 mL) and brine (20 mL), and dried over anhydrous $MgSO_4$. The solvent was removed under reduced pressure. The residue was passed through a short column of silica gel (50 percent EtOAc/hexanes), and then subjected to radial preparative-layer chromatography (Chromatotron) eluting with 50 percent EtOAc-hexanes to afford 82 mg (20 percent) of 2,3-[(N,N'-1,1'-ethoxyethyl)-bis-(3,3'-indolyl)]-1H-furan-2,5-dione as a burgundy solid, M. Pt.>320° C.

A solution of 2,3-[(N,N'-1,1'-ethoxyethyl)-bis-(3,3'-indolyl)]-1H-furan-2,5-dione (58 mg, 0.15 mmol) in DMF (1.5 mL) under $N_2$ was treated with a mixture of 1,1,1,3,3,3,-hexamethyldisilazane (0.33 mL, 1.45 mmol) and $CH_3OH$ (23 mg, 0.73 mmol) (premixed 10 minutes). After stirring for 16 hours at room temperature, the mixture was poured into water (20 mL) and extracted with EtOAc (3×5 mL). The combined organic extracts were washed several times with water, dried ($MgSO_4$) and concentrated. The residue was purified by radial chromatography eluting with 3 percent $CH_3OH$ in $CHCl_3$ to afford 3,4-[(N,N'-1,1'-ethoxyethyl)-bis- (3,3'-indolyl)]-1H-pyrrole-2,5-dione (41.5 mg, 72 percent) as a violet solid, M. Pt.>320° C. MS Calculated for $C_{24}H_{19}N_3O_3$: 397.1426.
Found: 397.1438.

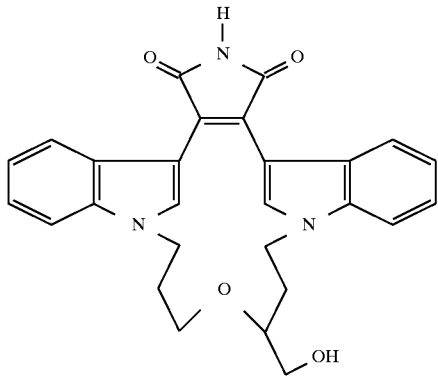

EXAMPLE 2

3,4-[(N,N'-1,1'-((3"-propoxy-3'"(O)-4'"(hydroxy) butane)-bis-(3,3'-indolyl)]-1(H)-pyrrole-2,5-dione To a stirred DMF (125 mL) solution of bis-(3,3'-indolyl)]-1-(methyl)-pyrrole-2,5-dione (4.35 g, 12.8 mmol) containing cesium carbonate (8.31 g, 25.5 mmol) was added dropwise over 15 minutes a DMF (20 mL) solution of 1-(tert-butyldimethylsilyloxy)-3-(3-iodopropyloxy)-4-(tert-butyldiphenylsilyloxy)-butane (4.0 g, 6.4 mmol) under $N_2$. After 3 hours, TLC (1:1 ethyl acetate/hexane) indicated consumption of the starting iodide. The reaction was diluted with ethyl acetate (200 mL) and washed with water. The aqueous layer was extracted with ethyl acetate (200 mL); and the combined organic layers were dried and concentrated. The concentrate was purified by flash chromatography eluting with 10% to 25% ethyl acetate/hexane to give the desired monoalkylated product 3-[(N-1-(3-propoxy-3 (O)-4-tert-butyldiphenylsilyloxy-1-tert-butyldimethylsilyloxy)-butane]-4-(3'-indolyl)-1(Methyl)-pyrrole-2,5-dione 3.94 g (69% yield) as a red oil. MS To a methanol (100 mL) solution of the above alkylation product (3.14 gr., 3.74 mmol) was added toluenesulfonic acid (60 mg, 2%). After 2 hours, TLC (50% ethyl acetate/hexane) indicated consumption of the starting material. The reaction was concentrated to half the volume, diluted with ethyl acetate (300 mL), washed with 1N NaOH, brine, dried, and concentrated. The concentrate was purified by eluting through a pad of silica with 50% ethyl acetate/hexane to give the desired alcohol 3-[(N-1-(3-propoxy-30-4-tert-butyldiphenylsilyloxy-butan-1-ol]-4-(3'-indolyl)-1(Methyl)-pyrrole-2,5-dione 1.76 g (65% yield) as a red foam. MS To a 0° C. ether solution (200 mL) of the above alcohol 3-[(N-1-(3-propoxy-30-4-tert-butyldiphenylsilyloxy-butan-1-ol]-4-(3'-indolyl)-1(methyl)-pyrrole-2,5-dione (1.76 g, 2.4 mmol) was added triethylamine (0.5 mL, 1.5 eq), followed by mesyl chloride (0.28 mL, 1.5 eq). The reaction was brought to room temperature and was complete after 1 hour. The reaction was diluted with ether (200 mL), washed with water, brine, dried, and concentrated. The concentrate was passed through a pad of silica eluting with 50% ethyl acetate/hexane, to give the mesylate product which was used immediately.

To an acetone (250 mL) solution of the above mesylate was added sodium iodide (3.6 g, 10 eq) and $NaHCO_3$ (20 mg). After stirring 4 hours, starting material still existed (TLC, 50% ethyl acetate/hexane) and additional amount of sodium iodide (10 eq) was added, and the reaction was heated at 60° C. After 4 hours, the starting material was consumed (TLC, 50% ethyl acetate/hexane). The reaction was concentrated, diluted with ethyl acetate (250 mL), washed with water, 10% sodium sulfite, dried, and concentrated. The concentrate was purified by passage through a pad of silica gel eluting with 50% ethyl acetate/hexane to give the desired iodide as an oil 3-[(N-1-(3-propoxy-3(O)-4-tert-butyldiphenylsilyloxy-1-iododbutane]-4-(3'-indolyl)-1(methyl)-pyrrole-2,5-dione 1.71 g (85% yield). MS A DMF (10 mL) solution of the above iodide 3-[(N-1-(3-propoxy-3(O)-4-tert-butyldiphenylsilyloxy-1-iododbutane]-4-(3'-indolyl)-1(methyl)-pyrrole-2,5-dione (2.0 g, 2.4 mmol) was added slowly by syringe pump over 80 hours to a DMF (400 mL) slurry of cesium carbonate (3.12 g, 9.6 mmol). After 3 hours from completion of the addition, TLC (50% ethyl acetate/hexane) indicated consumption of the starting material. The reaction was diluted with ethyl acetate (1 L) washed with water and brine. The aqueous portion was extracted with ethyl acetate (500 mL). The combined organic layers were concentrated and the concentrate was purified by passage through a pad silica eluting with (50% ethyl acetate/hexane). Concentration of the eluant gave the desired macrocycle 3,4-[(N,N'-1,1')-((3"-propoxy)-3'"(O)-4'"(hydroxy)butane-bis-(3,3'-indolyl)]-1 (methyl)-pyrrole-2,5-dione 1.65 g (97% yield). MS To an ethanol (100 mL) solution of the above N-methyl maleimide, 3,4-[(N,N'-1,1')-((3'-propoxy)-3'"(O)-4'" (hydroxy)butane)-bis-(3,3'-indolyl)]-1(methyl)-pyrrole-2,5-dione (1.7 g, 2.4 mmol) was added 5N KOH (50 mL). After 12 hours, the reaction was heated at 50° C. for 2 hours. The reaction was cooled to room temperature, concentrated, diluted with ethyl acetate, and washed with water. The organic phase was dried and concentrated to give the desired anhydride 2,3-[(N,N'-1,1'-(3'-propoxy-3'"(O)-4'"-hydroxybutane)-bis-(3,3'-indolyl)]-furan-1,4-dione 1.37 g (83% yield) as a red solid. MS To a DMF (100 mL) solution of the above anhydride 2,3-[(N,N'-1,1'-((3"-propoxy)-3'"-(O)-4'"-(hydroxy)-butane)-bis-(3,3'-indolyl)]-furan-1,4-dione (1.37 g, 3 mmol) was added 1,1,1,3,3,3-hexamethyldisilazane (12.6 mL, 20 eq) and methanol (1.21 mL, 10 eq). After 24 hours, the starting material had been completely consumed (TLC, 50% ethyl acetate/hexane). The reaction was diluted with ethyl acetate, washed with 1N HCl, water, dried, and concentrated. The concentrate was stirred in 1N HCl or with cesium fluoride to remove residual TMS group. The reaction was diluted with ethyl acetate, washed with water, dried, and concentrated to give the desired maleimide, 3,4-[(N,N'-1,1')-((3"-propoxy)-3'"(O)-4'"-(hydroxy)butane)-bis-(3,3'-indolyl)]-1(H)-pyrrole-2,5-dione 1.02 g (75% yield) as a red solid. MS 1H-NMR: (300 MHz in d6-DMSO): 2.1 (m, 4H), 2.4 (m, 2H), 3.28 (br, m), 3.4 (m, 1H), 4.25 (m, 4H), 4.5 (t, J=6 Hz, 1H), 7.0–7.9 (m, 10H), 11.0 (s, 1H)

13C-NMR:(75 MHz in d6-DMSO): 20.9, 28.9, 30.3, 30.9, 34.3, 40.2, 41.6, 42.4, 62.4, 65.9, 78.1, 104.0, 104.1, 110.0, 110.1, 119.6, 119.7, 121.4, 121.8, 24.8, 126.5, 126.6, 127.9, 131.5, 131.6, 131.7, 135.8, 135.9, 139.1, 151.4, 172.2

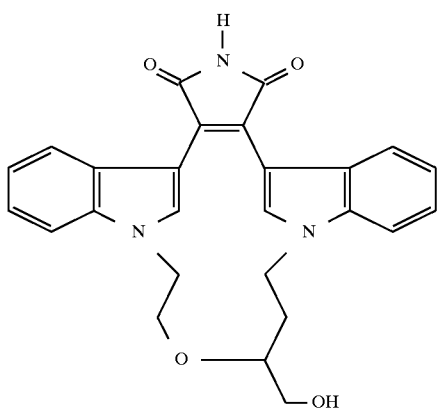

EXAMPLE 3

3,4-[(N,N'-1,1'-((2"-ethoxy)-3'"(O)-4'"-(hydroxy)-butane)-bis-(3,3'-indolyl)]-1(H)-pyrrole-2,5-dione To a dimethylformamide (250 mL) solution of bis-(3,3'-indolyl)-1-(methyl)-pyrrole-2,5-dione (17.9 g, 52.5 mmol, 3 eq) under nitrogen was added cesium carbonate (68.4 g, 4 eq). To the resulting suspension was added the iodide, 1-(tert-butyldimethylsilyloxy)-3-(2-iodoethoxy)-4-(tert-butyldiphenylsilyloxy)-butane, (10.7 g, 17.5 mmol). The reaction stirred for 18 hours at room temperature. TLC (5% ethyl acetate/hexane) showed disappearance of the iodide. The reaction was poured into ethyl acetate (1200 mL) and washed with 1N HCl (400 mL) followed by backwash with ethyl acetate (2×). The combined ethyl acetate portions were washed with saturated sodium bicarbonate solution, brine (2×), dried (MgSO$_4$), filtered and concentrated down in vacuo. Dimethylformate was removed by azeotroping in xylene. The resulting red gum was slurried in dichloromethane and acetonitrile to give a solid suspension. It was concentrated down, more dichloromethane added, cooled and filtered to give a red solid. Some of the desired product was extracted from this solid by another trituration in dichloromethane and then in ethyl acetate. The filtrates were concentrated in vacuo and the resulting residue absorbed on silica and applied to a large flash column. Dialkylated by-product was removed by elution with 5 hexane/1 ethyl acetate followed by elution of the product with 3 hexane/1 ethyl acetate to provide 8.2 g (57%) of the monoalkylated product, 3-[N-1-(2-ethoxy-(3'"-(O)-4'"-(tert-butyldiphenylsilyloxy)-1'"-(tert-butyldimethylsilyloxy)-butane))-indol-3-yl]-4-[indol-3-yl]-1N(methyl)-pyrrole-2,5-dione. MS. NMR.

To a methanol (450 mL) solution of the tert-butyldimethylsilyl ether, 3-[(N-1-(2-ethoxy-(3'"-(O)-4'"-(tert-butyldiphenylsilyloxy)-1'"-(tert-butyldimethylsilyloxy)-butane))-indol-3-yl]-4-[indol-3-yl]-1N(methyl)-pyrrole-2,5-dione (8.2 g, 9.9 mmol) under nitrogen at 5° C. was added p-toluenesulfonic acid, monohydrate (0.16 g, 0.085 eq). After 2 hours, TLC (50% ethyl acetate/hexane) showed the reaction to be nearly complete. The reaction was quenched with solid sodium bicarbonate (0.14 g). The methanol was removed in vacuo. The resulting residue was dissolved in ethyl acetate, washed with 0.1N sodium hydroxide, brine (2×), dried (MgSO$_4$), filtered and concentrated in vacuo to give a red foam. This material was absorbed on silica and placed on a silica pad. Elution with 2 hexane/1 ethyl acetate removed residual starting material followed by elution with 1 hexane/1 ethyl acetate and 1 hexane/2 ethyl acetate to provide 6.4 g(91%) of the alcohol, 3-[(N-1-(2-ethoxy-(3'"-(O)-4'"-(tert-butyldiphenylsilyloxy)-1'"-(hydroxy)-butane))-indol-3-yl]-4-[indol-3-yl]-1N (methyl)-pyrrole-2,5-dione. MS. NMR.

To an anhydrous ether (500 mL) solution of the alcohol, 3-[(N-1-(2-ethoxy-(3'"-(O)-4'"-(tert-butyldiphenylsilyloxy)-1'"-(hydroxy)-butane))-indol-3-yl]-4-[indol-3-yl]-1N (methyl)-pyrrole-2,5-dione (6.36 g, 8.9 mmol) under nitrogen at 5° C. was added triethylamine (1.9 mL, 1.5 eq) and methanesulfonyl chloride (1.0 mL, 1.5 eq). After 3 hours, additional triethylamine (1.25 mL, 1.0 eq) and methanesulfonyl chloride (0.7 mL, 1.0 eq) were added. After 1 hour, the reaction was shown to be complete by TLC (50% ethyl acetate/hexane). The reaction was diluted with ether (250 mL), washed with water, 0.1N HCl and brine (2×). The ether was dried (MgSO$_4$), filtered, and concentrated in vacuo to provide 7.0 g of mesylate, 3-[(N-1-(2-ethoxy-(3'"-(O)-4'"-(tert-butyldiphenylsilyloxy)-1'"-(methanesulfonyloxy)-butane))-indol-3-yl]-4-[indol-3-yl]-1N(methyl)-pyrrole-2,5-dione. MS.

To an acetone (200 mL) solution of the mesylate, 3-[(N-1-(2-ethoxy-(3'"-(O)-4'"-(tert-butyldiphenylsilyloxy)-1'"-(methanesulfonyloxy)-butane))-indol-3-yl]-4-[indol-3-yl]-1N(methyl)-pyrrole-2,5-dione, (7.0 g, 8.9 mmol) under nitrogen was added sodium iodide (13.3 g, 10 eq) and sodium bicarbonate (75 mg, 0.1 eq). The mixture was stirred at 50° C. for 13 hours. The reaction was concentrated in vacuo, and the residue was dissolved in ether and washed with 10% sodium sulfite solution. The layers were separated, and the ether portion washed with 10% sodium sulfite solution, water, brine(2×), dried, and concentrated in vacuo. The residue was passed through a silica pad by eluting with 1 hexane/1 ethyl acetate and 1 hexane/2 ethyl acetate to provide 7.6 g of the iodide, 3-[(N-1-(2-ethoxy-(3'"-(O)-4'"-(tert-butyldiphenylsilyloxy)-1'"-(iodo)-butane))-indol-3-yl]-4-[indol-3-yl]-1N(methyl)-pyrrole-2,5-dione as a red solid (quantitative yield for the two steps). MS. NMR.

To a dimethylformamide (1 L) suspension of cesium carbonate (12.0 g, 4 eq) under nitrogen was added the iodide, 3-[(N-1-(2-ethoxy-(3'"-(O)-4'"-(tert-butyldiphenylsilyloxy)-1'"-(iodo)-butane))-indol-3-yl]-4-[indol-3]-1(methyl)-pyrrole-2,5-dione (7.6 g, 9.2 mmol), dissolved in dimethylformamide(25 mL) via syringe pump over 65 hours. Three hours after the addition was complete, the reaction was concentrated in vacuo. The residue was dissolved in ethyl acetate (700 mL), washed with water (2×300 mL), and the aqueous layer backwashed with ethyl acetate (2×200 mL). The combined ethyl acetate portions were washed with brine (2×200 mL), dried (MgSO$_4$), filtered and concentrated in vacuo to provide a purple residue. The material was absorbed onto silica and applied to a flash column. Eluted with 3 hexane/1 ethyl acetate and then 1hexane/1 ethyl acetate to give 5.2 g(82%) of the macrocycle, 3,4-[(N,N'-1,1'-((2"-ethoxy)-3'"(O)-4'"-(tert-butyldiphenylsilyloxy)-butane)-bis-(3,3'-indolyl)]-1(H)-pyrrole-2,5-dione. MS. NMR.

A suspension of the N-methyl maleimide, 3,4-[(N,N'-1,1'-((2"-ethoxy)-3'"(O)-4'"-(tert-butyldiphenylsilyloxy)-butane)-bis-(3,3'-indolyl)]-1(H)-pyrrole-2,5-dione in 5N KOH (150 mL) and ethanol (300 mL) was stirred at room temperature for 65 hours and then for one hour at 60° C. The reaction was concentrated (150 mL) in vacuo, the residue suspended in water, cooled to 5 ° C, and acidified (pH 3) with concentrated hydrochloric acid. The red aqueous suspension was extracted with ethyl acetate (4×200 mL), dried, and concentrated in vacuo to give 3.3 g of the crude anhydride alcohol, 2,3-[(N,N'-1,1'-((2"-ethoxy)-3'"(O)-4'"-(hydroxy)-butane)-bis-(3,3'-indolyl)]-furan-1,4-dione as a purple solid. MS.

To a dimethylformamide (250 mL) solution of the anhydride, 2,3-[(N,N'-1,1'-((2"-ethoxy)-3'"(O)-4'"-(hydroxy)-butane)-bis-(3,3'-indolyl)]-furan-1,4-dione, (3.3 g, 7.5 mmol) under nitrogen was added 1,1,1, 3, 3, 3 -hexamethyldisilazane (32 mL, 2 eq) and methanol (3 mL, 10 eq). The reaction was stirred at room temperature for 16 hours and then heated at 60° C. for 2 hours. The dimethylformamide was removed in vacuo, and the resulting residue was dissolved in acetonitrile (250 mL). 1N HCl (50 mL) was added. The reaction was stirred for 15 minutes. The reaction was concentrated, partitioned between ethyl acetate (1 L) and water (250 mL). The product was a solid that precipitated giving the alcohol maleimide, 3,4-[(N,N'-1,1'-((2"-ethoxy)-3'"(O)-4'"-(hydroxy)-butane)-bis-(3,3'-indolyl)]-1(H)-pyrrole-2,5-dione, 0.92(28%) of product. A small amount (50 mg) was absorbed on silica and applied to a flash column. Eluted with dichloromethane, 5% acetonitrile/dichloromethane and then 10% acetonitrile/dichloromethane to give 38 mg of analytically pure material. The ethyl acetate was concentrated and chromatographed to give an additional 8% of the crude product. MS.

$^1$H NMR (d$_6$-DMSO): δ1.96 (1H, m); 2.09 (1H, m); 3.31 (1H, m); 3.40 (1H, m); 3.51 (1H, m); 3.62 (1H, m); 3.89 (1H, m); 4.18 (3H, m); 4.35 (1H, m), 4.68 (1H, t, J=2 Hz); 7.11 (2H, m); 7.19 (2H, m); 7.44 (1H, s) 7.46 (1H, d, J=9 Hz); 7.51 (1H, s) 7.53 (1H, d, J=9 Hz); 7.79 (1H, d, J=8 Hz); 7.83 (1H, d, J=8 Hz); 10.91 (1H, s).

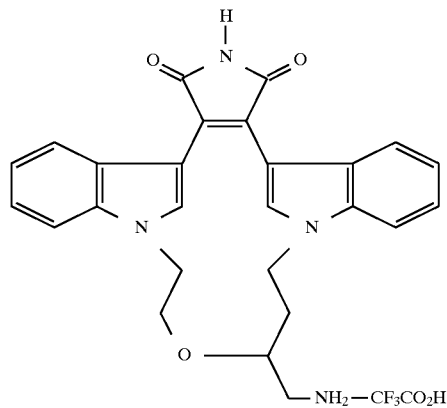

EXAMPLE 4

3,4-[(N,N'-1,1'-((2'-ethoxy)-3'"(O)-4'"-(amino)-butane)-bis-(3,3'-indolyl)]-1(H)-pyrrole-2,5-dione trifluoroacetate salt To an anhydrous tetrahydrofuran (15 mL) solution of the alcohol, 3,4-[(N,N'-1,1'-((2"-ethoxy)-3'"(O)-4'"-(hydroxy)-butane)-bis-(3,3'-indolyl)]-1(H)-pyrrole-2,5-dione, (155 mg, 0.35 mmol) under nitrogen was added 2, 4, 6-collidine (280 μL, 3 eq). The solution was cooled to –78° C. and treated with trifluoromethanesulfonic anhydride (118 μL, 2 eq). After 1.5 hours at –78° C., a large excess of concentrated ammonium hydroxide (2 mL) was added. After 10 minutes, the reaction was warmed to –42° C. with a dry ice/acetonitrile bath and then stirred for 18 hours while allowing to warm to room temperature. The reaction was concentrated in vacuo. The resulting residue was dissolved in ethyl acetate (400 mL), washed with water, brine, dried, and concentrated in vacuo to provide the crude primary amine. The amine was absorbed on silica and applied to a flash column which was sequentially eluted with 1 ethyl acetate/i hexane, ethyl acetate, ethyl acetate/5% methanol and finally 50 ethyl acetate/45 acetonitrile/4 methanol/2 isopropylamine to elute the amine, 3,4-[(N,N'-1,1'-((2"-ethoxy)-3'"(O)-4'"-(amino)-butane)-bis-(3,3'-indolyl)]-1(H)-pyrrole-2,5-dione (38 mg). Starting alcohol (104 mg, 67%) was also recovered. The product was further purified using reverse phase size exclusion chromatography by eluting with 85 acetonitrile/15 (0.01% TFA/water). The collected fractions azeotroped with ethyl acetate to give 23 mg(12%) of a powder as the TFA salt. MS.

$^1$H NMR (d$_6$-DMSO): δ1.99 (1H, m); 2.08 (1H, m); 2.82 (1H, m); 3.18 (1H, m); 3.57 (2H, m); 3.75 (1H, m); 4.13 (2H, m); 4.29 (1H, m); 4.44 (1H, m); 7.09 (2H, t, J=7 Hz); 7.18 (2H, t, J=7 Hz); 7.47 (4H, m); 7.70 (3H, bs); 7.78 (2H, m)

In a analogous manner the S-enantiomer, 4s as the HCl salt, and the R-enantiomer, 4r as the HCl salt, were prepared.

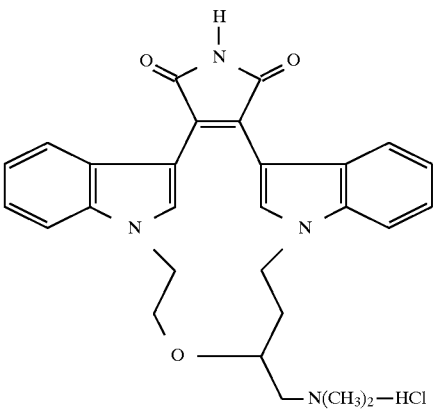

EXAMPLE 5

3,4-[(N,N'-1,1'-((2"-ethoxy)-3'"(O)-4'"-(N,N-dimethylamino)-butane)-bis-(3,3'-indolyl)]-1(H)-pyrrole-2,5-dione HCl Salt To an anhydrous dichloromethane (140 mL) suspension of the alcohol, 3,4-[(N,N'-1,1'-((2"-ethoxy)-3'"(O)-4'"-(hydroxy)-butane)-bis-(3,3'-indolyl)]-1(H)-pyrrole-2,5-dione, (472 mg, 1.07 mmol) under nitrogen was added pyridine (260 μL, 3 eq) and methanesulfonic anhydride (242 mg, 1.3 eq). After 4 hours, the reaction was diluted with dichloromethane, washed with 0.1N HCl (2×) and filtered to remove starting material (54 mg). The dichloromethane portion was washed with brine (2×), dried, and concentrated to give the crude mesylate, as a purple solid. The material was absorbed on silica and applied to a flash column which was sequentially eluted with dichloromethane, 5% acetonitrile/dichloromethane and 10% acetonitrile/dichloromethane to provide 288 mg (52% yield) of the mesylate, 3,4-[(N,N'-1,1'-((2"-ethoxy)-3'"(O)-4'"-(methanesulfonyloxy)-butane)-bis-(3,3'-indolyl)]-1(H)-pyrrole-2,5-dione. MS. NMR.

To a tetrahydrofuran (20 mL) solution of the mesylate, 3,4-[(N,N'-1,1'-((2"-ethoxy)-3'"(O)-4'"-(methanesulfonyloxy)-butane)-bis-(3,3'-indolyl)]-1(H)-pyrrole-2,5-dione, (304 mg, 0.59 mmol) was added a 8.9M solution of dimethylamine in tetrahydrofuran (7 mL, 100 eq). After heating (65° C.) for 24 hours in a sealed tube, the reaction was diluted with ethyl acetate (200 mL), washed with brine (2x), dried, and concentrated to provide the crude dimethylamine derivative as a solid. The material was absorbed on silica and applied to a flash column that was sequentially eluted with 3 ethyl acetate/1 hexane, ethyl acetate and 2% isopropylamine/ethyl acetate to give the dimethylamine derivative 193 mg (70% yield) which was 90% pure by HPLC. The dimethylamine derivative, 3,4-[(N,N'-1,1'-((2"-ethoxy)-3'"(O)-4'"-(N,N-dimethylamino)-butane)-bis-(3,3'-indolyl)]-1(H)-pyrrole-2,5-dione,was purified to greater than 95% as the triflouroacetate salt using reverse phase size exclusion HPLC by eluting with 85 acetonitrile/15 (0.01%TFA/water).

The triflouroacetate salt of 3,4-[(N,N'-1,1'-((2 "-ethoxy)-3'"(O)-4'"-(N,N-dimethylamino)-butane)-bis-(3,3'-indolyl)]-1(H)-pyrrole-2,5-dione was converted to the HCl salt by suspending the salt in ethyl acetate and washing gently with 0.1N NaOH(5x50 mL). The ethyl acetate portion was washed with brine (2x), dried, and concentrated to provide the free base, 3,4-[((N,N'-1,1'-((2"-ethoxy)-3 '"(O)-4'"-(N,N-dimethylamino)-butane)-bis-(3,3'-indolyl)]-1(H)-pyrrole-2,5-dione. To an anhydrous methanol (50 mL) suspension of the free base, 3,4-[(N,N'-1,1'-((2"-ethoxy)-3'"(O)-4'"-(N,N-dimethylamino)-butane)-bis-(3,3'-indolyl)]-1(H)-pyrrole-2, 5-dione was added 1N HCl in anhydrous ether (13 mL, 50 eq). The ether was evaporated, and the residue was dried under vacuum to give 143 mg (52% yield) of 3,4-[(N,N'-1, 1'-((2"-ethoxy)-3'"(O)-4'"-(N,N-dimethylamino)-butane)-bis-(3,3'-indolyl)]-1(H)-pyrrole-2,5-dione hydrochloride salt as a red solid. MS.

$^1$H NMR (d$_6$-DMSO): δ2.03 (1H, m); 2.26 (1H, m); 2.68 (6H, t, J=5 Hz); 3.24 (1H, m); 3.28, (1H, m, after D$_2$O shake); 3.64 (1H, m); 3.77 (2H, m); 4.07–4.38 (4H, m); 7.08 (2H, m); 7.17 (2H, m); 7.43 (3H, m); 7.52 (1H, d, J=8 Hz); 7.79 (2H, m); 10.33 (1H, bs); 10.92 (1H, s)

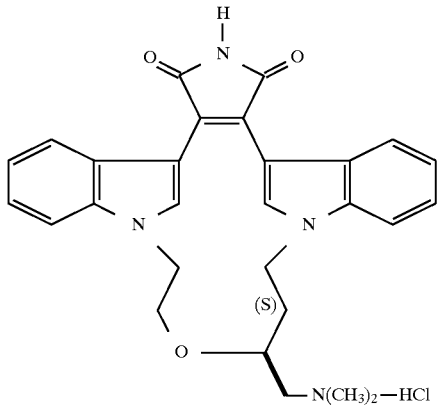

EXAMPLE 5s (S)-3.4-[(N,N'-1,1'-((2"-ethoxy)-3'"(O)-4'"-(N,N-dimethylamino)-butane)-bis-(3,3'-indolyl)1-1(H)-pyrrole-2,5-dione Hydrochloride Salt To a THF (300 mL) solution of the mesylate, (S)-3,4-[(N,N'-1,1')-((2"-ethoxy)-3'"-(O)-4"-(methanesulfonyloxy)-butane)-(bis)-(3-indolyl)]-1H-pyrrole-2,5-dione (2.8 g, 5.39 mmol) was added dimethylamine (100 mL, 40% in water) in a sealed vessel. After heating (50° C.) for 24 hours, the reaction was concentrated. The residue was passed through a pad of silica eluting with ethyl acetate and then with 10% triethylamine/ethyl acetate which eluted the desired (S)-dimethylamine derivative. The eluant was concentrated to yield 1.7g (67% yield) of the free base (S)-3,4-[(N,N'-1,1'-((2"-ethoxy)-3'"(O)-4'"-(N,N-dimethylamino)-butane)-bis-(3,3'-indolyl)]-1(H)-pyrrole-2,5-dione as a violet solid. The free base was converted to the hydrochloride salt by suspending the free base 3,4-[(N,N'-1,1')-(4"-N,N-dimethylamino-3-(S)-"ethoxybutane)]-(bis)-(3-indolyl)-1H-pyrrol-2,5-dione (1.7 g, 3.6 mmol) in methanol (300 mL) and adding 1.0N anhydrous HCl in ether (10 mL, 10 mmol). After 0.5 hours at ambient temperature, the bright orange precipitate was collected, washed with ether, and dried under vacuum to yield 1.4 g (77% yield) of 3,4-[(N,N'-1,1')-(4"-N,N-dimethylamino-3-(S)-"ethoxybutane)]-(bis)-(3-indolyl)-1H-pyrrol-2,5-dione hydrochloride salt. MS.

$^1$H NMR: (d6-DMSO)δ 2.1 (m, 1H); 2.35 (m, 1H); 2.68 (s, 6H); 3.2 (m, 1H,); 3.33 (m, 1H); 3.66 (br. t, 1H); 3.8 (br. t, 1H); 3.85 (m, 1H); 4.17 (m, 1H); 4.2–4.4 (m, 3H); 7.1 (d, 1H); 7.13 (d, 1H); 7.2 (m, 2H); 7.44 (s, 1H); 7.48 (s, 1H); 7.5 (d, 1H); 7.56 (d, 1H); 7.82 (br.t, 2H); 10.59 (br., 1H); 10.96 (s, 1H).

EXAMPLE 5r (R)-3,4-[(N,N'-1,1-((2"-ethoxy)-3'"(O)-4'"-(N,N-dimethylamino)-butane)-bis-(3,3'-indolyl)]-1(H)-pyrrole-2 ,5-dione Hydrochloride Salt The R enantiomer was prepared in an identical manner as the (S) enantiomer, except using the (R)-4-tert-butyldiphenylsilyloxy-3-(2-iodoethoxy)-1-iodobutane as a starting material. MS. NMR.

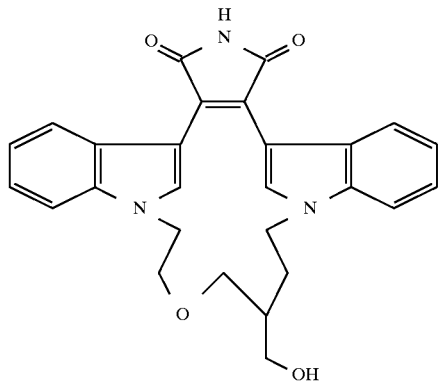

EXAMPLE 6

3,4-[(N,N'-1,1'-(2"-ethoxy-(3'"((O)-methylene)-4'"-(hydroxy)-butane)-bis-(3,3'-indolyl)]-1(H)-pyrrole-2, 5-dione A dry DMF (100 mL) solution of (bis)mesylate, 1-(2-(methylsulfonyloxy)-ethoxy)-2-((methylsulfonyloxy)ethyl)-3-(tert-butyldiphenylsilyloxy)-propane, (7.40 g, 13.30 mmol) and bis-(3,3'-indolyl)]-1(methyl)-pyrrole-2,5-dione (4.43 g, 13.30 mmol) was added over 16 hours to a stirred suspension of Cs$_2$CO$_3$ (25.4 g, 78 mmol) in DMF (400 mL) at 50° C. After 8 hours, the reaction was concentrated under reduced pressure at 80° C. to give a residue. The residue was diluted with ethyl acetate (200 mL), washed with water (50 mL). The organic layer was separated, and the aqueous layer was extracted with ethyl acetate (50 mL×3). The combined organic portion was dried, and concentrated to a residue. The residue was eluted through a column of silica gel with 25% ethyl acetate in hexane followed by 5% methanol in CH$_2$Cl$_2$ to give three predominant products: The silyl ether macrocycle product, 2,3-[(N,N'-1,1'-(4'''-ethoxy-1'-yl-(3'''-(tert-butyldiphenylsilyloxy)methylene)butan-1-yl)-bis-(3,3'-indolyl)]-1(methyl)-pyrrol-1,4-dione, (2.35 g) MS: Calculated for $C_{44}H_{45}N_3O_4Si$:Mol. mass: 707.31, found 708, $R_f$=0.84 (50% ethyl acetate in hexane), the desilylated alcohol macrocycle product (600 mg). MS.

To a stirred EtOH (500 mL) solution of N-methyl macrocycle, 2,3-[(N,N'-1,1'-(4'''-ethoxy-1'-yl-(3'''-(tert-butyldiphenylsilyloxy)methylene)butan-1-yl)-bis-(3,3'-indolyl)]-1(methyl)-pyrrol-1,4-dione, (1.65 g, 2.33 mmol) was added 5N KOH (100 mL). After 12 hours at 50° C., the reaction mixture was cooled to room temperature and concentrated under reduced pressure to a residue. The residue was acidified with concentrated HCl to pH 1 and extracted with ethyl acetate (200 mL×5). The combined organic phase was dried, concentrated under reduced pressure, and was eluted through a short silica column with 5% methanol in dichloromethane. Evaporation of the eluting solvent gave a residue containing the anhydride, 2,3-[(N,N'-1,1'-(4'''-ethoxy-1'-yl-(3'''-(tert-butyldiphenylsilyloxy)methylene)butan-1-yl)-bis-(3,3'-indolyl)]-furan-1,4-dione that was used in the next reaction.

To a dry DMF (250 mL) solution of anhydride, 2,3-[(N,N'-1,1'-(4'''-ethoxy-1'-yl-(3'''-(tert-butyldiphenylsilyloxy)methylene)butan-1-yl)-bis-(3,3'-indolyl)]-furan-1,4-dione, (600 mg, 1.3 mmol) was added HMDS (2.1 g, 13 mmol) followed by methanol (209 mg, 6.5 mmol). After 48 hours, the reaction was concentrated, and the residue dissolved in ethyl acetate (100 mL), washed with 1N aq HCl (25 mL), water (25 mL) and brine (25 mL) respectively. The resulting organic phase was then dried and concentrated to give a residue. The residue was eluted through a column of silica gel with methanol/$CH_2Cl_2$ (0% to 5% methanol). Evaporation of the eluting solvent gave the imide, 3,4-[(N,N'-1,1'-(2''-ethoxy-(3'''((O)-methylene)-4'''-(hydroxy)-butane )-bis-(3,3'-indolyl)]-1(H)-pyrrole-2,5-dione, as a solid (300 mg, 50% yield). MS.

$^1$H NMR (CDC13) δ 9.65 (s, 1H), 7.79 (t, J=7.65 Hz), 7.61 (s, 1H), 7.54 (s, 1H), 7.46–7.40 (m, 2H), 7.24–7.08 (m, 2H), 7.07–7.02 (m, 2H). 4.43–4.33 (m, 2H), 4.30–4.21 (m, 1H), 4.14–4.06 (m, 1H), 3.64 (t, J=4.64 Hz), 3.58–3.38 (m, 5H), 3.71 (t, J=8.64 Hz, 1H), 1.89–1.85 (m, 1H)

(hydroxy)-butane)-bis-(3,3 '-indolyl)]1(H)-pyrrole-2,5-dione (140 mg, 0.30 mmol) containing pyridine (120 mg, 1.5 mmol) was added methane sulfonic anhydride (106 mg, 0.61 mmol) under a $N_2$ atmosphere. After 12 hours, the reaction was quenched with water (25 mL), diluted with $CH_2Cl_2$ (50 mL), washed with 0.2N HCl (20 mL×2), aq sodium bicarbonate (20 mL), water (20 mL), brine (20 mL), dried, and concentrated to a residue. The residue was eluted through a short silica gel column with 5% methanol in dichloromethane and evaporation of the eluting solvent gave the mesylate, 3,4-[(N,N'-1,'-(2''-ethoxy-(3'''((O) -methylene) -4'''-(methanesulfonyloxy)-butane)-bis-(3,3'-indolyl)]-1(H)-pyrrole-2,5-dione that was used in the next reaction.

To a sealed tube THF (20 mL) solution of mesylate, 3,4-[(N,N'-1,1'-(2''-ethoxy-(3'''((O)-methylene)-4'''-(methanesulfonyloxy)-butane)-bis-(3,3'-indolyl)]-1(H)-pyrrole-2,5-dione, (157 mg, 0.29 mmol) was added pyrrolidene (203 mg, 2.90 mmol). After heating (50° C.) for 12 hours, the reaction was cooled to room temperature concentrated under reduced pressure, dissolved in $CH_2Cl_2$ (50 mL), washed with water (20 mL×2), brine (20 mL), dried, and concentrated under reduced pressure to a residue. The residue was eluted through a short silica gel column with 5% methanol in dichloromethane and evaporation of the eluting solvent gave the pyrrolidine, 3,4-[(N,N'-1,1'-(2''-ethoxy-(3''' ((O)-methylene)-4'''-(N-pyrrolidino)-butane)-bis-(3,3'-indolyl)]-1(H)-pyrrole-2,5-dione, MS: calculated for $C_{31}H_{32}N_4O_3$:Mol mass: 508.62, found 508, $R_f$=0.14 (5% methanol in dichloromethane, trace triethylamine). The pyrrolidine was further purified by reverse phase gel permeation chromatography to give the pyrrole macrocycle as the triflouroacetic acid salt (55 mg, 37% yield). The triflouroacetic acid salt of the pyrrole was converted to the hydrochloride titled compound by extracting a 1N NaOH (5 mL) slurry of the trifluoroacetic acid salt (55 mg) with ethyl acetate (25 mL)/methanol (2 mL), the extract was dried, and concentrated to a residue. The residue was slurried in ether/methanol (10:1) and a HCl solution of ether was added. After 30 minutes, the slurry was concentrated and dried in vacuo to give the title compound (48 mg, 88% yield). MS.

$^1$H NMR: δ 10.98 (s, 1H), 7.90 (s, 1H), 7.82 (s, 1H), 7.70–7.62 (m, 3H), 7.56–7.50 (m, 1H), 7.24–7.02 (m, 4H), 4.50–4.20 (m, 4H), 3.76–3.42 (m, 4H), 2.82–2.44 (m, 4H), 2.26–2.24 (m, 1H), 1.82–1.60 (m, 6H), 1.26–1.02 (m, 2H).

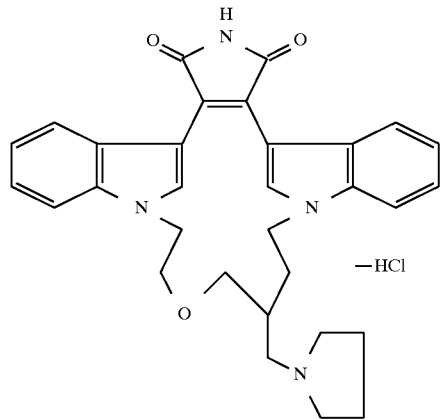

EXAMPLE 7

3,4-[(N,N'-1,1'-(2''-ethoxy-(3'''((O)-methylene)-4'''-(N-pyrrolidino)-butane)-bis-(3,3 '-indolyl)]-1(H)-pyrrole-2,5-dione hydrochloride salt To a dry $CH_2C_2$ (50 mL) solution of imide alcohol, 3,4-[(N,N'-1,1'-(2''-ethoxy-(3'''((O)-methylene)-4'''-

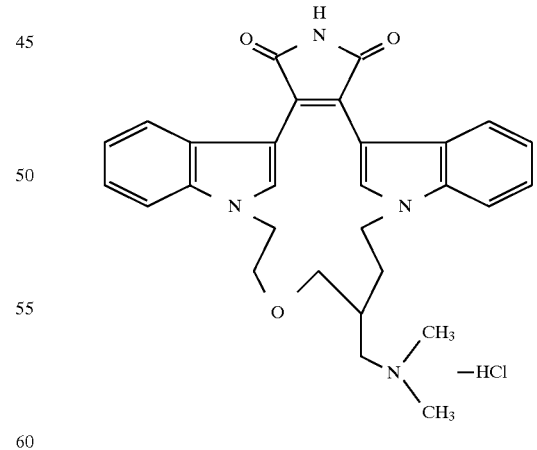

EXAMPLE 8

3,4-[(N,N'-1,1'-(2''-ethoxy-(3'''((O)-methylene)-4'''-(N,N-dimethylamino)-butane)-bis-(3,3'-indolyl)]-1 (H)-pyrrole-2,5-dione hydrochloride salt The titled tertiary amine was prepared by displacement of the mesylate with dimethylamine (58 mg, 75% yield). MS.

¹H (CDCl₃) d 10.93 (s, 1H), 7.84 (s, 1H), 7.77 (s, 1H), 7.69–7.64 (m, 3H), 7.47 (d, J=7.97 Hz, 1H), 7.13–7.02 (m, 4H), 4.40–4.11 (m, 4H), 3.73–3.20 (m, 4H), 2.50 (s, 3H), 2.33 (s, 1H), 2.13–1.96 (m, 2H), 1.86–1.70 (m, 1H), 1.21–1.10 (m, 2H)

The following compounds were prepared in a manner analogous to the Examples described herein and further illustrate the compounds of the invention. In the following examples, the structure of the compound was confirmed by NMR, MS, and/or elemental analysis. During the synthesis, R is a protected hydroxy, preferably a silyl ether preferably tert-butyldiphenylsilyloxy (TBDPS). The silyl ether may be converted to a leaving group and substituted to produce the following examples:

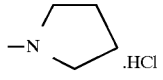

| Example | n | n1 | n2 | R |
|---|---|---|---|---|
| 9 | 3 | 2 | 0 | —NH₂ |
| 10 | 3 | 2 | 0 | —NH₂.HCl |
| 11 | 3 | 2 | 0 | —N(CH₃)₂.HCl |
| 12 | 3 | 2 | 0 | 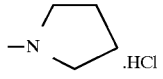 |
| 13 | 3 | 2 | 0 | —NHCH₂C₆H₅.HCl |
| 14 | 3 | 2 | 0 | —NHCOCH₃ |
| 15 | 3 | 2 | 0 | —NHSO₂C₆H₅ |
| 16 | 3 | 2 | 0 | —NHC(O)OCH₂C₆H₅ |
| 17s S-enantiomer | 2 | 2 | 0 | —NHCH₃.HCl |
| 18s S-enantiomer | 2 | 2 | 0 | —NHCH₂C₆H₅.HCl |
| 18r R-enantiomer | | | | |
| 19r R-enantiomer | 2 | 2 | 0 | —NHCOCH₃ |
| 20r R-enantiomer | 2 | 2 | 0 | 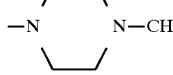 |
| 20s S-enantiomer | | | | |
| 21r R-enantiomer | 2 | 2 | 0 | —NHSO₂C₆H₅ |
| 21s S-enantiomer | | | | |
| 22 | 2 | 2 | 0 | —NHCH₂(pyridyl).HCl |
| 23s S-enantiomer | 2 | 2 | 0 | 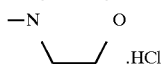 |
| 24s S-enantiomer | 2 | 2 | 0 | —N︵O.HCl |
| 25r R-enantiomer | 2 | 2 | 0 | —NHC(O)OCH₂C₆H₅ |

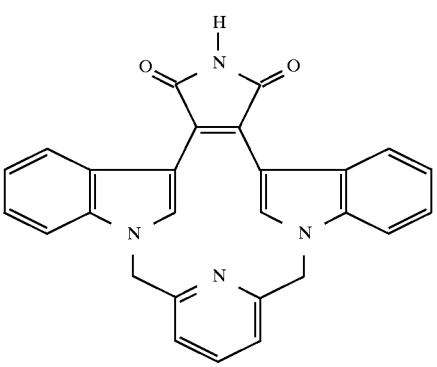

EXAMPLE 26

3,4-[N,N'-1,1'-(2-methylene-6-methylenepyridine)-bis-(3,3'-indolyl)]-1H-pyrrole-2,5-dione.

Following the same procedure as described in Example 1, 2,3-bis-indolemaleic anhydride (287 mg, 0.88 mmol in 5 mL DMF was treated with sodium hydride (60 percent in oil, 88 mg, 2.19 mmol) for 1.5 hours, then diluted to 11 mL with DMF, and treated with bis-2,6-dibromomethyl pyridine (245 mg 0.93 mmol). After stirring at 50° C. overnight, the reaction mixture was worked up (EtOAc) and filtered through a short plug of silica (50 percent EtOAc in hexanes). N,N'-(2,6-Pyridine-bridged)-bis-indolemaleic anhydride (142 mg, 37 percent) was obtained as a dark-red solid, which showed essentially a single spot on TLC analysis and was used directly in the next step without further purification.

3,4-[N,N'-1,1'-(2-methylene,6-methylenepyridine)-bis-(3,3'-indolyl)-1H-furan-2,5-dione (140 mg, 0.32 mmol) in 2 mL of DMF was treated with a mixture of 1,1,1,3,3,3-hexamethyldisilazane (0.72 mL, 3.2 mmol) and CH₃OH (0.063 mL, 1.6 mmol) to give, after workup and purification by radial chromatography on silica gel, 42 mg of the titled, N,N'-(2,6-pyridine-bridged)-bis-indolemaleimide, as a burgundy solid. This material was homogeneous by TLC (Rf= 0.35, 3 percent CH₃OH in CHCl₃).

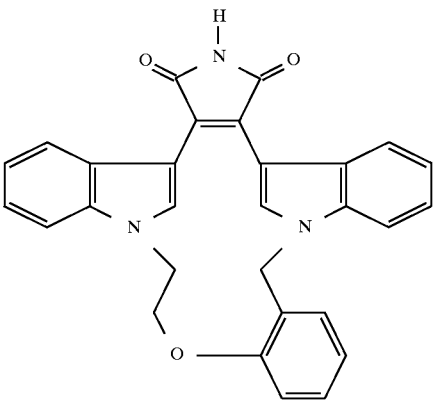

EXAMPLE 27

3,4-[(N,N'-1,1'-(2"-ethoxy)-benzyl)-bis-(3,3'-indolyl)]-1(H)-pyrrole-2,5-dione hydrochloride A dry DMF (45 mL) solution of dibromide, 2-(2'-Bromoethoxy)-benzylbromide, (2.0 g, 6.8 mmol) and bis- (3,3'-indolyl)]-1(methyl)-pyrrole-2,5-dione (2.3 g, 6.8 mmol) was added via syringe pump over 20 hours to a suspension of Cs$_2$CO$_3$(8.9 g, 27 mmol) in dry DMF (550 mL) with vigorous stirring at 55° C. under N$_2$. After an additional 2 hours, the reaction mixture was concentrated in vacuo, the residue dissolved in CH$_2$Cl$_2$, washed with 1N HCl, brine, dried, and concentrated in vacuo to give a violet oil. The oil was passed through a plug of silica eluting with 1:1 hexanes/ethyl acetate. The eluant was reduced to yield the macrocycle, 3,4-[(N,N'-1'-(2"-ethoxy)-benzyl)-bis-(3,3'-indolyl)]-1(methyl)-pyrrole-2,5-dione 2.76 g (71% yield) as a magenta solid. Recrystallization from isopropanol/methylene chloride gave analytically pure material. MS: MW=473; observed 473, FD, CHCl$_3$), EA: Calculated (observed): C 76.09 (75.86); H 4.90 (4.93), N 8.87 (8.79).

To an ethanol (100 mL) suspension of macrocycle, 3,4-[(N,N'-1,1'-(2"-ethoxy)-benzyl)-bis-(3,3'-indolyl)]-1(methyl)-pyrrole-2,5-dione (710 mg, 15 mmol) containing THF (20 mL) was added 5N KOH (80 mL). The reaction was heated (55° C.) for 70 hours with stirring, cooled to room temperature, and the ethanol removed in vacuo. The concentrate was acidified to pH 1 with 5N HCl (325 mL), extracted with ethyl acetate, washed with brine (2×), dried, and concentrated to give the anhydride, 3,4-[(N,N'-1,1'-(2"-ethoxy)-benzyl)-bis-(3,3'-indolyl)]-furan-2,5-dione 700 mg (quantitative conversion) as a residue.

To a dry DMF (500 mL) solution of the anhydride, 3,4-[(N,N'-1,1'-(2"-ethoxy)-benzyl)-bis-(3,3'-indolyl)]-furan-2,5-dione (760 g, 17 mmol), was added a solution of methanol (0.34 mL, 8.3 mmol) and 1,1,1,3,3,3-hexamethyldisilazane (3.5 mL, 17 mmol). After heating (55° C.) 22 hours the reaction was concentrated in vacuo, diluted with ethyl acetate, washed with 0.1N HCl. The combined organic layer was dried, and concentrated to a violet residue. The residue was applied to a short plug of silica and eluted with CH$_2$Cl$_2$/hexane (gradient 0–100% CH$_2$Cl$_2$). Evaporation of the eluting solvent gave the NH maleimide, 3,4-[(N,N'-1,1'-(2"-ethoxy)-benzyl)-bis-(3,3'-indolyl)]-1(H)-pyrrole-2,5-dione 483 mg (70% yield) as a purple solid. The title compound was crystallized from CH$_2$Cl$_2$/hexane. MS.

$^1$H NMR: (DMSO-d$_6$) δ 4.29 (2H, bs); 4.59 (2H, bs); 5.23 (2H, bs); 6.90–6.99 (2H), 7.01–7.18 (3H), 7.20–7.27 (2H), 7.59–7.68 (2H), 7.71–7.80 (5H); 10.92 (H, s).

mmol) in portions of 30 minutes. The resultant green solution was stirred 1 hour. The mixture was diluted with 10 mL of DMF and then treated dropwise with 1,6-dibromohexane (0.24 mL, 1.57 mmol). The reaction mixture was stirred 30 minutes at room temperature and then heated at 45° C. for 16 hours. The cooled mixture was poured into dilute aqueous NH$_4$Cl (125 mL) and extracted with EtOAc (3×40 mL). The combined organic extracts were washed with water and dried (MgSO$_4$). After removal of the solvent in vacuo, the residue was purified by flash chromatography on silica gel eluting with CH$_2$C$_{12}$-hexanes, 1:1 to 3:1 (gradient elution) to afford compound 3,4-[(N,N'-1,1'-hexane)-bis-(3,3'-indolyl)]-1-methyl-pyrrole-2,5-dione (137 mg, 22 percent) as a purple solid, M. Pt.>320° C.

A mixture containing 3,4-[(N,N'-1,1'-hexane)-bis-(3,3'-indolyl)]-1-methyl-pyrrole-2,5-dione (137 mg, 322 mmol), ethanol (15 mL), 5N KOH (5 mL) and THF (2 mL) was stirred 4 hours at room temperature. At that time TLC analysis showed the starting material to be consumed. The mixture was diluted with water (15 mL) and concentrated on the rotary evaporator. The mixture was cooled, acidified to pH 1 with 3N HCl and extracted with CH$_2$Cl$_2$ (3×10 mL). The combined organic extracts were washed well with water, dried over anhydrous MgSO4 and concentrated. The purple solid obtained (116 mg) was found by NMR analysis to be a 4:1 mixture of the desired anhydride and starting material. This material was used directly in the next step without further purification.

In the same manner as that described in Example 1, a solution of 3,4-[(N,N'-1,1'-hexane)-bis-(3,3'-indolyl)-furan-2,5-dione (108 mg, 0.263 mmol) in DMF (1.5 mL under N$_2$ was treated with a mixture of 1,1,1,3,3,3-hexamethyldisilazane (0.59 mL, 2.62 mmol) and CH$_3$OH (0.05 mL, 1.31 mmol) overnight. After workup (EtOAc), the crude product was subjected to flash chromatography on silica gel (CH$_2$Cl$_2$-EtOAc, 10:1–5:1, gradient elution) to afford two colored fractions. The first colored fraction to eluate contained the 3,4-[(N,N'-1,1'-hexane)-bis-(3,3'-indolyl)-1-methyl-pyrrole-2,5-dione impurity carried from the previous reactions. The second colored fraction contained the desired product, 3,4-[(N,N'-1,1'-hexane)-bis-(3,3'indolyl)-1H-pyrrole-2,5 dione (56 mg). M. Pt.>320° C. MS Calculated for C$_{26}$H$_{23}$N$_3$O$_2$ (0.3 H$_2$O):
C, 76.26; H, 5.66, N, 10.26.
Found:
C, 75.21; H, 5.65; N, 10.05.

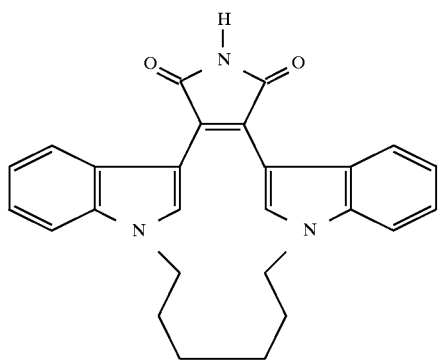

EXAMPLE 28

3,4-[(N,N'-1,1'-hexane)-bis-(3,3'-indolyl)]-1H-pyrrole-2,5-dione.

To a solution of 3,4-bis-(3-indolyl)-1-methyl-pyrrole-2,5-dione (499 mg, 1.46 mmol) in 10 mL of DMF under N$_2$ was added sodium hydride (60 percent in oil, 146 mg, 3.65

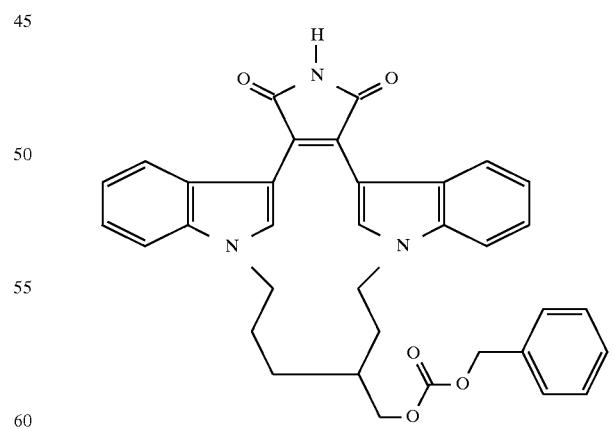

EXAMPLE 29

3,4-[(N,N'-1,1'-(3"-(benzylcarbonate)methylene) hexane)-bis-(3,3'-indolyl)]-1H-pyrrole-2,5-dione.

To a 0° C. dichloromethane solution of 3,4-[(N,N'-1,1'-(3"-(hydroxy)methylene)hexane)-bis-(3,3'-indolyl)]-1H- pyrrole-2,5-dione (24 mg, 0.054 mmol) was added diisopropylethylamine (10.6 mg, 0.081 mmol) followed by benzyl chloroformate (13.8 mg, 0.081 mmol). After 72 hours, the reaction mixture was quenched with 2.5N sodium bicarbonate; the organic layer removed; and the aqueous layer extracted with dichloromethane. The combined organic layers were combined, washed with brine, dried over magnesium sulfate, filtered and concentrated to give an oil that was purified by reverse phase HPLC (5% acetonitrile in water with 0.1% TFA gradient to 100% acetonitrile on C18 column) to give 6 mg of the title compound. MS.

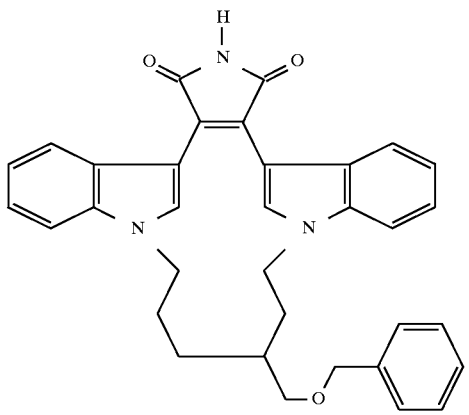

EXAMPLE 30

(±)-3,4-[(N,N'-1,1'-(3"-(benzyloxymethylene) hexane)-bis-(3,3'-indolyl)]-1H-pyrrole-2,5-dione Following the same procedure as described in the previous examples, 3,4-bis-(3'-indolyl)-1-methyl-pyrrole-2,5-dione (400 mg, 1.17 mmol) in 8 mL DMF was treated with sodium hydride (60 percent in oil, 117 mg, 2.93 mmol) followed by treatment with (±)-3-benzyloxymethylene-1,6-dibromohexane in 7 mL of DMF. After heating at 50° C. overnight, the crude product after workup was purified by flash chromatography on silica gel eluting with $CH_2Cl_2$-hexanes, 1:1–2:1 (gradient-elution) to give pure (±)-3,4-[(N,N'-1,1'-(3"-(benzyloxy methylene)hexane)-bis-(3,3'-indolyl)]-1-methyl-pyrrole-2,5-dione (149 mg 23 percent) as a violet solid.

A mixture containing (±)-3,4-[(N,N'-1,1'-(3"-benzyloxy methylene)hexane)-bis-(3,3'-indolyl)-1-methyl-pyrrole-2,5-dione (141 mg, 0.259 mmol), ethanol 15 mL and 5N KOH (5 mL) was stirred at room temperature for 3 hours at which time TLC analysis showed the starting material to be consumed. After acidification and extraction with $CH_2Cl_2$, the crude product (101 mg) showed two spots on TLC analysis ($CH_2Cl_2$) corresponding to starting material and desired anhydride (±)-3,4-[(N,N'-1,1'-(3"-benzyloxy methylene) hexane)-bis-(3,3'-indolyl)-furan-2,5-dione. NMR analysis indicated roughly a 4:1 mixture of anhydride and starting material respectively. This material was used directly in the next step without further purification.

(±)-3,4-[(N,N'-1,1'-(3"-Benzyloxymethylene)hexane)-bis-(3,3'-indolyl)-furan-2,5-dione (98 mg, 0.180 mmol) in 1 mL DMF was treated with a mixture of 1,1,1,3,3,3-hexamethyldisilazane (0.41 mL, 1.80 mmol) and $CH_3OH$ (0.036 mL, 0.90 mmol) at 25° C. overnight. The mixture was worked-up (EtOAc) and flash chromatographed on silica gel eluting with $CH_2C_{12,}$ $CH_2Cl_2$-EtOAc 10:1 (gradient elution) to give 30 mg of purified (±)3,4-[N,N'-1,1'-(3"-(benzyloxy) methylene)-hexane)-bis-(3,3'-indolyl)-1H-pyrrole-2,5-dione. M. Pt. 171°–173° C. MS

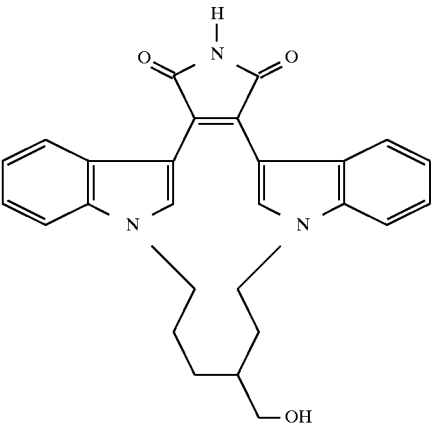

EXAMPLE 31

3,4-[(N,N'-1,1'-(3"-hydroxy)methylene)hexane)-bis-(3,3'-indolyl)]-1H-pyrrole-2,5-dione A mixture containing bis-(3,3'-indolyl)]-1-(methyl)-pyrrole-2,5-dione (3.41 g, 10.0 mmol) and 3-tert-butyldiphenylsilyloxymethylene-1, 6-dibromohexane (5.64 g, 11.0 mmol) in 50 mL of DMF was added with a syringe pump over 30 hours to a well-stirred solution of cesium carbonate (11.2 g, 34.3 mmol) in DMF (350 mL) at 55° C. under $N_2$. After the addition was complete, the reaction mixture was heated at this temperature an additional 16 hours. The cooled mixture was poured into 1.2 L of water containing 20 mL of 3N HCl and extracted with three 300 mL portions of $CH_2C_2$. The combined organic extracts were washed with water and brine then dried ($MgSO_4$) and concentrated. The residue was passed through a 3"×3" column of silica gel eluting with $CHCl_3$. The crude product thus obtained was purified by flash chromatography on silica gel ($CHCl_3$) to afford 2.87 g (41%) of 3,4-[(N,N'-1,1'-(3'-tert-butyldiphenylsilyloxymethylene)-hexane)-bis-(3,3'-indolyl)]-1(methyl)-pyrrole-2,5-dione as a purple solid, M. pt. 220°–224° C. HRMS calculated for $C_{44}H_{45}N_3SiO$ [M+1] : 692.3307. Found: 692.3299.

A mixture containing 3,4-[(N,N'-1,1'-(3"-tert-butyldiphenylsilyloxymethylene)-hexane)-bis-(3,3-indolyl)]-1(methyl)-pyrrole-2,5-dione ( 1.55 g, 2.22 mmol), 4N KOH (100 mL), THF (10 mL) and 95% EtOH (200 mL) was heated at 90° C. for 16 hours. After removal of most of the EtOH on the rotary evaporator, the mixture was acidified to pH 1 with 6N HCl and extracted with $CH_2Cl_2$ (3×75 mL)). The combined organic extracts were washed with water and brine and dried over anhydrous $Na_2SO_4$. After removal of the solvents in vacuo, the residue was dissolved into a minimum of 5% methanol in $CHCl_3$ and loaded onto a 3"×3" column of silica gel. Elution with $CHCl_3$ followed by 10 % methanol in $CHCl_3$ gave two fractions; evaporation of the second fraction provided 676 mg (69%) of anhydride-alcohol as a purple solid which was homogeneous by TLC (Rf=0.5, 10% methanol in $CHCl_3$). This material was used directly in the next step without further purification.

To a solution of the above anhydride (510 mg, 1.15 mmol) in DMF (11 mL) was added a premixed solution containing 1,1,1,3,3,3,- hexamethyldisilazane (5.14 mL, 23 mmol) and $CH_3OH$ (0.45 mL, 11.5 mmol). The resultant mixture was heated at 50° C. for 24 hours under N₂. The cooled reaction mixture was poured into 100 mL of water. The precipitated product was washed with water and dried overnight to give 409 mg of 3,4-[(N,N'-1,1'-(3"-hydroxymethylene)-hexane)-bis-(3,3'-indolyl)]-1H-pyrrole-2,5-dione as a reddish-purple solid. This material was found to be 93% pure by HPLC (reverse-phase) analysis and was contaminated with an unidentified compound of similar $R_f$. HRMS calculated. for $C_{27}H_{25}N_3O_3$: 439.1896. Found: 439.1911.

EXAMPLE 31r (R)-3,4-[(N,N'-1,1'-(3"-(hydroxymethylene)-hexane)-bis-(3,3'-indolyl)]-1H-pyrrole-2,5-dione Following the same procedure described above for the preparation of Example 31, (R)-3,4-[(N,N'-1,1'-(3"-hydroxymethylene)hexane-bis-(3,3'-indolyl)]-1H-pyrrole-2,5-dione was prepared in 25% overall yield from the dibromide, (R)- 3-(tert-butyldiphenylsilyloxymethylene)-1,6-dibromohexane by dialkylation of bis-(3,3'-indolyl)]-1-(methyl)-pyrrole-2,5-dione, hydrolysis, and 1-H-pyrrole-2,5-dione formation. M. pt.>300° C.

$^1$H NMR (300 MHz, DMSO-d₆) 1.05–2.25 (m, 7H) , 4.04–4.45 (m, 6H) (m, 8H), 7.08 –7.88 (m, 10 H).

EXAMPLE 31s (S)-3,4-[(N,N'-1,1'-(3"-(hydroxymethylene)-hexane)-bis-(3,3'-indolyl)]-1H-pyrrole-2,5-dione Following the same procedure described above for the preparation of Example 31, (S)-3,4-[(N,N'-1,1'-(3"-hydroxymethylene)-hexane)-bis-(3,3'-indolyl)]-1H-pyrrole-2,5-dione was prepared (4.5 g) in 39% overall yield from dibromide, (S)-3-(tert-butyldiphenylsilyloxymethylene)-1,6-dibromohexane by dialkylation of bis-(3,3'-indolyl)]-1-(methyl)-pyrrole-2,5-dione, hydrolysis, and 1-H-pyrrole-2,5-dione formation. MS.

$^1$H NMR (d₆, DMSO) δ 1.05–1.15 (2H), 1.23–1.24 (1H), 1.50–1.52 (1H), 1.71 (1H), 1.94 (1H), 2.07–2.12 (1H), 4.05–4.4 (m, 6H), 7.09–7.21 (m,4H), 7.35 (d, J=15 Hz, 2H), 7.49 (d, J=9 Hz, 2 H), 7.8 (d, J=9 Hz, 2H), 10.93 (s, 1H).

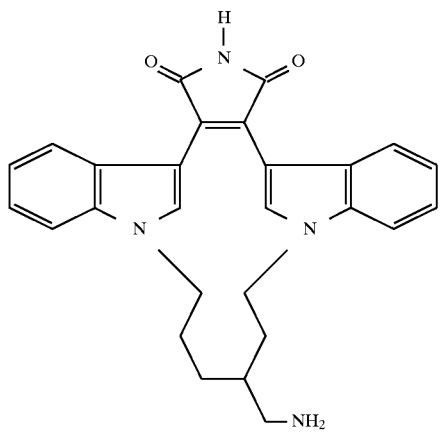

EXAMPLE 32 and 33

3,4-[(N,N'-1,'-(3"-aminomethylene)-hexane)-bis-(3,3'-indolyl)]-1H-pyrrole-2,5-dione Example 32 as the TFA salt Example 33 as the HCl Salt To a stirred solution of the anhydride alcohol 2,3-[(N,N'-1,1'-(3"-(hydroxymethylene)-hexane)-bis-(3,3'-indolyl))]-furan-1,4-dione (0.18 g, 0.41 mmol) in anhydrous dichloromethane (10 mL), under nitrogen was added triethylamine (0.10 g, 1.06 mmol), and methanesulfonylchloride (0.11 g, 0.98 mmol). The resulting solution was stirred 30 minutes at room temperature. The solvent was removed in vacuo. The residue was dissolved in 10 mL anhydrous dimethylformamide, followed by the addition of sodium azide ( 0.26 g, 4.1 mmol). The reaction mixture was heated for 1.5 hours at 50° C. under nitrogen. The cooled reaction mixture was partitioned between 0.2N HCl and ethyl acetate. The combined organic extract was dried over magnesium sulfate, filtered, and evaporated to provide 185 mg of the azide, which was used directly in the next reaction. The crude azide was dissolved in dimethylformamide (3 mL), under nitrogen, and 1,1,1,3,3,3-hexamethyldisilazane (1.25 g, 7.75 mmol) and methanol (0.12 g, 3.87 mmol) were added. The reaction was heated at 50° C. After 12 hours, the reaction was cooled, diluted with ethyl acetate, washed with water, hydrochloric acid 2N. The aqueous washes were back extracted with ethyl acetate (3×50 mL). The combined organic layers were dried over magnesium sulfate, filtered, and evaporated to provide the azide-imide, 3,4-[(N,N'-1,1'-(3"-azidomethylene)-hexane)-bis-(3,3'-indolyl)]-1H-pyrrole-2,5-dione (175 mg) as a purple colored solid. The product was chromatographed on a Rainin Dynamex $^R$-60 $C_{18}$ column (21.4×250 mm) using a linear gradient from 805 A (0.1% TFA and 5% acetonitrile in water) to 100% B (pure acetonitrile) over 60 minutes at 15 mL/min. to obtain purified 3,4-[(N,N'-1,1'-(3"-azidomethylene)-hexane)-bis-(3,3'-indolyl)]-1H-pyrrole-2,5-dione in 57% overall yield. MS. NMR.

To a solution of the azide 3,4-[(N,N'-1,1'-(3"-zidomethylene)-hexane)-bis-(3,3'-indolyl)]-1H-pyrrole-2,5-dione (0.1 g 0.21 mmol), in ethyl acetate (15 mL) and ethanol (5 mL) was added Lindlar's catalyst (0.1 g). The reaction mixture was stirred under hydrogen (1 ATM) at room temperature. After 12 hours, the catalyst was removed by filtration and the filtrate was concentrated in vacuo. Purification by preparative reverse phase HPLC on a Rainin Dynamax R- 60 C18 (21.4×250 mm) using a linear gradient 80% A (0.1 % TFA and 5% acetonitrile in water) to 100% B (pure acetonitrile) over 60 minutes at 15 mL/min., provided the primary amine as the TFA salt, 3,4-[(N,N'-1,1'-(3"-aminomethylene)-hexane)-bis-(3,3'-indolyl)]-1H-pyrrole-2,5-dione trifluoroacetic acid salt, as a solid (80 mg) in 63% yield. MS.

$^1$H NMR (d6 acetone) δ 0.77–0.78 (m, 1H), 1.0–1.1 (m, 1H), 1.27–1.34 (m,1H), 1.43 (m, 1H), 1.52–1.56 (m,4H), 1.60–1.1.68 (m,1H), 1.90–1.94 (m, 1H), 3.17–3.21 (m,1H), 3.35, 3.38 (m,1H), 3.64–3.67 (m,1H), 3.75-3.82 (m,2H), 6.61–6.72 (m, 4H), 6.824 ( d, J=16 Hz, 2H), 6.936(t, J=8.31 Hz, 2H), 7.397 (t, J=7.83 Hz, 2H), 9.3 (s, 1H).

$^{13}$C NMR (d6 acetone) δ 26.0, 28.0, 32.1, 35.4, 40.8, 41.0, 41.1, 45.1, 45.8, 50.9, 105.1, 105.2, 110.8, 111.0, 121.24, 121.29, 122.7, 122.9, 123.0, 128.4, 128.6, 131.5, 132.0, 134.0, 134.1, 136.8, 137.1, 172.6, 172.7, 192.5

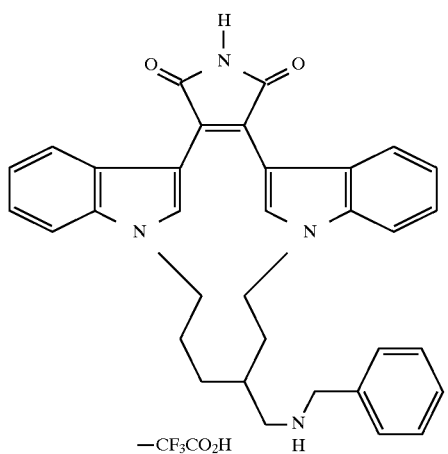

EXAMPLE 34

3,4-[(N,N'-1,1'-(3"-(N-benzylamino)methylene)-
hexane)-bis-(3,3'-indolyl)]-1H-pyrrole-2,5-dione
trifluoroacetate salt To a stirred solution of the primary amine, 3,4-[(N,N'-1, 1'-(3"-aminomethylene)-hexane)-bis-(3,3'-indolyl)]-1H-pyrrole-2,5-dione (40 mg, 0.05 mmol), in anhydrous THF (2 mL) under nitrogen was added benzaldehyde (9.39 mg, 0.08 mmol). After 30 minutes, sodium triacetoxy borohydride (18.75 mg, 0.08 mmol) was added. After stirring 1 hour, the reaction mixture was diluted with water and extracted with ethyl acetate (3×25 mL). The combined organic extracts were dried over magnesium sulfate, filtered and concentrated in vacuo. Purification by reverse phase HPLC on a Rainin Dynamax R- 60 C18 column (21.4×250 mm) using a linear gradient from 80% A ( 0.1% TFA and 5% acetonitrile in water) to 100% B (pure acetonitrile) over 60 minutes at 15 mL/min., provided two different fractions of mono benzyl compound, 3,4-[(N,N'-1,1'-(3"-(N-benzylamino) methylene)-hexane)-bis-(3,3'-indolyl)]-1H-pyrrole-2,5-dione (16 mg) in 66% yield, and the dibenzylamino compound, 3,4-[(N,N'-1,1'-(3"-(N,N-dibenzylamino) methylene)-hexane)-bis-(3,3'-indolyl)]-1H-pyrrole-2,5-dione, (7 mg) in 20% yield. MS.

$^1$H NMR (d$_6$ acetone) δ 1.1–1.3 (m, 1H), 1.5–1.6 (m,1 H ), 1.71–1.77 (m, 1H), 1.93–2.10 (m, 3H), 2.5 (m ,1H), 3.1–3.2 (m,1H), 3.37–3.41 (m,1H), 4.13 (t, J=5.1Hz, 2H ),4.28 (t, J=5.1 Hz, 2H), 4.36 (d, J=3.6 Hz, 2H), 7.13–7.24 (m, 4H), 7.33 (d, J=25 Hz, 2H), 7.39–7.51 (m,7 H), 7.89–7.96 (m,2H), 9.76 (s,1H).

$^{13}$C NMR (d$_6$ acetone) δ 25.6, 27.3, 32.1, 32.9, 44.7, 45.4, 50.1,52.2, 105.0, 105.2, 110.8, 111.1, 121.2, 121.3, 122.8, 122.9, 123.1, 128.5, 129.8, 130.3, 131.2, 131.3, 132.0, 132.4, 133.7, 134.0, 136.8, 137.0, 172.5, 172.6

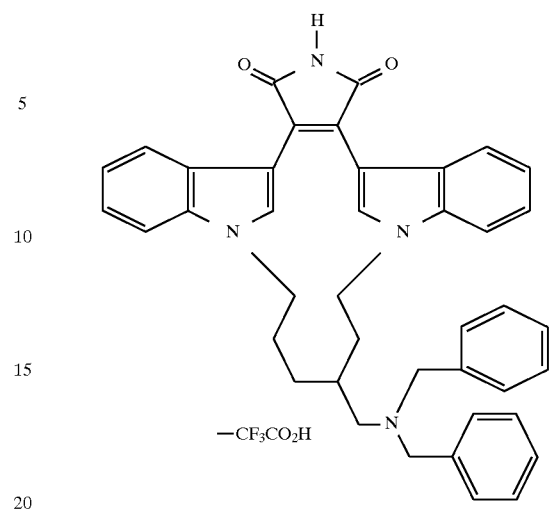

EXAMPLE 35

3,4-[(N,N'-1,1'-(3"-(N,N-dibenzylamino)methylene)-
hexane)-bis-(3,3'-indolyl)]-1H-pyrrole-2,5-dione
trifluoroacetate salt 3,4-[(N,N'-1,1'-(3"-(N,N-dibenzylamino)methylene)-hexane)-bis-(3,3'-indolyl)]-1H-pyrrole-2,5-dione was prepared in a manner analogous to Example 34. MS.

$^1$H NMR (d$_6$ acetone) δ 0.2–0.3 (m,1 H), 0.6–0.9 (m, 4 H), 1.2–1.3 (m,1H) 1.50 (d, J=5.4 Hz, 2 H), 2.27 (m,1H), 3.3–3.8 (m, 8H), 6.6–6.9 (m, 18 H), 7.35 (dd, J=7.5 Hz, J=24.9 Hz, 2 H), 9.1 (s, 1H).

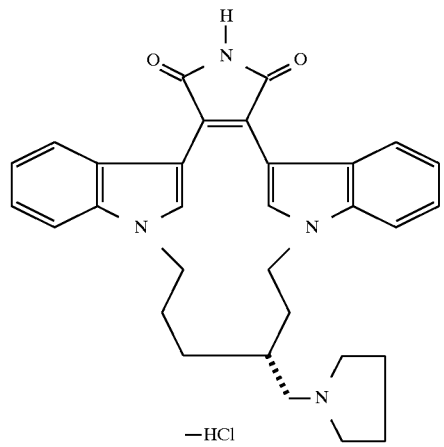

EXAMPLE 36r (R)-3,4-[(N,N'-1,1'-(3"-(N-pyrrolidino)methylene)-
hexane)-bis-(3,3'-indolyl)]-1H-pyrrole-2,5-dione
hydrochloride salt A stirred mixture of mesylate, (R)-3,4-[(N,N'-1,1'-(3'-(methanesulfonyloxy)methylene)-hexane)-bis-(3,3'-indolyl)]- 1H-pyrrole-2,5-dione, (202 mg) and pyrrolidine (1.5 mL) in THF (15 mL) was heated at 50° C. until TLC indicated the starting material be consumed (16 hours). EtOAc (30 mL) was added. The organic phase was washed with 10 mL portions of 5% NaHCO$_3$, water and brine. Concentration afforded deep-red residue which was subjected to preparative HPLC (Waters reverse-phase, 0.1 % TFA and 5% $CH_3CN$ in water—100% $CH_3CN$ gradient) to give pure (R)-3,4-[(N,N'-1,1'-(3"-N-pyrrolidinomethylene)-hexane)-bis-(3,3'-indolyl)]-1H-pyrrole-2,5-dione as its TFA salt. Conversion to HCl-salt in the same manner gave (R)-3,4-[(N,N'-1,1'-(3"-N-pyrrolidinomethylene)-hexane)-bis-(3,3'-indolyl)]-1H-pyrrole-2,5-dione hydrochloride salt (42 mg) as a light red solid. M. pt. 220° C. (dec.). HRMS calculated for $C_{31}H_{33}N_4O_2$ [M+1]: 493.2604. Found : 493.2605.

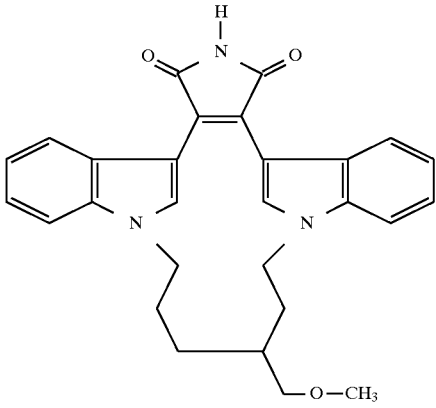

EXAMPLE 37

3.4-[(N,N'-1,1'-(3"-methoxymethylene)-hexane)-bis-(3,3'-indolyl)]-1H-pyrrole-2,5-dione A solution of 3,4-[(N,N'-1,1'-(3"-tert-butyldiphenylsilyloxymethylene)-hexane)-bis-(3,3'-indolyl)]- 1(methyl)-pyrrole-2,5-dione (1.25 g, 1.81 mmol) in THF (20 mL) was treated with a solution of tetra-n-butylammonium fluoride in THF (1M, 2.0 mL, 2.0 mmol). The mixture was stirred for 1 hour at 25 ° C. The reaction mixture was quenched with 1N HCl (5 mL) and diluted with EtOAc (75 mL). After washing with water and brine, the organic layer was dried ($MgSO_4$) and concentrated. The residue was purified by flash chromatography on silica gel eluting with 3–5% methanol in THF/hexanes (1:1) to afford alcohol, 3,4-[(N,N'-1,1'-(3"-hydroxymethylene)-hexane)-bis-(3,3'-indolyl)]-(methyl)-pyrrole-2,5-dione, 509 mg (62 %) as a purple solid. This material was used directly in the next step.

To a stirred solution containing the above alcohol (285 mg, 0.63 mmol) and 47% aqueous tetrafluoroboric acid (170 mg, 0.95 mmol) in $CH_2Cl_2$ (6 mL) at 0° C. was added dropwise a solution of trimethylsilyldiazomethane (Aldrich, 2.0M hexanes, 0.47 mL, 0.95 mmol) over 5 minutes. The resultant mixture was stirred at 0° C. for 2 hours then at 25° C. for 4 hours. TLC analysis of the reaction mixture indicated a large amount of unreacted starting material. The mixture was cooled and an equivalent additional amount of tetrafluoroboric acid trimethylsilyldiazomethane was added. The mixture was stirred 2 hours at 0° C. then 6 hours at 25° C. and diluted with $CH_2Cl_2$ (20 mL) and washed with 2N HCl (10 mL) and water (10 mL). The organic layer was dried ($MgSO_4$), concentrated. The residue was loaded onto a 3"×3" silica gel column and eluted with $CH_2Cl_2$ to give methyl ether, 3,4-[(N,N'-1,1'-(3"-methoxymethylene)-hexane)-bis-(3,3'-indolyl)]-1(methyl)-pyrrole-2,5-dione, 114 mg, (39%) as a reddish-purple solid, M.Pt. 234°–236° C. NMR.

HRMS calculated for $C_{29}H_{29}N_3O_3$: 467.2208. Found : 467.2210.

A mixture of 3,4-[(N,N'-1,1'-(3"-methoxymethylene)-hexane)-bis-(3,3'-indolyl)]-1(methyl)-pyrrole-2,5-dione (110 mg, 0.243 mmol), and 5N KOH (8 mL) in 15 mL of EtOH containing 1 mL of THF was heated at 90° C. for 24 hours. After removal of most of the ethanol under reduced pressure, the mixture was acidified to pH 1 with 6N HCl and extracted with $CH_2Cl_2$ (3×15 mL). The combined organic extracts were washed with dilute aqueous $NaHCO_3$ and water and dried over anhydrous $MgSO_4$. After removal of the solvents in vacuo, the crude product was loaded onto a 2"×2" column of silica gel and eluted with $CH_2Cl_2$ to give anhydride which was used directly in the next reaction.

To a solution of the above anhydride (76 mg, 0.17 mmol) in DMF (1.5 mL) was added a solution of 1,1,1,3,3,3-hexamethyldisilazane (0.75 mL, 3.34 mmol) and $CH_3OH$ (0.07 mL, 1.67 mmol) that had been premixed for 5 minutes The reaction mixture was stirred 1 hour at 25° C. then heated at 50° C. for 20 hours whereupon TLC analysis showed the reaction to be complete. The cooled reaction mixture was worked up (EtOAc) as previously described. The crude product was purified by flash chromatography on silica gel ($CH_2Cl_2$ —4% EtOAc in $CH_2Cl_2$, gradient elution) to afford 42 mg (55%) of 3,4-[(N,N'-1,1'-(3"-methoxymethylene)-hexane)-bis-(3,3'-indolyl)]-1H-pyrrole-2,5-dione as a dark red solid. Recrystallization from acetone-water gave 28 mg. of analytically pure 3,4-[(N,N'-1,1'-(3"-methoxymethylene)-hexane)-bis-(3,3'-indolyl)]-1H-pyrrole-2,5-dione as reddish-violet solid, M.Pt. 272°–274° C.

Analytical calculated for $C_{28}H_{27}N_3O_3$ (0.1 $H_2O$)

C, 73.86; H, 6.02; N, 9.23.
Found : C, 73.51; H, 5.92; N, 8.99.

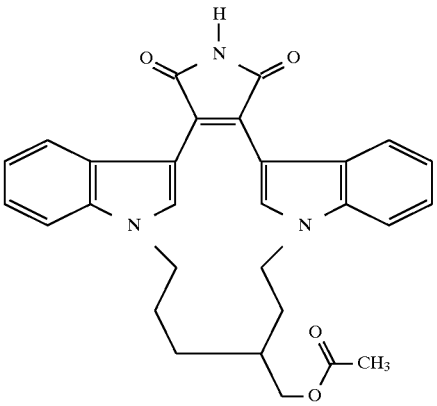

EXAMPLE 38

3,4-[(N,N'-1,1'-(3"-(acetoxy)methylene)-hexane)-bis-(3,3'-indolyl)]-1H-pyrrole-2,5-dione Acetic anhydride (0.064 mL, 0.68 mmol) was added to a stirred mixture of the anhydride, 2,3-[(N,N'-1,1'-(3"-(hydroxymethylene)-hexane)-bis-(3,3'-indolyl)]-furan-1,4-dione (1.49 mg, 0.34 mmol), 4-dimethylaminopyridine (27 mg, 0.22 mmol), pyridine (0.75 mL) and THF (1.5 mL). The reaction mixture was stirred at 25° C. under $N_2$ for 16 hours. The mixture was diluted with EtOAc (20 mL) and washed with 2N HCl (2×10 mL) and water (2×10 mL) and dried over anhydrous $MgSO_4$. After evaporation of the solvents under reduced pressure the crude product was purified by chromatography on a short column of silica gel eluting with CH₂Cl₂ to give the O-acetate anhydride, 2,3-[(N,N'-1,1'-(3"-(acetoxymethylene)-hexane)-bis-(3,3'-indolyl)]-furan-1,4-dione, 111 mg, (68%) as a purple solid, M.Pt. 252°–254° C.

To a stirred solution of the 0-acetate anhydride, 2,3-[(N,N'-1,1'-(3"-(acetoxymethylene)-hexane)-bis-(3,3'-indolyl)]-furan-1,4-dione, (103 mg, 0.22 mmol) in DMF (2 mL) was added a solution containing 1,1,1,3,3,3-hexamethyldisilazane (0.48 mL, 2.2 mmol) and CH3OH (0.043 mL, 1.1 mmol) which had been premixed for 5 minutes. The reaction mixture was worked up (EtOAc) as previously described and the crude product was purified by flash chromatography on silica gel (gradient elution: CH₂Cl₂ —5% EtOAc in CH₂Cl₂) to give the O-acetyl maleimide, 3,4[(N,N'-1,1'-(3"-(acetoxy)methylene)-hexane)-bis-(3,3'-indolyl)]-1H-pyrrole-2,5-dione 74 mg ( 72%) as a deep red solid which was homogeneous by TLC (CH2C12). Recrystallization from acetone-water provided the titled compound as a red solid. M.Pt. 250°–252° C.

Analytical calculated for $C_{29}H_{27}N_3O_4$ (0.1 $H_2O$):

C, 72.06; H, 5.67; N, 8.69.

Found: C, 71.72; H, 5.67; N, 8.29.

The following compounds were prepared in a manner analogous to the Examples described and further illustrate the compounds of the invention. In the following examples, the structure was confirmed by NMR, MS and/or elemental analysis.

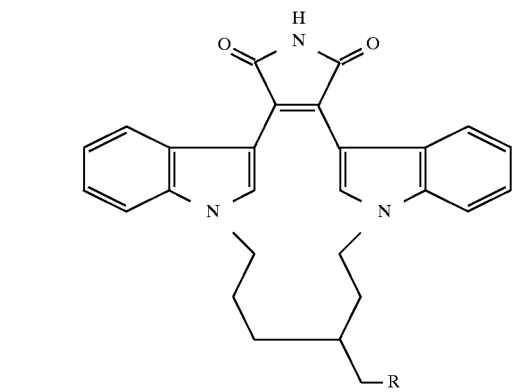

| Example | R |
|---|---|
| 39 | —NHC(O)OCH₂(C₆H₅) |
| 40 | —N(CH₃)₂·HCl |

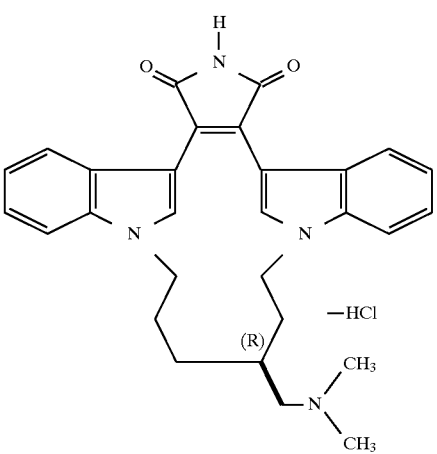

EXAMPLE 40r
(R)-3,4-[(N,N'-1,1'-(3"-(N,N-dimethylamino)methylene)-hexane)-bis-(3,3'-indolyl)]-1H-pyrrole-2,5-dione hydrochloride salt Methanesulfonic anhydride (94 mg, 0.54 mmol) was added over 10 minutes to a stirred solution of chiral alcohol, (R)-3,4-[(N,N'-1,1'-(3"-(hydroxy)methylene)-hexane)-bis-(3,3'-indolyl)]-1H-pyrrole-2,5-dione (200 mg, 0.45 mmol), and pyridine (0.11 mL, 1.35 mmol) in CH₂Cl₂ (5 mL) at 0° C. The reaction mixture was stirred at 25° C for 4 hours. CH₂Cl₂ (20 mL) was added, and the mixture was washed with 10 mL portions of 3% HCl, water and brine and dried over anhydrous MgSO₄. Removal of the solvent in vacuo left the crude mesylate (205 mg) which was homogeneous by TLC (1% methanol in CHCl₃. This material was carried on directly to the next step.

To a solution of the above mesylate (205 mg) in 10 mL of THF was added 40% aqueous dimethylamine (2 mL) and the reaction mixture was heated at 50° C. for 36 hours. After removal of the THF under reduced pressure, CH₂Cl₂ (20 mL) was added to the residue. The mixture was washed with 5% aqueous NaHCO₃, water and brine and dried over anhydrous MgSO₄. Concentration afforded crude (R)-3,4-[(N,N'-1,1'-(3"-(N,N-dimethylamine)methylene)-hexane)-bis-(3,3'-indolyl)]-1H-pyrrole-2,5-dione (158 mg) as a red solid that was purified by preparative HPLC (Waters reverse-phase, 0.1 % TFA and 5% CH₃CN in water—100% CH₃CN gradient) to give the amine-TFA salt which was dissolved in CH₂Cl₂ and converted to the free base with dilute aqueous KOH. After drying the organic phase over MgSO₄ (15 minutes), the solvent was evaporated and the free amine (60 mg) was dissolved into 1:1 methanol/THF (5 mL), cooled to 0° C. under N₂ and slowly acidified to pH 4–5 (external damp pH paper) with anhydrous 1N HCl in ether. The precipitated salt was filtered and washed with dry ether under a N₂ blanket then dried in a vacuum desiccation over CaSO₄ overnight. The dimethylamine-HCL salt, (R)-3,4-[(N,N'-1,1'-(3"-(N,N-dimethylamine)methylene)-hexane)-bis-(3,3'-indolyl)]-1H-pyrrole-2,5-dione hydrochloride salt (43 mg) was obtained as a light red solid, M.Pt. 230° C. (dec.). MS.

$^1$H NMR (300 MHz, acetone-d₆) 0.9–3.5 (m, 7H) , 3.20–3.42 (m, 8H), 4.05–4.18 (m, 4H), 7.02–7.80 (m, 10H), 10.94(s, 1H).

EXAMPLE 40s (S)-3,4-[(N,N'-1,1'-(3"-(N,N-dimethylamine)methylene)-hexane)-bis-(3,3'-indolyl)]-1H-pyrrole-2,5-dione hydrochloride salt Following the same procedure described above for the preparation of Example 40r, (S)-3,4-[(N,N'-1,1'-(3"-(N,N-dimethylamine)methylene)-hexane)-bis-(3,3'-indolyl)]-1H-pyrrole-2,5-dione hydrochloride salt was prepared (90 mg) in 27% overall yield from the alcohol, (S)-3,4-[(N,N'-1,1'-(3"-hydroxymethylene)-hexane)-bis-(3,3'-indolyl)]-1H-pyrrole-2,5-dione by formation of the mesylate and displacement with dimethylamine. MS.

$^1$NMR (d6 DMSO) δ 0.92 (s large,1 H), 1.35 (s large, 1 H), 1.60 (s large, 2 H), 1.85 (s large, 1H), 2.37–2.42 (m, 2H), 2.91–3.05 (m, 2H), 4.13 (s large, 2H), 4.23 (s large, 2H), 7.11–7.23 (m, 4H), 7.34 (d, J=20 Hz, 2H), 7.50 (dd, J=8.1 Hz, J=12.6 Hz, 2H), 7.79 (d, J=8 Hz, 2H), 9.92 (s large, 1H), 10.98 (s, 1H)

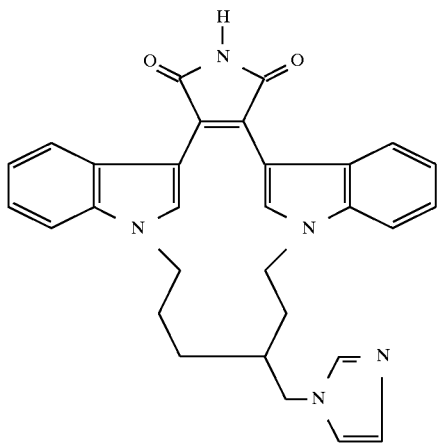

EXAMPLE 41

3,4- [(N,N'-1,1'-(3"-(N-imidazole)methylene)-hexane)-bis-(3,3'-indolyl)]-1H-pyrrole-2,5-dione Methanesulfonyl chloride (0.025 mL, 0.32 mmol) was added dropwise to a stirred solution containing 3,4-[(N,N'-1,1'-(3"-(hydroxy)methylene)-hexane)-bis-(3,3'-indolyl)]-1H-pyrrole-2,5-dione (100 mg, 0.23 mmol) and triethylamine (0.05 mL, 0.36 mmol) in dry CHC$_{13}$ at 25° C. under N$_2$. After stirring for 20 minutes, the reaction mixture was diluted with CHCl$_3$ (15 mL), washed with water, brine, dried filtered and concentrated. The red residue was purified by chromatography on a short column of silica gel eluting with CHCl$_3$ followed by 10% EtOAc in CHCl$_{13}$ to give 3,4-[(N,N'-1,1'-(3"-methanesulfonyloxymethylene)-hexane)-bis-(3,3'-indolyl)]-1H-pyrrole-2,5-dione, 53 mg, as a red solid, which was homogenous by TLC 5% (EtOAc in CH$_2$Cl$_2$).

To a stirred solution of 3,4-[(N,N'-1,1'-(3"-(methanesulfonyloxy)methylene)-hexane)-bis-(3,3'-indolyl)]- 1H-pyrrole-2,5-dione (49 mg, 0.095 mmol) in DMF (0.75 mL) under N$_2$ was added dropwise a solution of the sodium salt of imidazole in DMF (prepared by adding 60% NaH (8.7 mg, 0.22 mmol) to a solution of imidazole (16 mg, 0.24 mmol) in DMF (0.5 mL)). The reaction mixture was stirred 15 minutes at 25° C. then heated at 50° C for 30 minutes. The reaction mixture was diluted with 25 mL of CH$_2$Cl$_2$ containing 3% methanol. The mixture was washed with 10 mL portions of water and brine and dried over anhydrous Na$_2$SO$_4$. After evaporation of the solvents under reduced pressure, the crude product was loaded onto a 3"×3" column of silica gel eluting with CH$_2$Cl$_2$ followed by 5% methanol in CH$_2$Cl$_2$ containing 1% triethylamine to afford 3,4-[(N,N'-1,1'-(3"-(N-imidazole)methylene)-hexane)-bis-(3,3'-indolyl)]-1H-pyrrole-2,5-dione, 21.5 mg (46%) as a red solid. This material was subjected to reverse-phase HPLC (gradient elution, 5% CH$_3$CN in water containing 0.1% TFA—CH$_3$CN) to provide analytically pure 3,4-[(N,N'-1,1'-(3"-(N-imidazole)methylene)-hexane)-bis- (3,3'-indolyl)]-1H-pyrrole-2,5-dione (12.4 mg) as a red solid, M.Pt. 261°–266° C. NMR. HRMS calculated for C$_{30}$H$_{27}$N$_5$O$_2$ [M+1]: 490.2244. Found 490.2242.

The following compounds were prepared in a manner analogous to the Examples described herein and further illustrate the compounds of the invention. In the following examples, the structure of the compound was confirmed by NMR, MS, and/or elemental analysis.

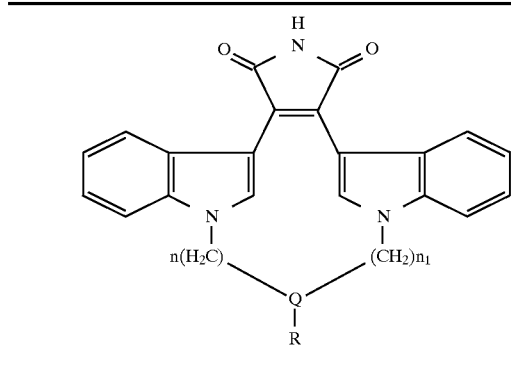

| Example | n | n1 | O | R |
|---------|---|----|---|---|
| 42 | 3 | 3 | CH | H |
| 43 | 2 | 2 | CH | H |
| 44 | 3 | 4 | CH | H |
| 45 | 3 | 3 | CH | NH$_2$ |
| 46 | 3 | 3 | CH | NHCOCH$_3$ |
| 47 | 3 | 3 | CH | NHCH$_2$C$_6$H$_5$ |
| 48 | 3 | 3 | C | (—OCH$_2$CH$_2$O—) |
| 49 | 3 | 3 | C | =O |

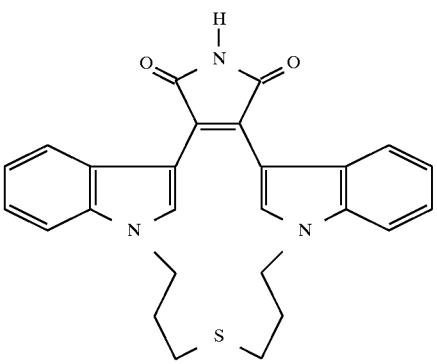

EXAMPLE 50

3,4-[(N,N'-1,1'-(propylthiopropyl))-bis-(3,3'-indolyl)]-1H-pyrrole-2,5-dione

To a 0° C. stirred anhydrous CH$_2$Cl$_2$ (1.0 L) solution of N-(3-acetoxypropyl)-indole (102 g, 0.47 moles) was added oxalyl chloride (43.04 mL, 0.494 moles, 1.05 eq.) dropwise.

After 15 minutes, the ice bath was removed. The reaction mixture was allowed to warm to ambient temperature with stirring for three hours. The volatiles were removed in vacuo to yield a magenta solid, which was redissolved in dry $CH_2Cl_2$ (1.0 1) under $N_2$. With vigorous stirring, N-tertbutoxycarbonyl-indole-3-acetic acid (129.25 g, 0.47 moles), was added followed rapidly by triethylamine (130.6 mL, 0.94 moles, 2 eq.). After 16 hours, the reaction was concentrated and purified by flash column chromatography eluting with 3:1 hexane/ethyl acetate. The major colored fraction was concentrated to give the anhydride (101 g, 40% yield) 2-[1-(3-acetoxypropyl)-3-indolyl]-3-[1-tert-butoxycarbonyl-3-indolyl]-furan-1,4-dione as a red crystalline solid. MS To the BOC protected anhydride (7.4 g, 14 mmol) was added trifluoroacetic acid (27 mL, 350 mmol) containing ethanethiol (1 mL, 14 mmol) with stirring. After one hour, the reaction mixture was partitioned between $CH_2Cl_2$ and saturated $NaHCO_3$. The organic layer was washed with brine, dried over $Na_2SO_4$, and filtered. The filtrate was concentrated to give the crude deblocked anhydride as a red semi-solid. The residue was applied to a short pad of silica, washed with hexane and then $CH_2Cl_2$. The colored band was eluted from the silica with ethyl acetate and dried in vacuo to give the purified deblocked anhydride, 2-[1-(acetoxypropyl)-3-indolyl]-3-(3-indolyl)-furan-1,4-dione (5.7 g, 95% yield) as red solid. MS To a stirred anhydrous DMF (125 mL) solution of the deblocked anhydride (3.0 g, 7 mmol) was added NaH (420 mg, 10.5 mmol, 60% in mineral oil) at room temperature. A color change from bright orange to violet was immediately observed. After 30 minutes, 3 equivalents of 3-bromopropyl acetate was added rapidly. The reaction was heated to 75° C., and gradually returned to an orange color. After 6 hours, the DMF was removed in vacuo. The residue was applied to a flash silica chromatography column eluting with 3:2 hexane/ethyl acetate. The major red band was collected, and the solvent removed to give the alkylated anhydride, 2,3-bis[1-(3-acetoxypropyl)-3-indolyl]-furan-1,4-dione (1.32 g, 36%) as a red solid. MS 2, 3-bis[1-(3-acetoxypropyl)-3-indolyl]-furan-1,4-dione (1.32 g, 2.52 mmol) was suspended in absolute ethanol (125 mL) with stirring and treated with 5N KOH (125 mL). After stirring for 16 hours, the reaction mixture was concentrated to 126 mL. The residue was acidified (5N HCl) slowly, until a red solid precipitated. The precipitant was filtered and dried in a vacuum oven at 60° C., producing the alcohol anhydride 1.1 g (99%) as a red powder.

The alcohol anhydride, (1.1 g, 2.47 mmol) was dissolved in anhydrous DMF (30 mL) under a $N_2$ atmosphere with stirring. A premixed solution of 1,1,1,3,3,3-hexamethyl-disilazane (5.22 mL, 24.7 mmol, 10 eq.) and methanol (0.50 mL, 12.4 mmol, 5 eq.) was added. The reaction was allowed to stir for 16 hours at ambient temperature. The DMF was removed in vacuo. To this residue was added acetone (100 mL) and excess CsF (ca. 500 mg). After stirring 4 hours, the reaction was concentrated. The residue was partitioned between ethyl acetate and water. The organic layer was washed with 1N HCl (5x), brine (2x), dried over $Na_2SO_4$ and filtered. The filtrate was concentrated to give the bisindolylmaleimide 3,4-bis[1-(3-hydroxypropyl)-3-indolyl]-1H-pyrrole-2,5-dione 1.0 g (91% yield) as a red powder. Total yield was 90% over two steps. MS 3,4-bis[1-(3-hydroxypropyl)-3-indolyl]-1H-pyrrole-2,5-dione (1.0 g, 2.25 mmol) was dissolved in anhydrous $CH_2Cl_2$ (250 mL) at ambient temperature under $N_2$. $CBr_4$ (2.09 g, 6.3 mmol, 2.8 eq) and triphenylphosphine (2.83 g, 10.8 mmol, 4.8 eq.) were added together to the reaction vessel. The mixture was allowed to stir for 16 hours. The crude reaction mixture was concentrated and purified by silica gel flash column chromatography, eluting with 7:3 hexane/ethyl acetate. The desired product eluted as one major red band. Removal of the solvents from this fraction gave the dibromo compound, 3,4-bis[1-(3-bromopropyl)-3-indolyl]-1H-pyrrole-2,5-dione 876 mg (68% yield) as a red powder.

The dibromo compound (47.8 mg, 0.084mmol) was dissolved in acetone at ambient temperature with stirring. An excess of sodium sulfide nonahydrate (229 mg, 0.95 mmol, 11.3 eq.) was added. The heterogeneous mixture was stirred overnight. The acetone was then removed in vacuo. The residue was partitioned between water and $CH_2Cl_2$. The organic layer was washed with brine, dried over sodium sulfate and concentrated to give 35.5 mg (94% yield) of the titled product as an red-orange solid. MS

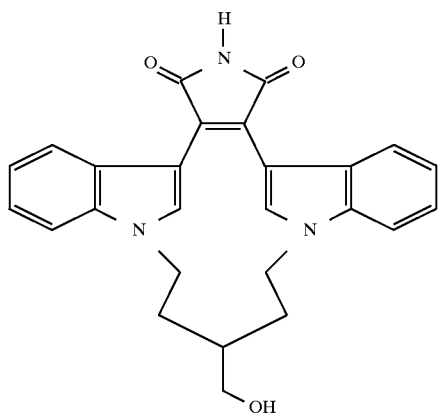

EXAMPLE 51

3,4-[(N,N'-1,1'-(3"-(hydroxy)methylene)pentan)-bis-(3,3'-indolyl)]-1(H)-pyrrole-2,5-dione A dry DMF (35 mL) solution of 1,5-diiodo-3-(tert-butyldiphenylsilyloxymethylene)-pentane (7.3g, 12 mmol) and bis-(3,3'-indolyl)]-1(H)-pyrrole-2,5-dione (4.21g, 12 mmol) was added via syringe pump over 48 hours to a suspension of $Cs_2CO_3$ (16.06 g, 49.3 mmol) in dry DMF (1 L) with vigorous stirring at 55° C. under $N_2$. After an additional 2 hours, the reaction mixture was concentrated in vacuo, the residue dissolved in $CH_2Cl_2$, washed with 1N HCl, brine, dried, and concentrated in vacuo to give a violet oil. The oil is passed through a plug of silica eluting with 4:1 hexanes/ethyl acetate. The eluant was reduced to yield the macrocycle, 3,4-[(N,N'-1,1'-(3"-(tertbutyldiphenylsilyloxymethylene)pentanyl)-bis-(3,3'-indolyl)]-1(methyl)-pyrrole-2,5-dione, 4.5 g (55% yield) as a magenta solid.

To an ethanol (300 mL) suspension of 3,4-[(N,N'-1,1'-(3"-(tertbutyldiphenylsilyloxymethylene)pentanyl)-bis-(3,3'-indolyl)]-1(methyl)-pyrrole-2,5-dione (4.2 g, 6.2 mmol)

was added 5N KOH (300 mL). The reaction was refluxed (86° C.) for 48 hours with stirring, cooled to room temperature, and the ethanol removed in vacuo. The concentrate was acidified to pH 1 with 5N HCl (325 mL), extracted with ethyl acetate, washed with brine (2×), dried, and concentrated to give the anhydride, 3,4-[(N,N'-1,1'-(3"-(hydroxymethylene)pentan)-bis-(3,3'-indolyl)]-furan-2,5-dione, 2.6 g (100% yield) as a residue.

To a dry DMF (500 mL) solution of the anhydride, 3,4-[(N,N'-1,1'-(3"-(hydroxymethylene)pentanyl)-bis-(3,3'-indolyl)]-furan-2,5-dione (2.6 g, 6.2 mmol), was added a solution of methanol (1.25 mL, 31 mmol) and 1,1,1,3,3,3-hexamethyldisilazane (13.1 mL, 62 mmol). After heating (55° C.) 36 hours the reaction was concentrated in vacuo, diluted with ethyl acetate, washed with 1N HCl. The acid wash contained some solids that were back extracted with chloroform. The combined organic layer was dried, and concentrated to a violet residue. The residue was applied to a short plug of silica and eluted with 2–10% MeCN/CH$_2$Cl$_2$. The fraction containing the major product is concentrated in vacuo to yield the title alcohol 3,4-[(N,N'-1,1'-(3"-(hydroxymethylene)pentanyl)-bis-(3,3'-indolyl)]-1(H)-pyrrole-2,5-dione (650 mg (25%)) as a magenta solid. MS.

$^1$H NMR: (DMSO-d$_6$) δ 0.7 (m, 1H); 1.48 (m, 2H); 1.82 (m, 2H); 3.19 (dd, 2H); 4.16 (m, 4H); 4.4 (t, 1H); 7.05 (t, 2H); 7.16 (t, 2H); 7.17 (s, 2H); 7.46 (d, 2H); 7.65 (d, 2H); 10.96 (s, 1H).

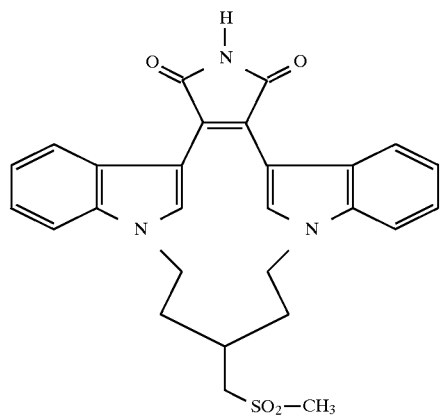

EXAMPLE 52

3,4-[(N,N'-1,1'-(3"-(methanesulfonyloxy)methylene)pentan-1",5"-yl)-bis-(3,3'-indolyl)]-1(H)-pyrrole-2,5-dione To a dry CH$_2$C$_{12}$ (80 mL) solution of 3,4-[(N,N'-1,1'-(3"-(hydroxymethylene)pentan-1",5"-yl)-bis-(3,3'-indolyl)]-1 (H)-pyrrole-2,5-dione (334120) (650 mg, 1.5 mmol) was added methanesulfonic anhydride (400 mg, 2.29 mmol) followed by excess pyridine (370 mL, 4.58 mmol). After 16 hours at ambient temperature, the reaction mixture was applied directly to a short plug of silica and eluted with 0–7% MeCN/CH$_2$Cl$_2$. The colored fraction was concentrated in vacuo to give the mesylate, 3,4-[(N,N'-1,1'-(3"-(methanesulfonyloxy)methylene)pentan-1",5"-yl)-bis-(3,3'-indolyl)]-1(H)-pyrrole-2,5-dione 501 mg (67% yield) of a violet solid. MS.

$^1$H NMR: (DMSO-d$_6$) δ 0.89 (m, 1H); 1.61 (m, 2H); 1.82 (m, 2H); 2.99 (s, 3H); 4.02 (d, 2H); 4.22 (m, 4H); 7.06 (t, 2H); 7.17 (t, 2H); 7.17 (s, 2H); 7.54 (d, 2H); 7.63 (d, 2H); 10.98 (s, 1H).

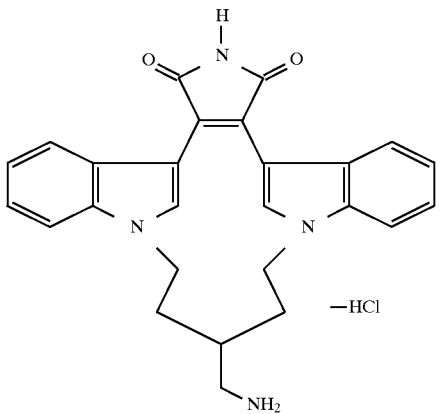

EXAMPLE 53

3,4-[(N,N'-1,1'-(3"-(aminomethylene)pentan-1",5"-yl)-bis-(3,3'-indolyl ]-1(H)-pyrrole-2,5-dione hydrochloride salt In a sealed tube reaction vessel containing a THF (20 mL) solution of the mesylate 3,4-[(N,N'-1,1'-(3"-(methanesulfonyloxy)methylene)pentan-1",5"-yl)-bis-(3,3'-indolyl)]-1(H)-pyrrole-2,5-dione (250 mg, 0.5 mmol) was added NH$_4$OH (33% aq, 10 mL), the reaction tube was sealed, and heated (60° C.). After 48 hours, the reaction mixture was cooled and eluted through a plug of silica gel with ethyl acetate followed by acetone. The acetone fraction was reduced in vacuo to give a reddish solid. A portion of this residue is purified using reverse phase gel filtration HPLC (85% MeCN/water, 0.01% TFA). The pure fractions are pooled and concentrated to a red solid. The solid is then partitioned between ethyl acetate/0.1N NaOH. The organic layer was concentrated to give the free base as a residue. The residue was dissolved in methanol (2 mL) and treated with HCl (2 mL, 1.0M in ether) for 1 hour. The reaction was concentrated in vacuo to yield the title compound 28.5 mg (13%) of a magenta solid which is >95% pure by HPLC analysis. MS.

$^1$H NMR: (DMSO-d$_6$) δ 1.17 (m, 1H); 1.5–1.63 (m, 2H); 1.8–1.95 (m, 2H); 2.73 (m, 2H); 4.18 (m, 4H); 7.12 (t, 2H); 7.15 (s, 2H); 7.23 (t, 2H); 7.56 (d, 2H); 7.75 (d, 2H); 7.8 (br, 3H); 11.01 (s, 1H).

EXAMPLE 54

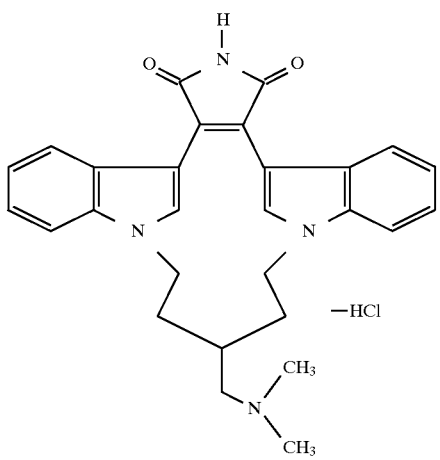

3,4-[(N,N'-1,1'-(3"-(N,N-(dimethylamino)methylene)pentanyl)-bis-(3,3-indolyl)]-1(H)-pyrrole-2,5-dione hydrochloride The title compound was prepared as the hydrochloride salt by using dimethylamine (40% aq, 5 mL) to displace the mesylate 3,4-[(N,N'-1,1'-(3"-(methanesulfonyloxy)methylene)pentanyl)-bis-(3,3'-indolyl)]-1(H)-pyrrole-2,5-dione (110 mg, 0.2 mmol) and subsequently transforming to the hydrochloride salt to produce the titled compound (28 mg, 26% yield). MS.

$^1$H NMR: (DMSO-$d_6$) δ 1.17 (m, 1H); 1.5–1.63 (m, 2H); 1.8–1.95 (m, 2H); 2.73 (m, 2H); 4.18 (m, 4H); 7.12 (t, 2H); 7.15 (s, 2H); 7.23 (t, 2H); 7.56 (d, 2H); 7.75 (d, 2H); 7.8 (br, 3H); 11.01 (s, 1H).

The following compounds are prepared in an analogous manner and further illustrate the compounds of the invention:

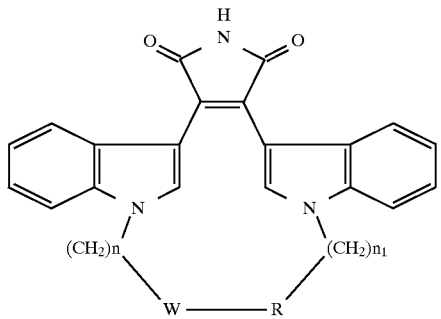

| Example | n | n1 | W | R |
|---|---|---|---|---|
| 55 | 3 | 2 | O | =CHCH$_2$NHCH$_2$C$_6$H$_5$ |
| 56 | 3 | 2 | O | =CHCH$_2$OCONH(C$_6$H$_5$) |
| 57 | 3 | 2 | O | =CHCH$_2$NHCOCH$_3$ |
| 58 | 3 | 2 | O | =CHCH$_2$NHSO$_2$C$_6$H$_5$ |
| 59 | 3 | 2 | O | =CHCH$_2$CH$_2$OH |
| 60 | 3 | 2 | O | =CHCH$_2$CH$_2$NH$_2$ |
| 61 | 2 | 2 | O | =CHCH$_2$OCONH(C$_6$H$_5$) |
| 62 | 2 | 2 | O | =CHCH$_2$CH$_2$OH |
| 63 | 2 | 2 | O | =CHCH$_2$CH$_2$NH$_2$ |
| 64 | 2 | 2 | CH | =CHCH$_2$NHCH$_3$ |
| 65 | 2 | 2 | CH | =CHCH$_2$NHSO$_2$C$_6$H$_5$ |
| 66 | 2 | 2 | CH | =CHCH$_2$CH$_2$OH |
| 67 | 2 | 2 | CH | =CHCH$_2$CH$_2$NHCH$_2$C$_6$H$_5$ |
| 68 | 2 | 2 | CH | =CHCH$_2$CH$_2$NH$_2$ |
| 69 | 2 | 2 | CH | =CHCH$_2$CH$_2$OCONH(C$_6$H$_5$) |
| 70 | 2 | 2 | CH | =CHCH$_2$CH$_2$NHSO$_2$CH$_3$ |
| 71 | 2 | 2 | CH | =CHCH$_2$CH$_2$N(CH$_3$)$_2$ |
| 72 | 2 | 2 | CH | =CHCH$_2$CH$_2$NHCH$_3$ |
| 73 | 2 | 2 | CH | =CHCH$_2$OCH$_2$CH$_2$NH$_2$ |
| 74 | 2 | 2 | —OCH$_2$— | =CHCH$_2$NH$_2$ |
| 75 | 2 | 2 | —OCH$_2$— | =CHCH$_2$NHCH$_3$ |
| 76 | 2 | 2 | —OCH$_2$— | =CHCH$_2$NHCH$_2$C$_6$H$_5$ |
| 77 | 2 | 2 | —OCH$_2$— | =CHCH$_2$OCONH(C$_6$H$_5$) |
| 78 | 2 | 2 | —OCH$_2$— | =CHCH$_2$NHCOCH$_3$ |
| 79 | 2 | 2 | —OCH$_2$— | =CHCH$_2$NHSO$_2$C$_6$H$_5$ |
| 80 | 2 | 2 | —OCH$_2$— | =CHCH$_2$CH$_2$OH |
| 81 | 2 | 2 | —OCH$_2$— | =CHCH$_2$CH$_2$NH$_2$ |

-continued
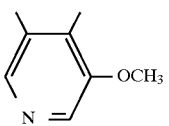
| Example | n | n1 | W | R |
|---------|---|----|----|----|
| 82 | 2 | 3 | 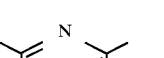 | —CH— |
| 83 | 2 | 3 | 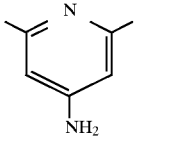 | —CH— |
| 84 | 2 | 3 | 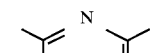 | —CH— |
| 85 | 2 | 3 | 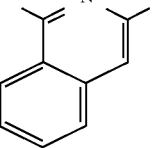 | —CH— |
| 86 | 2 | 3 | 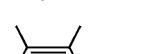 | —CH— |
| 87 | 2 | 3 | 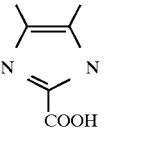 | —CH— |

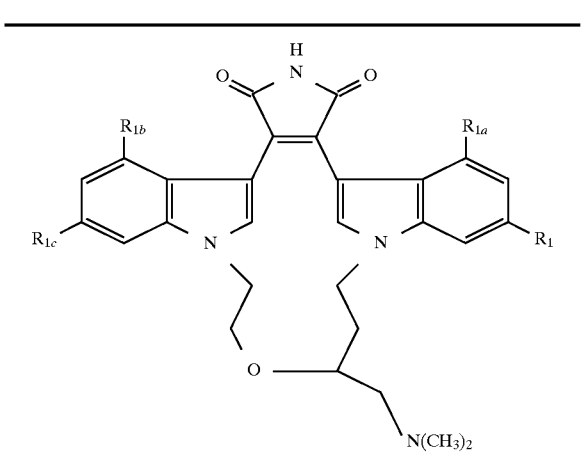

| Ex. | R₁ | R₁ₐ | R₁ᵦ | R₁c |
|---|---|---|---|---|
| 88 | H | CH₃ | H | H |
| 89 | OCH₃ | H | H | H |
| 90 | H | CH₃ | Cl | H |
| 91 | H | NO₂ | H | H |
| 92 | CF₃ | H | H | H |
| 93 | OH | H | CH₃ | H |
| 94 | N(CH₃)₂ | H | H | H |

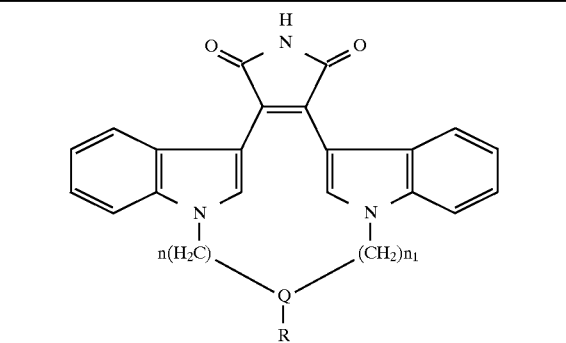

| Example | n | n1 | Q | R |
|---|---|---|---|---|
| 95 | 3 | 3 | S | =O |
| 96 | 3 | 3 | S | (=O)₂ |
| 97 | 3 | 3 | O | — |
| 98 | 3 | 3 | CH | —OH |
| 99 | 3 | 3 | CH | OCONHC₆H₅ |
| 100 | 3 | 3 | N | H |
| 101 | 3 | 3 | N | CH₃ |
| 102 | 3 | 3 | CH | NHSO₂C₆H₅ |
| 103 | 3 | 3 | CH | NHCH₃ |
| 104 | 3 | 3 | CH | NHCH₂C₆H₅ |
| 105 | 3 | 3 | CH | N(CH₃)₂ |
| 106 | 3 | 3 | CH | —N⟨pyrrolidine⟩ |
| 107 | 3 | 3 | CH | CH₂CN |
| 108 | 3 | 3 | CH | CH₂NH₂ |
| 109 | 3 | 3 | CH | CH₂NHCOCH₃ |
| 110 | 3 | 3 | CH | CH₂N(CH₃)₂ |
| 111 | 3 | 3 | CH | CH₂NHSO₂C₆H₅ |
| 112 | 3 | 3 | CH | CH₂NHCH₂C₆H₅ |
| 113 | 2 | 2 | C | =O |

EXAMPLE 114

3,4-[(N,N'-1,1'-((2"-ethoxy)-(3'"(O)-4'"-(N-trifluoromethylamino)-butane)-bis(3,3'-indolyl)]-1(H)-pyrrole-2,5-dione 3,4-[(N,N'-1,1'-((2"-ethoxy)-3'"(O)-4'"-(N-methylamine)-butane-bis(3,3'-indolyl)]-1-(methyl)-pyrrole-2,5-dione (20 mg, 0.04 mmol) was dissolved in THF (10 mL) containing triethylamine (6.1 μL, 0.044 mmol) under nitrogen. To this solution was added carbon disulfide (3 microL, 0.05 mmol), and after 15 minutes methyl iodide was added. The reaction was complete after 12 hours by TLC (10% MeOH in CH₂Cl₂). The reaction mixture was diluted with ethyl acetate, washed with water, brine, dried and concentrated to give a dithiocarbamate (23 mg, expected mass) IS/MS 559 (M⁺+1) expected mass 558.

To a dichloromethane solution of the dithiocarbamate is added tetrabutylammonium dihydrogen-trifluoride and N-bromosuccinimide. Work up and purification by chromatography generates the 3,4-[(N,N'-1,1'-((2"-ethoxy)-3'"(O)-4'"-(N,N+(trifluoromethy)methylamino)-butane-bis(3,3'indolyl)]-1-(methyl)-pyrrole-2,5,-dione, which is converted to the N—H maleimide.

The trifluoromethylamine derivative may also be prepared as follows:

To a DMSO solution of the monomethyl amine is added dibromodifluoromethane and tetrakis(dimethylamine)-ethylene. Standard work up gives the desired trifluoromethylamine derivative. The trifluoromethyl derivative would be converted to the N—H maleimide as previously described.

As previously noted, the compounds of the present invention are potent, protein kinase C inhibitors. The compounds are selective for protein kinase C over other kinases.

The ability of the compounds of the present invention to selectively inhibit protein kinase C was determined in the Calcium Calmodulin Dependent Protein Kinase Assay, Casein Protein Kinase II assay, cAMP-Dependent Protein Kinase Catalytic Subunit assay and the Protein-Tyrosine Kinase assay.

Calcium Calmodulin Dependent Protein Kinase
Assay (CaM)

The Calcium Calmodulin Dependent Protein Kinase Assay is described in the *Journal of Neuroscience*, 3:818–831 (1983). The assay components are in a total volume of 250 μL: 55 mM HEPES (4-(2-hydroxyethyl)-1- piperazine-ethanesulfonic acid), pH 7.5, 2.75 mM dithiothreitol, 2.2 mM EGTA (ethylenebis (oxyethylenenitrilo)tetraacetic acid, used in the blank buffer), 1.1 mM calcium chloride (Sigma, St. Louis, Mo.) (used in the control buffer), 10 mM magnesium chloride (Sigma, St. Louis, Mo.), 200 µg/mL histone type HL (Worthington), 10 µL DMSO or DMSO/inhibitor and 30 µM (gamma 32P) ATP (DuPont). The reaction is initiated by the addition of calcium calmodulin dependent protein kinase (isolated from rat brain homogenate), incubated at room temperature for 10 minutes and stopped by adding 0.5 mL ice cold trichloroacetic acid (Amresco) followed by 100 µL of 1 mg/mL bovine serum albumin (Sigma, St. Louis, Mo.). The precipitate is collected by vacuum filtration on glass fiber filters and quantified by counting in a beta scintillation counter.

Buffer components:

|  | Control buffer | Blank buffer |
| --- | --- | --- |
| 200 mM HEPES pH 7.5 | 3125 µL | 625 µL |
| 50 mM DTT | 625 µL | 125 µL |
| histone | 1250 µL | 250 µL |
| 100 mM calcium | 125 µL | — |
| 100 mM EGTA | — | 50 µL |
| DI water | 2375 µL | 450 µL |

Assay components:

165 µL Buffer

25 µL calmodulin (250 µg/mL)

10 µL DMSO or DMSO/inhibitor

25 µL kinase enzyme

25 µL AT32P.

Casein Protein Kinase II Assay (CK-II)

The Casein Protein Kinase II Assay is described in Neurochem. Res., 13: 829–836 (1988). The assay components are in a total volume of 250 µL: 20 mM Tris-HCl, pH 7.5, 5 mM sodium fluoride, 50 mg/mL Casein (Sigma, St. Louis, Mo.), 10 mM magnesium chloride (Sigma, St. Louis, Mo.), 10 µL DMSO or DMSO/inhibitor and 30 µm (gamma-32P) ATP (DuPont). Initiation of the reaction is performed by addition of casein protein kinase II (isolated from rat brain homogenate), incubated at room temperature for 10 minutes and stopped by the addition of 0.5 mL ice cold Trichloroacetic acid (Amresco) followed by 100 µL of 1 mg/mL bovine serum albumin (Sigma, St. Louis, Mo.). The precipitate is collected by vacuum filtration on glass fiber filters and quantified by counting in a beta scintillation counter.

Assay components in order of addition

175 µL Buffer

10 µL or DMSO or DMSO/inhibitor

25 µL of AT32P in 300 µM magnesium chloride

40 µL of enzyme (undiluted)

Buffer prepared as follows: (Final volume=3.5 mL: amount of 20 assays)

| 500 µL of each: | 200 mM Tris-HCl pH 7.5 |
| --- | --- |
|  | 50 mM sodium fluoride |
|  | 50 mg/mL Casein |
|  | + 2 mL DI water |
| Total Volume | 3.5 mL | cAMP-DeDendent Protein Kinase Catalytic Subunit Assay (PKA)

The Assay components are in a total volume of 250 µL: 20 mM HEPES (Sigma, St. Louis, Mo.) buffer pH 7.5, 200 µg/mL histone type HL (Worthington), 10 mM magnesium chloride (Sigma, St. Louis, Mo.), 10 µL DMSO or DMSO inhibitor and 30 µM (gamma- 32P) ATP (DuPont). The reaction is initiated by addition of bovine heart cAMP-dependent kinase catalytic subunit (Sigma, St. Louis, Mo.), incubated to 30° C. for 10 minutes and stopped by adding 0.5 mL ice cold Trichloroacetic acid (Amresco) followed by 100 µL of 1 mg/mL bovine serum albumin (Sigma). The precipitate is collected by vacuum filtrated on glass fiber filters employing a TOMTEC™ and quantified by counting in a beta scintillation counter. This assay is done identical to the protein kinase C (PKC) enzyme assay except that no phospholipids or diacylglycerol are employed in the assay and the histone substrate is specific for the cAMP-dependent catalytic subunit enzyme.

Protein Tyrosine Kinase Assay (src)

The Assay components are the following:

10 µL Raytide

10 µL Kinase

4 µL DMSO or DMSO/inhibitor

6 µL 200 mM HEPES pH 7.5

10 µL AT32P

This assay is described by Onogene Science, Inc. Cat. #PK02 and PK03 (1990).

Surprisingly, the compounds of the present invention are also isozyme-selective inhibitors, that is, the compounds selectively inhibit protein kinase C beta-1 and beta-2 isozymes. This isozyme selectivity was determined in the PKC Enzyme Assay.

PKC Enzyme Assay

PKC enzymes=alpha, beta I, beta II, gamma, delta, epsilon, eta and zeta.

Assay components in a total volume of 250 µL are as follows:

Vesicles consisting of 120 µg/mL phosphatidylserine (Avanti Polar Lipids) and sufficient diacylglycerol (Avanti Polar Lipids) to activate the enzyme to maximum activity in 20 mM HEPES buffer (Sigma, St. Louis, Mo.), pH 7.5, 940 µM calcium chloride (Sigma, St. Louis, Mo.) for assaying the alpha, beta-1, beta-2 and gamma enzyme only, 1 mM EGTA for all the enzymes, 10 mM magnesium chloride (Sigma, St. Louis, Mo.) and 30 µM (gamma-32P) ATP (DuPont). For all the enzymes either histone type HL (Worthington) or myelin basic protein is used as substrate. The assay is started by addition of protein kinase C enzyme incubated at 30° C. for 10 minutes and stopped by adding 0.5 mL of cold trichloroacetic acid (Amresco) followed by 100 µL of 1 mg/mL bovine serum albumin(Sigma, St. Louis, Mo.). The precipitate is collected by vacuum filtration on glass fiber filters employing a TOMTEC™ filtration system and quantified by counting in a beta scintillation counter.

Table 1 demonstrates the PKC selectivity of representative compounds in the above assays.

TABLE 1

| | | | IC$_{50}$ ($\mu$M) | | | | |
|---|---|---|---|---|---|---|---|
| Ex. | PKC-α | PKC-β1 | PKC-β2 | PKA | CaM | CK-II | src |
| 1 | 1 | 0.05 | 0.04 | NA | NA | >100 | NA |
| 2 | 4 | 0.4 | 0.2 | >100 | >100 | >100 | >100 |
| 3 | 0.3 | 0.03 | 0.02 | >100 | 3 | >100 | >100 |
| 4 | 0.3 | 0.02 | 0.008 | NA | 3 | >100 | 37 |
| 4s | 1.3 | 0.048 | 0.033 | >100 | 2.5 | >100 | 63 |
| 4r | 0.30 | 0.005 | 0.021 | >100 | 0.69 | >100 | 33 |
| 5 | 0.28 | 0.012 | 0.005 | >100 | 4.0 | >100 | 21 |
| 5s | 0.36 | 0.0047 | 0.0059 | >100 | 8 | >100 | >100 |
| 5r | 0.4 | 0.01 | 0.01 | >100 | 5 | >100 | 63 |
| 6 | 4.2 | 0.043 | 0.035 | NA | NA | NA | NA |
| 7 | >5.0 | 0.15 | 0.18 | NA | NA | NA | NA |
| 8 | 2.5 | 0.037 | 0.032 | NA | NA | NA | NA |
| 9 | 3.0 | 0.35 | 0.16 | >100 | 26 | >100 | 58 |
| 11 | 5 | 0.3 | 0.1 | >100 | 20 | >100 | >100 |
| 12 | 19 | 0.6 | 0.5 | >100 | 93 | >100 | NA |
| 13 | >5.0 | 1.9 | 0.94 | NA | NA | NA | NA |
| 15 | >5.0 | 2.9 | 0.83 | NA | NA | NA | NA |
| 16 | >5.0 | 3.2 | 2.3 | NA | NA | NA | NA |
| 17s | 0.24 | <0.005 | <0.005 | 0.16 | 2.2 | >100 | NA |
| 18s | 6.4 | 0.38 | 0.30 | >100 | 4.4 | >100 | >100 |
| 18r | 3.4 | 0.083 | 0.087 | >100 | 8.8 | >100 | NA |
| 19r | 0.48 | 0.032 | 0.030 | >100 | 2.2 | >100 | >100 |
| 20r | 0.89 | 0.04 | 0.03 | >100 | 7.3 | >100 | 74 |
| 20s | 3 | 0.1 | 0.05 | >100 | 6.7 | >100 | 16 |
| 21r | 68 | 0.18 | 0.05 | >100 | 56 | >100 | >100 |
| 21s | >5.0 | 0.17 | 0.044 | NA | NA | NA | NA |
| 23s | 1.8 | 0.30 | 0.24 | NA | NA | NA | NA |
| 24s | 3.5 | 0.49 | 0.38 | NA | NA | NA | NA |
| 25r | 94 | 0.043 | 0.12 | >100 | 22 | >100 | NA |
| 27 | 2.2 | 0.049 | 0.026 | NA | NA | NA | NA |
| 28 | 1 | 0.07 | 0.08 | NA | 2 | >100 | >100 |
| 29 | >100 | 0.7 | 0.8 | NA | NA | NA | NA |
| 30 | >100 | 1 | 2 | >100 | >10 | >10 | >100 |
| 31 | 0.3 | 0.02 | 0.03 | >100 | 0.47 | >100 | >100 |
| 31r | 0.24 | 0.019 | 0.008 | NA | NA | NA | NA |
| 32 | 0.1 | 0.01 | 0.008 | >100 | 0.9 | >100 | 72 |
| 33 | 0.4 | 0.05 | 0.04 | NA | 0.6 | >100 | 61 |
| 34 | 1 | 0.1 | 0.1 | NA | 4 | >100 | >100 |
| 35 | 9 | 3 | 2 | NA | 82 | >100 | >100 |
| 36r | 0.45 | 0.005 | 0.014 | >100 | 7.1 | >100 | 61 |
| 37 | 0.7 | 0.05 | 0.04 | >100 | 5 | >100 | >100 |
| 38 | 4 | 0.2 | 0.1 | >100 | 9 | >100 | >100 |
| 39 | 31 | 0.4 | 0.3 | >100 | >100 | >100 | >100 |
| 40 | 0.6 | 0.05 | 0.03 | >100 | 5 | >100 | 4.4 |
| 40s | 0.4 | 0.03 | 0.02 | >100 | 41 | >100 | NA |
| 40r | 0.30 | 0.01 | 0.01 | >100 | 8.0 | >100 | 71 |
| 41 | 0.3 | 0.03 | 0.03 | NA | 3 | >100 | 91 |
| 42 | >100 | 0.5 | 0.6 | >100 | >100 | >100 | >100 |
| 43 | 0.4 | 0.04 | 0.03 | NA | 0.6 | >100 | >100 |
| 44 | >100 | 2 | 2 | NA | NA | NA | NA |
| 45 | 3 | 0.1 | 0.1 | >100 | 39 | >100 | >125 |
| 46 | 3 | 0.04 | 0.04 | >100 | 63 | >100 | >100 |
| 47 | 2 | 0.07 | 0.06 | >100 | 70 | >100 | >125 |
| 48 | >100 | 0.5 | 0.3 | >100 | >100 | >100 | >100 |
| 49 | 10 | 0.6 | 0.4 | >100 | >100 | >100 | >100 |
| 51 | 49 | 0.5 | 0.5 | NA | NA | NA | NA |
| 54 | 0.16 | 0.005 | 0.004 | NA | NA | NA | NA |
| 55 | >5.0 | 0.41 | 0.38 | NA | NA | NA | NA |

NA — data are not available

The compounds of the invention inhibit protein kinase C with an IC$_{50}$ value of below 100 $\mu$m. In addition, the compounds of the invention selectively inhibit the beta-1 and beta-2 protein kinase C isozymes and have an IC$_{50}$ value with respect to these isozymes of below 10 $\mu$m.

As an inhibitor of protein kinase C, the compounds are useful in the treatment of conditions in which protein kinase C has demonstrated a role in the pathology. Conditions recognized in the art include: diabetes mellitus and its complications, ischemia, inflammation, central nervous system disorders, cardiovascular disease, Alzheimer's disease, dermatological disease and cancer.

Protein kinase C inhibitors have been shown to block inflammatory responses such as neutrophil oxidative burst, CD3 down-regulation in T-lymphocytes, and phorbol-induced paw edema. Twoemy, B. et al. *Biochem. Biophys. Res. Commun.* 171: 1087–1092 (1990); Mulqueen, M. J. et al. *Agents Actions* 37: 85–89 (1992). Accordingly, as inhibitors of PKC, the present compounds are useful in treating inflammation.

Protein kinase C activity plays a central role in the functioning of the central nervous system. Huang, K. P. *Trends Neurosci.* 12: 425–432 (1989). In addition, protein kinase C inhibitors have been shown to prevent the damage seen in focal and central ischemic brain injury and brain edema. Hara, H. et al. *J. Cereb. Blood Flow Metab.* 10: 646–653 (1990); Shibata, S. et al. *Brain Res.* 594: 290–294 (1992). Recently, protein kinase C has been determined to be implicated in Alzheimer's disease. Shimohama, S. et al., *Neurology* 43: 1407–1413 (1993). Accordingly, the compounds of the present invention are useful in treating Alzheimer's disease and ischemic brain injury.

Protein kinase C activity has long been associated with cell growth, tumor promotion and cancer. Rotenberg, S. A. and Weinstein, I. B. *Biochem. Mol. Aspects Sel. Cancer* 1: 25–73 (1991). Ahmad et al., *Molecular Pharmacology:* 43 858–862 (1993). It is known that inhibitors of protein kinase C inhibitors are effective in preventing tumor growth in animals. Meyer, T. et al. *Int. J. Cancer* 43: 851–856 (1989); Akinagaka, S. et al. *Cancer Res.* 51: 4888–4892 (1991). The compounds of the present invention also act as multidrug reversal (MDR) agents making them effective compounds when administered in conjunction with other chemotherapeutic agents.

Protein kinase C activity also plays an important role in cardiovascular disease. Increased protein kinase C activity in the vasculature has been shown to cause increased vasoconstriction and hypertension. A known protein kinase C inhibitor prevented this increase. Bilder, G. E. et al. *J. Pharmacol. Exp. Ther.* 252: 526–530 (1990). Because protein kinase C inhibitors demonstrate inhibition of the neutrophil oxidative burst, protein kinase C inhibitors are also useful in treating cardiovascular ischemia and improving cardiac function following ischemia. Muid, R. E. et al. FEBS Lett. 293: 169–172 (1990); Sonoki, H. et al. *Kokyu-To Junkan* 37: 669–674 (1989).

The role of protein kinase C in platelet function has also been investigated and as shown elevated protein kinase C levels being correlated with increased response to agonists. Bastyr III, E. J. and Lu, J. Diabetes 42: (Suppl. 1) 97A (1993). PKC has been implicated in the biochemical pathway in the platelet-activity factor modulation of microvascular permeability. Kobayashi et al., *Amer. Phys. Soc. H*1214–H1220 (1994). Potent protein kinase C inhibitors have been demonstrated to affect agonist-induced aggregation in platelets. Toullec, D. et al. *J. Biol. Chem.* 266: 15771–15781 (1991). Protein kinase C inhibitors also block agonist-induced smooth muscle cell proliferation. Matsumoto, H. and Sasaki, Y. Biochem. Biophys. Res. Commun. 158: 105–109 (1989). Therefore, the present compounds are useful in treating cardiovascular disease, atherosclerosis and restenosis.

Abnormal activity of protein kinase C has also been linked to dermatological disorders such as psoriasis. Horn, F. et al. *J. Invest. Dermatol.* 88: 220–222 (1987); Raynaud, F. and Evain-Brion, D. *Br. J. Dermatol.* 124: 542–546 (1991). Psoriasis is characterized by abnormal proliferation of keratinocytes. Known protein kinase C inhibitors have been shown to inhibit keratinocyte proliferation in a manner that parallels their potency as PKC inhibitors. Hegemann, L. et al. *Arch. Dermatol. Res.* 283: 456–460 (1991); Bollag, W. B. et al. *J. Invest. Dermatol.* 100: 240–246 (1993). Accordingly, the compounds as inhibitors of PKC are useful in treating psoriasis.

Protein kinase C has been linked to several different aspects of diabetes. Excessive activity of protein kinase C has been linked to insulin signaling defects and therefore to the insulin resistance seen in Type II diabetes. Karasik, A. et al. *J. Biol. Chem.* 265: 10226–10231 (1990); Chen, K. S. et al. *Trans. Assoc. Am. Physicians* 104: 206–212 (1991); Chin, J. E. et al. *J. Biol. Chem.* 268: 6338–6347 (1993). In addition, studies have demonstrated a marked increase in protein kinase C activity in tissues known to be susceptible to diabetic complications when exposed to hyperglycemic conditions. Lee, T.-S. et al. *J. Clin. Invest.* 83: 90–94 (1989); Lee, T.-S. et al. *Proc. Natl. Acad. Sci. USA* 86: 5141–5145 (1989); Craven, P. A. and DeRubertis, F. R. *J. Clin. Invest.* 83: 1667–1675 (1989); Wolf, B. A. et al. *J. Clin. Invest.* 87: 31–38 (1991); Tesfamariam, B. et al. *J. Clin. Invest.* 87: 1643–1648 (1991).

The compounds of the invention are also isozyme-selective. The compounds preferentially inhibit protein kinase C beta-1 and beta-2 isozyme over the protein kinase C isozymes, i.e., alpha, gamma, delta, epsilon, zeta, and eta. In general, the compounds demonstrate a minimum of a ten fold differential in the dosage required to inhibit PKC beta-1 or beta-2 isozyme and the dosage required for equal inhibition of the alpha protein kinase C isozyme as measured in the PKC assay. Accordingly, compounds of the present invention inhibit beta-1 and beta-2 isozymes of protein kinase C at much lower concentrations with minimal inhibition of the other PKC isozymes. This isozyme selectivity is demonstrated in Table 2 for a representative compound.

TABLE 2

| Compound (Ex) | Isozymes ED50 ($\mu$M) | | | | | | |
|---|---|---|---|---|---|---|---|
| | α | β1 | β2 | γ | δ | ε | ζ | η |
| 5 | .28 | 0.019 | 0.005 | .23 | .31 | 1.0 | 38 | 0.035 |

Because of this selectivity, the compounds are particularly useful in treating those disease states in which protein kinase C isozyme beta-1 or beta-2 are associated. For example, the elevated blood glucose levels found in diabetes leads to an isozyme-specific elevation of the beta-2 isozyme in vascular tissues. Inoguchi et al., *Proc. Natl. Acad. Sci. USA* 89: 11059–11065 (1992). A diabetes-linked elevation of the beta isozyme in human platelets has been correlated with their altered response to agonists. Bastyr III, E. J. and Lu, J. *Diabetes* 42: (Suppl 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88: 9315–9319 (1991); Hsieh et al., *J. Biol. Chem.* 268: 15118–15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847–15853 (1993).

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 1 to about 500 mg, more usually about 5 to about 300 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, the compounds of the present invention may be administered topically. Topical formulations are ointments, creams, and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added to an amount to achieve the desired concentration.

Gels comprise a base selection from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should only be a range sufficient to permit ready application of the formulation to the an affected tissue area in an amount which will deliver the desired amount of compound.

The customary amount of a topical formulation to be applied to an affected tissue will depend upon an affected tissue size and concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu$g/$cm^2$, more preferably, from about 50 to about 200 $\mu$g/$cm^2$, and, most preferably, from about 60 to about 100 $\mu$g/$cM^2$.

The following formulation examples are illustrative only and are not intended to limit the scope of the invention in any way.

FORMULATION 1

Hard gelatin capsules are prepared using the following ingredients:

|  | Quantity (mg/capsule) |
| --- | --- |
| Active agent | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

|  | Quantity (mg/capsule) |
| --- | --- |
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Quantity (mg/capsule) |
| --- | --- |
| Active agent | 0.25 |
| ethanol | 29.75 |
| Propellant 22 | 70.00 |
| (chlorodifluoromethane) |  |
| Total | 100.00 |

The active compound is mixed with ethanol. The mixture is added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets each containing 60 mg of active ingredient are made as follows:

|  | Quantity (mg/capsule) |
| --- | --- |
| Active agent | 60 mg |
| starch | 45 mg |
| microcrystalline cellulose | 35 mg |
| polyvinylpyrrolidone | 4 mg |
| (as 10% solution in water) |  |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

|  | Quantity (mg/capsule) |
| --- | --- |
| Active agent | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

|                              | Quantity (mg/capsule) |
|------------------------------|----------------------|
| Active agent                 | 225 mg               |
| saturated fatty acid glycerides | 2,000 mg          |
| Total                        | 2,225 mg             |

The active ingredient is passed through a No. 60 mesh U.S. sieve-and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per mL dose are made as follows:

|                              | Quantity (mg/capsule) |
|------------------------------|----------------------|
| Active agent                 | 50 mg                |
| sodium carboxymethyl cellulose | 50 mg              |
| syrup                        | 1.25 mL              |
| benzoic acid solution        | 0.10 mL              |
| flavor                       | q.v.                 |
| color                        | q.v.                 |
| purified water to total      | 5 mL                 |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

|                | Quantity (mg/capsule) |
|----------------|----------------------|
| Active agent   | 250 mg               |
| isotonic saline | 1000 mg             |

The solution of the above ingredients is administered intravenously at a rate of 1 mL per minute to a subject in need of treatment.

We claim:

1. A method for treating restenosis comprising administering a therapeutically effective amount of a PKC inhibitor.

2. A method of treating restenosis following revascularization comprising administering a therapeutically effective amount of a PKC inhibitor for a time sufficient to prevent restenosis.

3. A method of treating restenosis following revascularization comprising the local delivery of a PKC inhibitor.

4. A method of preventing smooth muscle cell proliferation in a patient and need thereof comprising administering a PKC inhibitor.

5. A method of preventing smooth muscle cell proliferation in a patient and need thereof comprising administering locally an effective therapeutic amount of a PKC inhibitor.

6. Use of a PKC inhibitor for the preparation of a medicament for the treatment of restenosis.

7. The use of claim 6 wherein restenosis is following revascularization.

* * * * *